(12) United States Patent
Lee et al.

(10) Patent No.: US 11,926,603 B2
(45) Date of Patent: Mar. 12, 2024

(54) COMPOUND, COMPOSITION, ORGANIC OPTOELECTRONIC DIODE, AND DISPLAY DEVICE

(71) Applicants: SAMSUNG SDI CO., LTD., Yongin-si (KR); SAMSUNG ELECTRONICS CO., LTD., Suwon-si (KR)

(72) Inventors: Hanill Lee, Suwon-si (KR); Giwook Kang, Suwon-si (KR); Byungku Kim, Suwon-si (KR); Chang Ju Shin, Suwon-si (KR); Dongkyu Ryu, Suwon-si (KR); Eun Sun Yu, Suwon-si (KR); Kipo Jang, Suwon-si (KR)

(73) Assignees: SAMSUNG SDI CO., LTD., Yongin-si (KR); SAMSUNG ELECTRONICS CO., LTD, Suwon-si (KR)

( * ) Notice: Subject to any disclaimer, the term of this patent is extended or adjusted under 35 U.S.C. 154(b) by 847 days.

(21) Appl. No.: 16/962,920

(22) PCT Filed: Jan. 10, 2019

(86) PCT No.: PCT/KR2019/000402
§ 371 (c)(1),
(2) Date: Jul. 17, 2020

(87) PCT Pub. No.: WO2019/146938
PCT Pub. Date: Aug. 1, 2019

(65) Prior Publication Data
US 2021/0130304 A1 May 6, 2021

(30) Foreign Application Priority Data
Jan. 24, 2018 (KR) .................... 10-2018-0008776

(51) Int. Cl.
*H01L 51/50* (2006.01)
*C07D 209/82* (2006.01)
(Continued)

(52) U.S. Cl.
CPC ......... *C07D 251/24* (2013.01); *C07D 209/82* (2013.01); *H10K 59/00* (2023.02); *H10K 85/6572* (2023.02); *H10K 2101/30* (2023.02)

(58) Field of Classification Search
None
See application file for complete search history.

(56) References Cited

U.S. PATENT DOCUMENTS

2007/0032000 A1* 2/2007 Yeh .................. G09G 3/3648
438/149
2016/0218288 A1* 7/2016 Huh .................. H10K 85/6572

FOREIGN PATENT DOCUMENTS

CN 105593336 A 5/2016
CN 105612237 A 5/2016
(Continued)

OTHER PUBLICATIONS

Chinese Search report dated Oct. 10, 2022.
International Search Report dated Apr. 19, 2019 for PCT/KR2019/000402.

*Primary Examiner* — Gregory D Clark
(74) *Attorney, Agent, or Firm* — Lee IP Law, P.C.

(57) ABSTRACT

Disclosed are a compound represented by Chemical Formula 1, a composition comprising the same, an organic optoelectronic diode, and a display device.
Chemical formula 1 is as defined in the specification.

20 Claims, 1 Drawing Sheet

(51) Int. Cl.
  *C07D 251/24*   (2006.01)
  *H10K 59/00*    (2023.01)
  *H10K 85/60*    (2023.01)
  *H10K 101/30*   (2023.01)

(56) References Cited

FOREIGN PATENT DOCUMENTS

| | | | |
|---|---|---|---|
| CN | 105684179 A | 6/2016 | |
| CN | 106565433 A | 4/2017 | |
| JP | 2006-143845 A | 6/2006 | |
| KR | 10-0948700 B1 | 3/2010 | |
| KR | 10-1183722 B1 | 9/2012 | |
| KR | 10-2012-0116282 A | 10/2012 | |
| KR | 10-2014-0042630 A | 4/2014 | |
| KR | 10-2014-0113483 A | 9/2014 | |
| KR | 10-2015-0117173 A | 10/2015 | |
| KR | 10-2016-0034230 A | 3/2016 | |
| KR | 2016-034230 | * 3/2016 | ............ H01L 51/50 |
| KR | 10-1618683 B1 | 5/2016 | |
| KR | 10-2017-0126811 A | 11/2017 | |
| WO | WO 2016/039500 A1 | 3/2016 | |
| WO | WO 2017/069258 A1 | 4/2017 | |

* cited by examiner

【Figure 1】
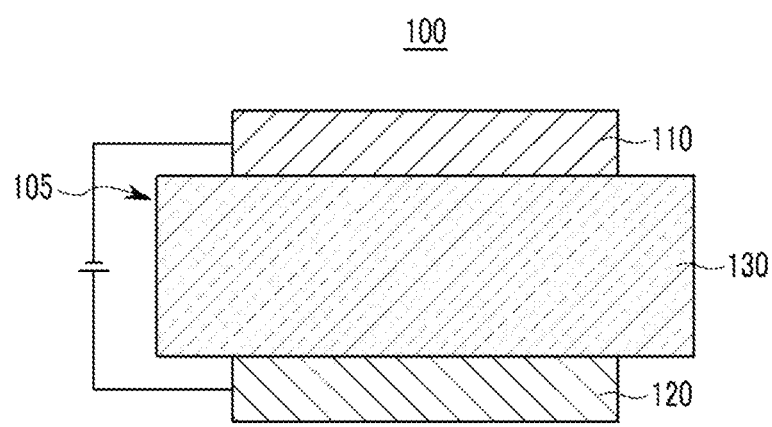
【Figure 2】
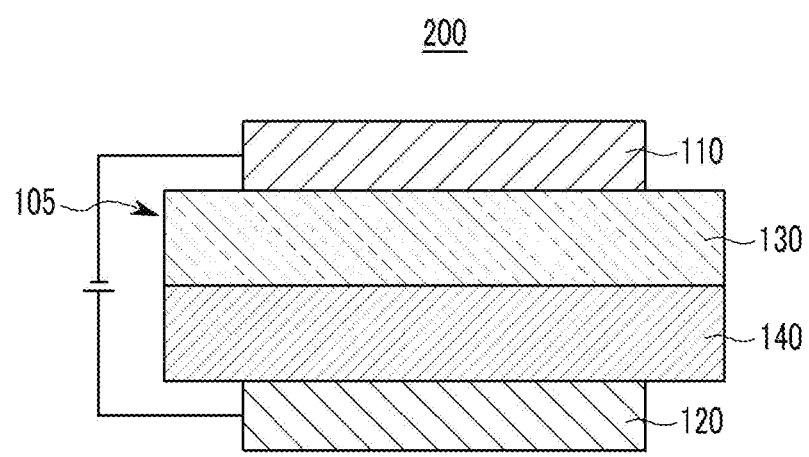

COMPOUND, COMPOSITION, ORGANIC OPTOELECTRONIC DIODE, AND DISPLAY DEVICE

CROSS REFERENCE TO RELATED APPLICATIONS

This is the U.S. national phase application based on PCT Application No. PCT/KR2019/000402, filed Jan. 10, 2019, which is based on Korean Patent Application No. 10-2018-0008776, filed Jan. 24, 2018, the entire contents of all of which are hereby incorporated by reference.

TECHNICAL FIELD

A compound, a composition, an organic optoelectronic diode, and a display device are disclosed.

BACKGROUND ART

An organic optoelectronic diode is a device that converts electrical energy into photoenergy, and vice versa.

An organic optoelectronic diode may be classified as follows in accordance with its driving principles. One is a photoelectric diode where excitons are generated by photoenergy, separated into electrons and holes, and are transferred to different electrodes to generate electrical energy, and the other is a light emitting diode where a voltage or a current is supplied to an electrode to generate photoenergy from electrical energy.

Examples of the organic optoelectronic diode may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and performance of an organic light emitting diode may be affected by organic materials disposed between electrodes.

DISCLOSURE

Technical Problem

An embodiment provides a compound for an organic optoelectronic diode capable of realizing an organic optoelectronic diode having high efficiency and a long life-span.

Another embodiment provides a composition for an organic optoelectronic diode including the compound.

Another embodiment provides an organic optoelectronic diode including the compound or the composition.

Another embodiment provides a display device including the organic optoelectronic diode.

Technical Solution

According to an embodiment, a first compound for an organic optoelectronic diode is provided.

[Chemical Formula 1]

In Chemical Formula 1, $R^1$ to $R^{14}$ are independently hydrogen, deuterium, a substituted or unsubstituted C1 to C20 alkyl group, a substituted or unsubstituted C6 to C12 aryl group, a cyano group, or a combination thereof, $R^1$ and $R^2$ are independently present or linked to each other to form a ring, $R^3$ and $R^4$ are independently present or linked to each other to form a ring, $L^1$ is a single bond, a substituted or unsubstituted C6 to C30 arylene group, or a substituted or unsubstituted C2 to C30 heteroarylene group, n1 and n3 are independently an integer of 0 or 1, and
n2 is an integer of 1.

According to another embodiment, a composition including the first compound represented by Chemical Formula 1 and a second compound represented by Chemical Formula 2.

[Chemical Formula 2]

In Chemical Formula 2,

L² and L³ are independently a single bond, a substituted or unsubstituted C6 to C30 arylene group, or a substituted or unsubstituted C2 to C30 heteroarylene group, Y¹ and Y² are independently a substituted or unsubstituted C6 to C30 aryl group or a substituted or unsubstituted C2 to C30 heterocyclic group, R¹⁵ to R²⁰ are independently hydrogen, deuterium, a substituted or unsubstituted C1 to C10 alkyl group, a substituted or unsubstituted C6 to C30 aryl group, a substituted or unsubstituted C2 to C30 heterocyclic group, a cyano group, or a combination thereof, and m is one of integers of 0 to 2.

According to another embodiment, an organic optoelectronic diode includes an anode and a cathode facing each other, and at least one organic layer disposed between the anode and the cathode, wherein the organic layer includes the compound or composition.

According to another embodiment, a display device including the organic optoelectronic diode is provided.

Advantageous Effects

An organic optoelectronic diode having high efficiency and a long life-span may be realized.

DESCRIPTION OF THE DRAWINGS

FIGS. 1 and 2 are cross-sectional views showing organic light emitting diodes according to embodiments.

DESCRIPTION OF SYMBOLS 100, 200: organic light emitting diode
105: organic layer
110: cathode
120: anode
130: light emitting layer
140: hole auxiliary layer

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In addition, in a specific example of the present invention, the "substituted" refers to replacement of at least one hydrogen of a substituent or a compound by deuterium, a C1 to C20 alkyl group, a C6 to C30 aryl group, or a cyano group. In addition, in a specific example of the present invention, the "substituted" refers to replacement of at least one hydrogen of a substituent or a compound by deuterium, a C1 to C5 alkyl group, a C6 to C18 aryl group, a cyano group. In addition, in a specific example of the present invention, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

In the present specification, when a definition is not otherwise provided, "hetero" refers to one including one to three heteroatoms selected from N, O, S, P, and Si, and remaining carbons in one functional group.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof, but are not limited thereto.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or combination thereof, but is not limited thereto.

In the present specification, hole properties refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUO) level.

In the present specification, "linked to each other to form a ring" means that adjacent groups are linked to each other to form a substituted or unsubstituted aromatic ring or a substituted or unsubstituted heteroaromatic ring.

For example, "linked to each other to form a ring" means that adjacent groups are linked to each other to form a substituted or unsubstituted aromatic ring, and more specifically, it means that adjacent groups are linked to each other to form a substituted or unsubstituted phenyl group.

Hereinafter, a compound for an organic optoelectronic diode according to an embodiment is described.

The compound for the organic photoelectric device according to an embodiment is represented by Chemical Formula 1.

[Chemical Formula 1]

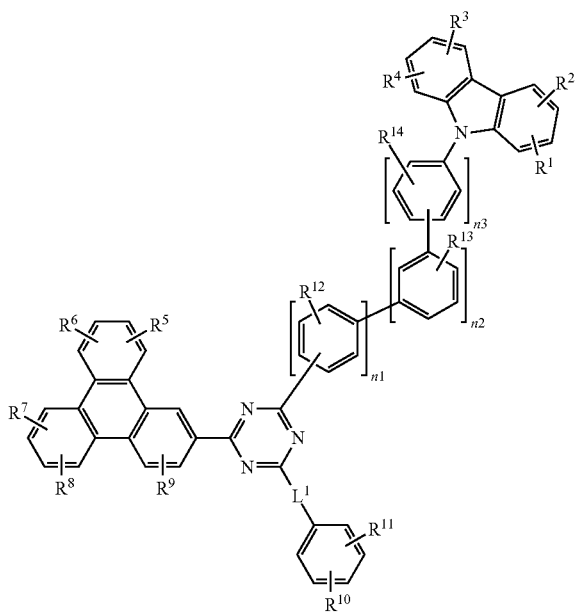

In Chemical Formula 1, $R^1$ to $R^{14}$ are independently hydrogen, deuterium, a substituted or unsubstituted C1 to C20 alkyl group, a substituted or unsubstituted C6 to C12 aryl group, a cyano group, or a combination thereof, $R^1$ and $R^2$ are independently present or linked to each other to form a ring, $R^3$ and $R^4$ are independently present or linked to each other to form a ring, $L^1$ is a single bond, a substituted or unsubstituted C6 to C30 arylene group, or a substituted or unsubstituted C2 to C30 heteroarylene group, n1 and n3 are independently an integer of 0 or 1, and n2 is an integer of 1.

The compound represented by Chemical Formula 1 has a three-dimensional and asymmetric molecular structure in which carbazole, triphenylene, and a phenyl group are linked in the center of triazine, at least one meta-phenylene group is included between carbazole and triazine, and triphenylene and triazine are directly linked without a linker.

By including at least one meta-phenylene linker between the carbazole and triazine, the compound has a relatively shallow HOMO value, which is desirable for hole injection and transport and by linking the triphenylene and triazine without a linking group, the compound has a deep LUMO energy level, which is desirable for electron injection and transport.

That is, in the device including the compound represented by Chemical Formula 1, hole/electron injection and transport are desirable, and thus may have desirable properties for life-span.

In addition, by substituting the triazine core with the carbazole, bipolar properties are strengthened. A n-bond through the CN bond is broken by substituting the carbazole in an N-direction, and thus an electron cloud between HOMO and LUMO is localized to maximize improvement of life-span.

A calculated HOMO energy level of the compound represented by Chemical Formula 1 may be, for example, −6.0 eV to −5.0 eV, specifically −5.8 eV to −5.2 eV, more specifically −5.8 eV to −5.5 eV, and most specifically −5.8 eV to −5.7 eV.

A calculated LUMO energy level may be, for example, −2.2 eV to −2.9 eV, specifically −2.3 eV to −2.8 eV, and more specifically −2.4 eV to −2.75 eV.

The HOMO energy level and LUMO energy level are measured using a cyclic voltammetry (CV) composed of EC-Epsilon and c-3 cell stand of BAS (bioanalytical systems Inc. USA) and a specific measurement method is as follows.

After setting a potential of ferrocene to −4.8 eV compared with an energy level of vacuum, $Ag/Ag^+$ is used as a reference electrode and a solution in which tetrabutylammonium tetrafluoroborate is dissolved in a dichloromethane solvent at a concentration of 0.1 M is used as an electrolyte. After measuring the ferrocene and each compound at a rate of 100 mV/sec, the HOMO energy level and LUMO energy level are calculated using the following calculation equation.

$$\text{HOMO(or LUMO)(eV)} = -4.8 - (E_{onset} - E_{1/2}(\text{Ferrocene})) \quad \text{<Calculation Equation>}$$

Herein, $E_{onset}$ is a potential at which redox starts and $E_{1/2}$(Ferrocene) is a half-wave potential of ferrocene.

In general, the HOMO energy level and LUMO energy level of the green dopant are formed between −5.5 eV to −5.0 eV and −2.9 eV to −2.5 eV, respectively. When a difference between the HOMO energy level of the host and the HOMO energy level of the dopant and/or a difference between the LUMO energy level of the host and the LUMO energy level of the dopant are 0 eV to 0.2 eV, it becomes very desirable to form an exciton. If it is out of the above range, there is a high risk of breaking a balance of the device.

For example, it may be $0 \leq n1+n3 \leq 1$.

As an example, n2 may be 1, and all n1 and n3 may be 0.

For example, n2 may be 1, n1 may be 1, and n3 may be 0.

For example, n2 may be 1, n1 may be 0, and n3 may be 1.

As a specific example, Chemical Formula 1 may be represented by one of Chemical Formula 1-1 to Chemical Formula 1-6.

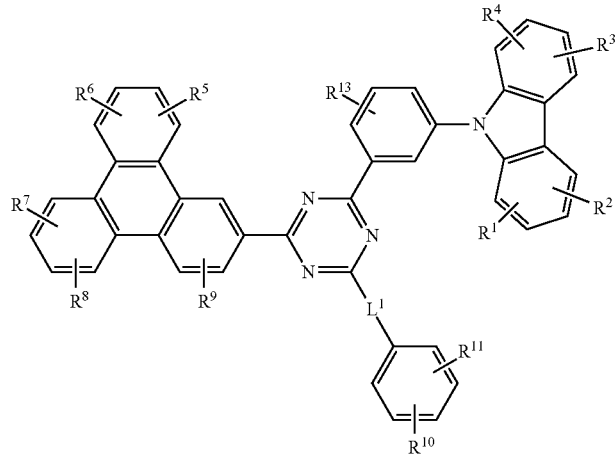

[Chemical Formula 1-1]

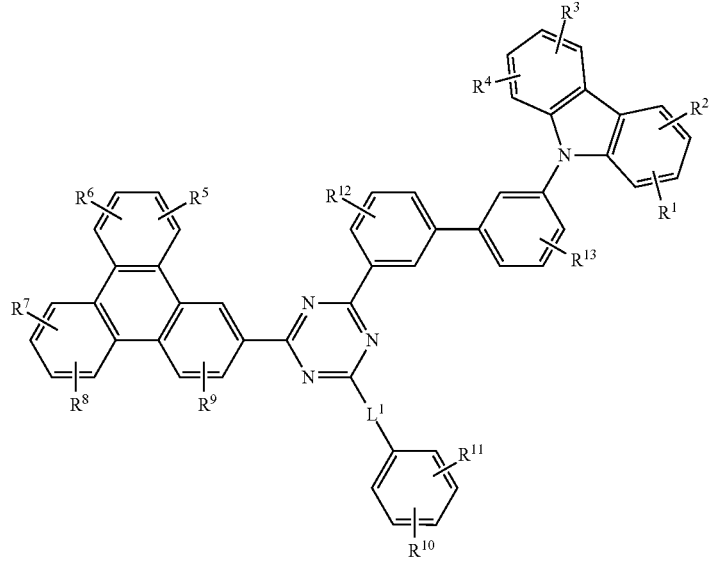

[Chemical Formula 1-2]

[Chemical Formula 1-3]
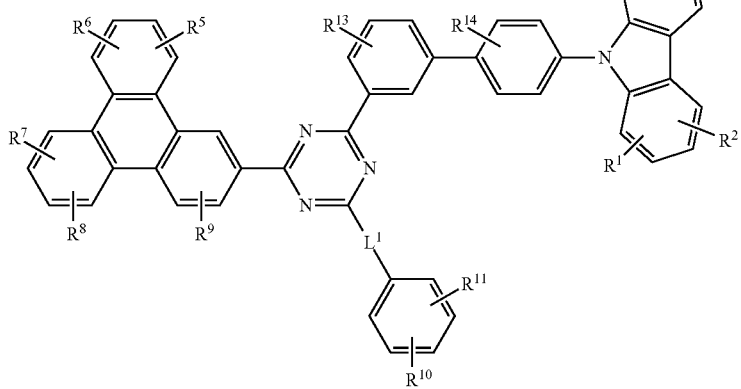
[Chemical Formula 1-4]
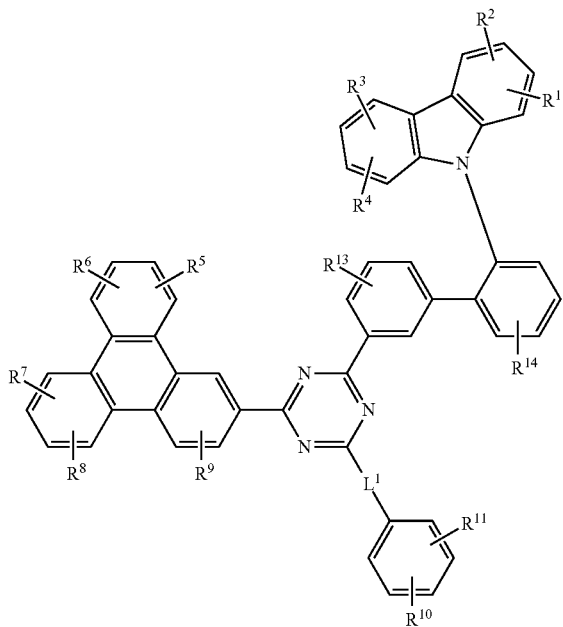
[Chemical Formula 1-5]
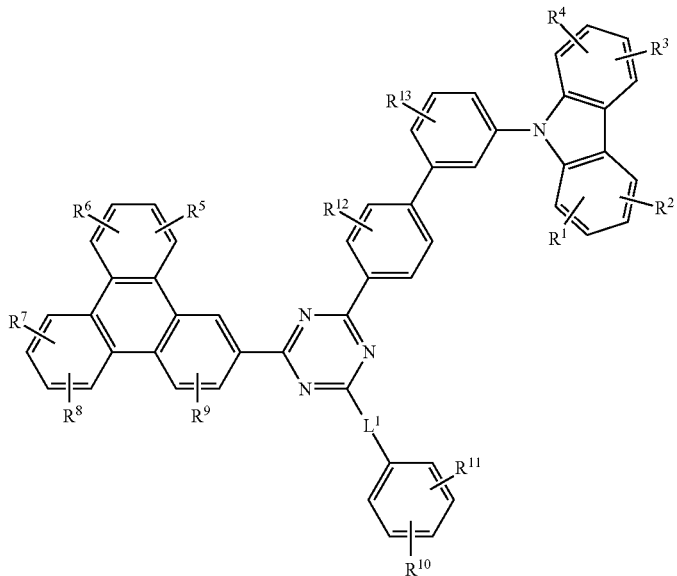

-continued

[Chemical Formula 1-6]

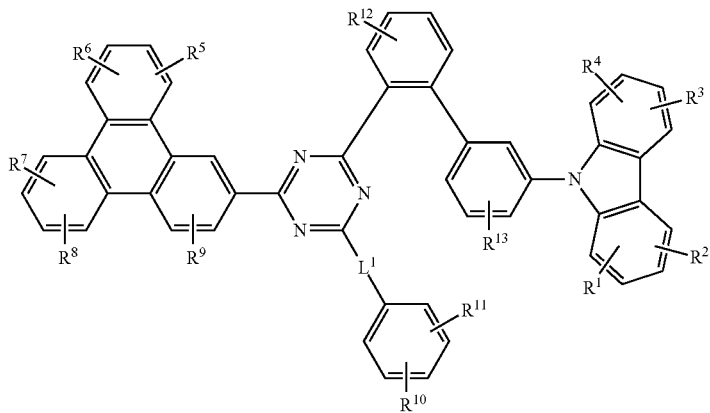

In the above Chemical Formulas 1-1 to 1-6, the definitions of $R^1$ to $R^{14}$ and $L^1$ are the same as described above.

For example, the compound represented by Chemical Formula 1 may be represented by one of Chemical Formula 1-1 to Chemical Formula 1-3, but is not limited thereto.

For example, each of $R^1$ to $R^{14}$ may independently be hydrogen, a C1 to C10 alkyl group, a C6 to C12 aryl group, or a cyano group.

For example, each of $R^1$ to $R^{14}$ may independently be hydrogen, a methyl group, an ethyl group, a phenyl group, a biphenyl group, a naphthyl group, or a cyano group.

For example, each of $R^1$ to $R^{14}$ may independently be hydrogen or a C6 to C12 aryl group.

For example, $R^1$ and $R^2$ may independently be present or linked to each other to form a substituted or unsubstituted aromatic ring.

For example, $R^3$ and $R^4$ may independently be present or linked to each other to form a substituted or unsubstituted aromatic ring.

For example, $R^1$ to $R^4$ may independently be present and may be, for example hydrogen or a phenyl group, but are not limited thereto.

For example, $R^1$ and $R^2$ or $R^3$ and $R^4$ may be linked to each other to form a substituted or unsubstituted aromatic ring, and may be represented by one of Chemical Formula 1a to Chemical Formula 1c, but are not limited thereto.

[Chemical Formula 1a]

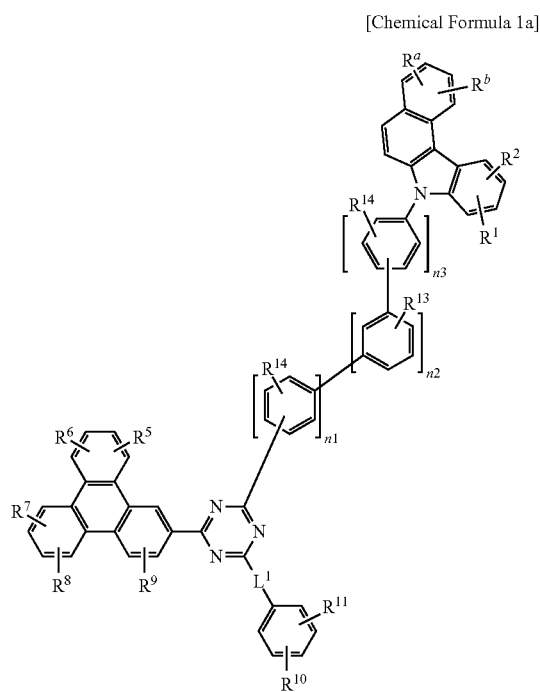

[Chemical Formula 1b]

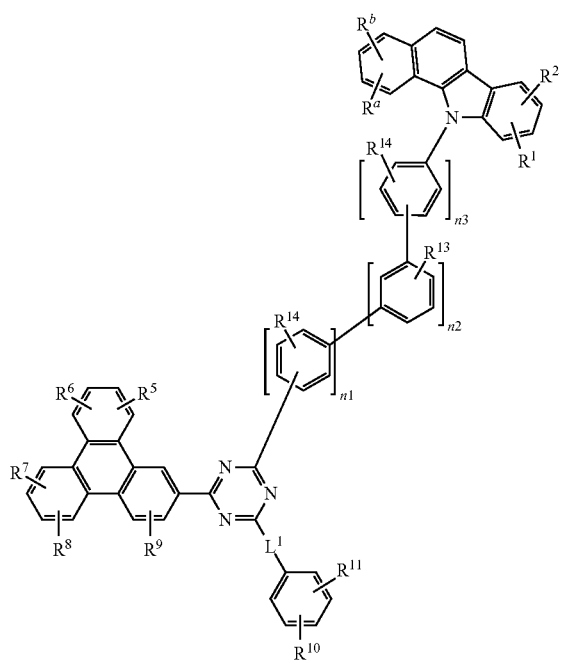

[Chemical Formula 1c]

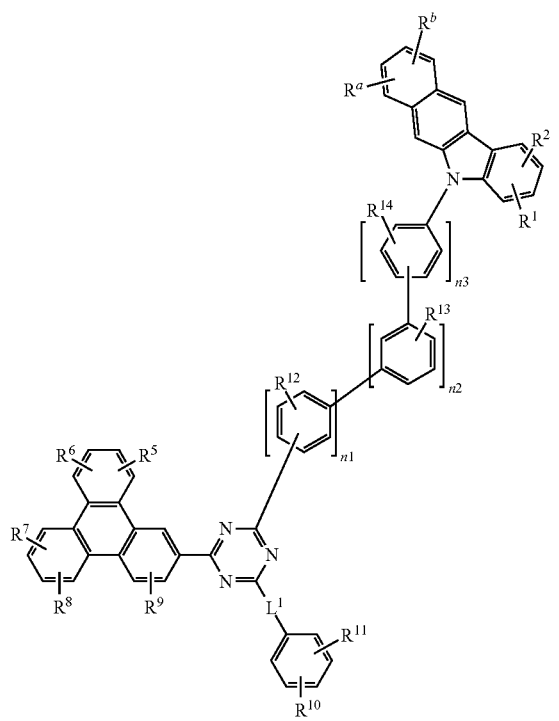

In Chemical Formula 1a to Chemical Formula 1c, the definitions of $R^1$ to $R^{14}$, and n1 to n3 are the same as described above, and $R^a$ and $R^b$ are independently hydrogen, deuterium, a substituted or unsubstituted C1 to C20 alkyl group, a substituted or unsubstituted C6 to C12 aryl group, a cyano group, or a combination thereof.

For example, $R^a$ and $R^b$ may be all hydrogen, but are not limited thereto.

For example, $R^5$ to $R^9$ may independently be hydrogen, a C1 to C5 alkyl group, a C6 to C12 aryl group, or a cyano group.

As a specific example, $R^5$ to $R^9$ may independently be hydrogen, a methyl group, an ethyl group, a phenyl group, or a cyano group, but are not limited thereto.

For example, $R^{10}$ and $R^{11}$ may independently be hydrogen, a C1 to C5 alkyl group, a C6 to C12 aryl group, or a cyano group.

As a specific example, $R^{10}$ and $R^{11}$ may independently be hydrogen, a methyl group, an ethyl group, a phenyl group, a meta-biphenyl group, an ortho-biphenyl group, a para-biphenyl group, or a cyano group, but are not limited thereto.

For example, $R^{12}$ to $R^{14}$ may independently be hydrogen, a C1 to C5 alkyl group, a C6 to C12 aryl group, or a cyano group.

As a specific example, $R^{12}$ to $R^{14}$ may independently be hydrogen, a methyl group, an ethyl group, a phenyl group, or a cyano group, but are not limited thereto.

For example, $L^1$ may be a single bond, or a substituted or unsubstituted C6 to C20 arylene group.

As a specific example, $L^1$ may be a single bond, a substituted or unsubstituted phenylene group, a substituted or unsubstituted biphenylene group, a substituted or unsubstituted terphenylene group, or a substituted or unsubstituted naphthylene group.

For example, $L^1$ may be a single bond, a substituted or unsubstituted m-phenylene group, a substituted or unsubstituted p-phenylene group, a substituted or unsubstituted o-phenylene group, a substituted or unsubstituted m-biphenylene group, a substituted or unsubstituted p-biphenylene group, a substituted or unsubstituted o-biphenylene group, a substituted or unsubstituted m-terphenylene group, a substituted or unsubstituted p-terphenylene group, or a substituted or unsubstituted o-terphenylene group.

For example, $L^1$ may be a single bond or one of the substituted or unsubstituted linking groups of Group I.

[Group I]

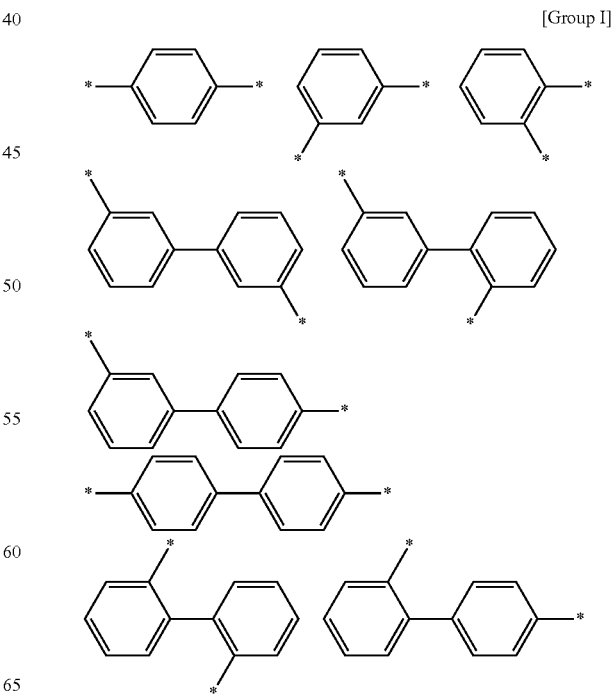

For example, the compound represented by Chemical Formula 1 may be one selected from compounds of Group 1 below, but is not limited thereto.
[Group 1]
1
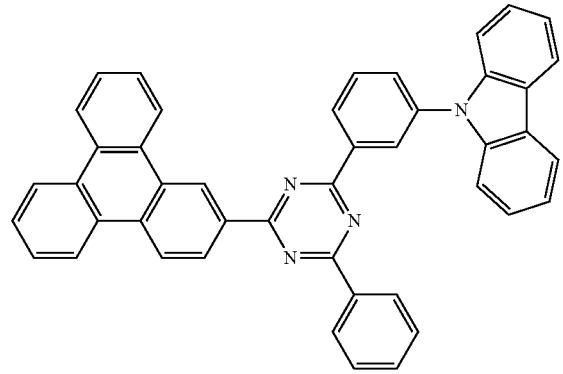
2
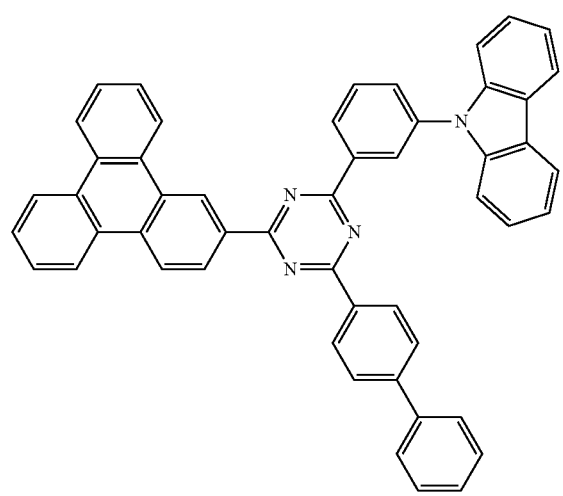
3
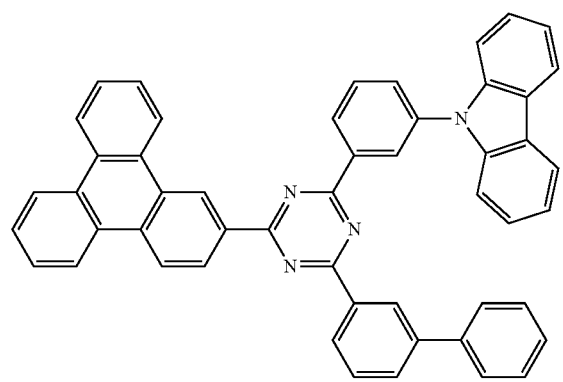
4
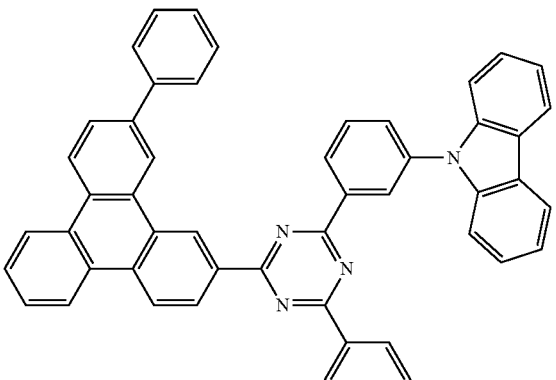
5
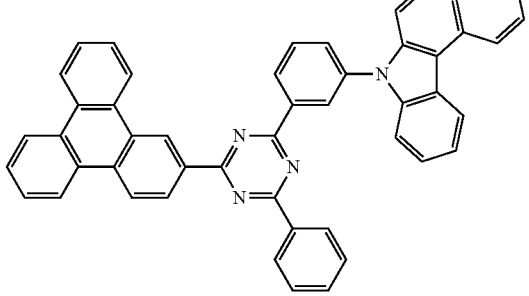
6
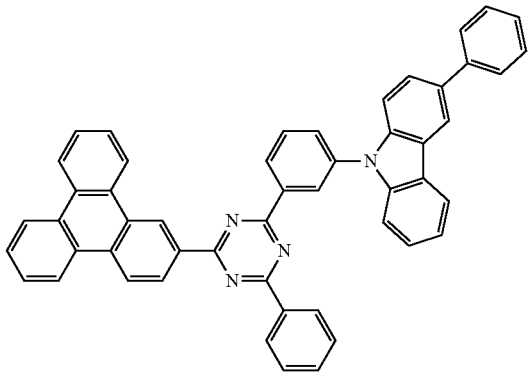
7
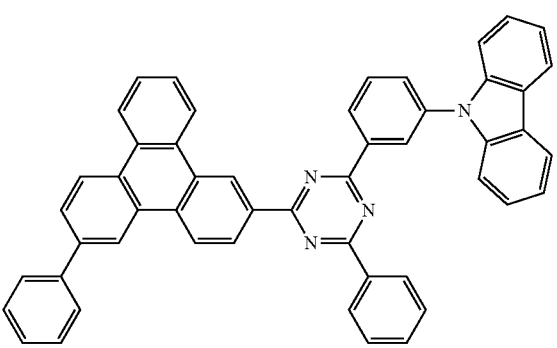

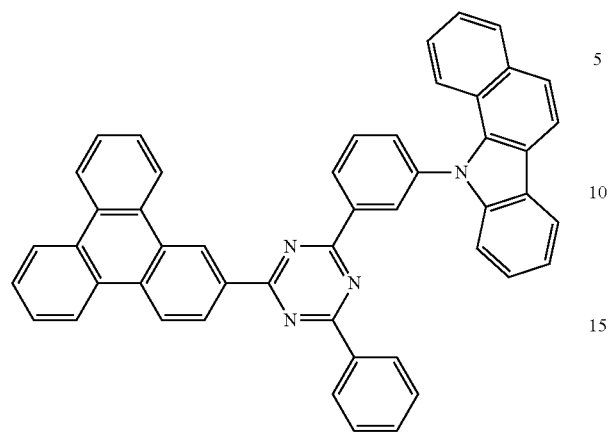
8
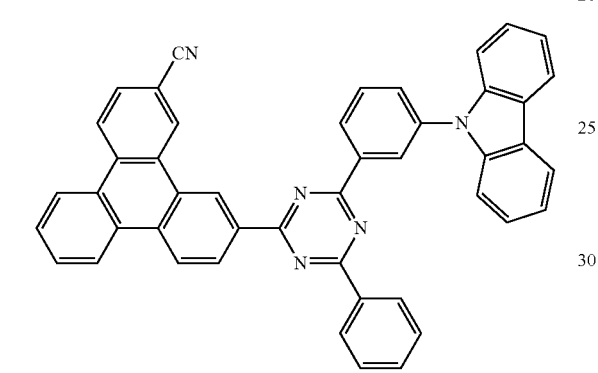
9
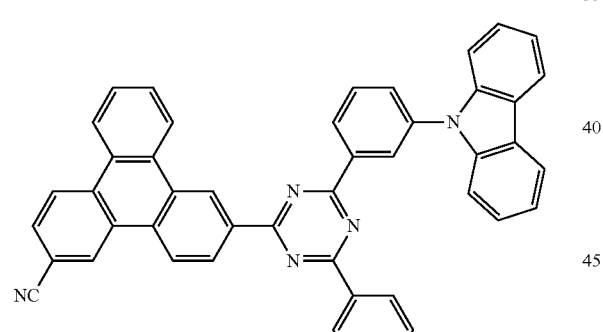
10
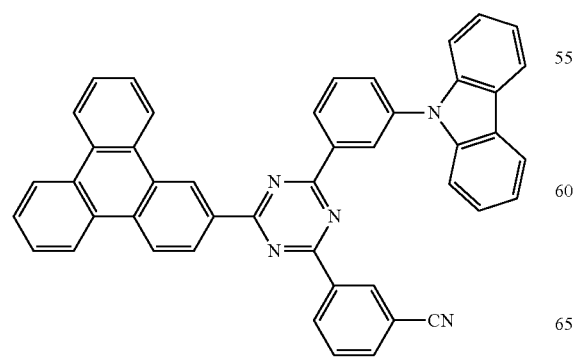
11
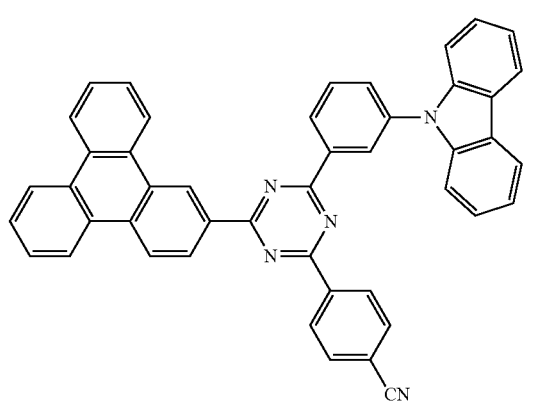
12
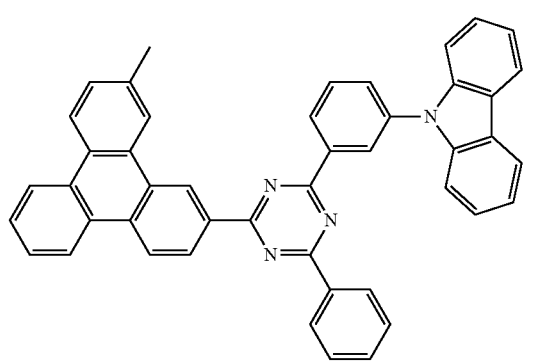
13
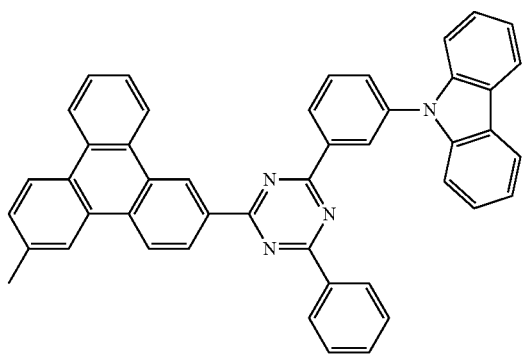
14
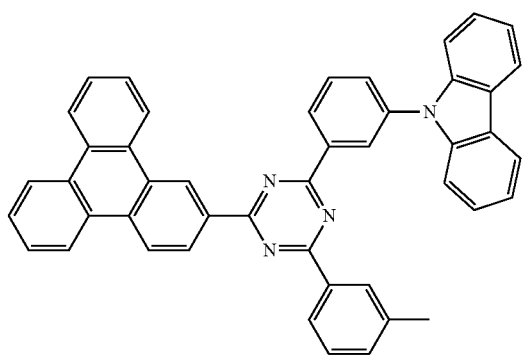
15

16
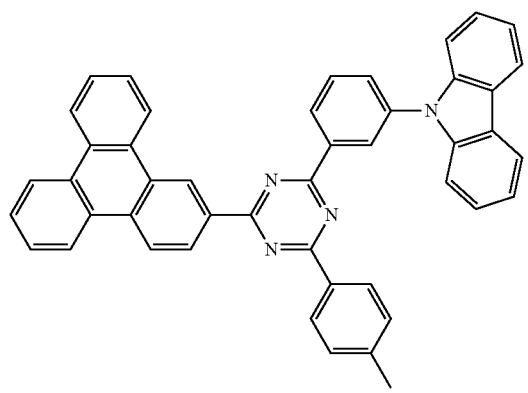
17
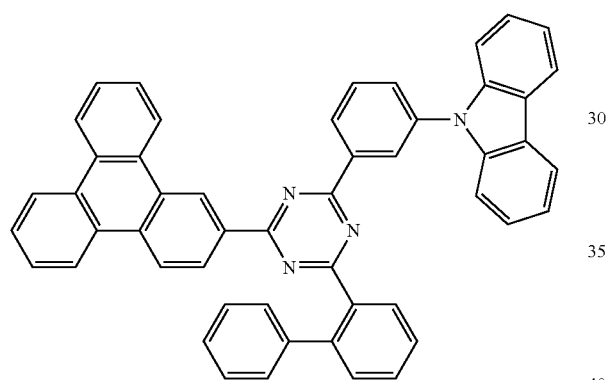
18
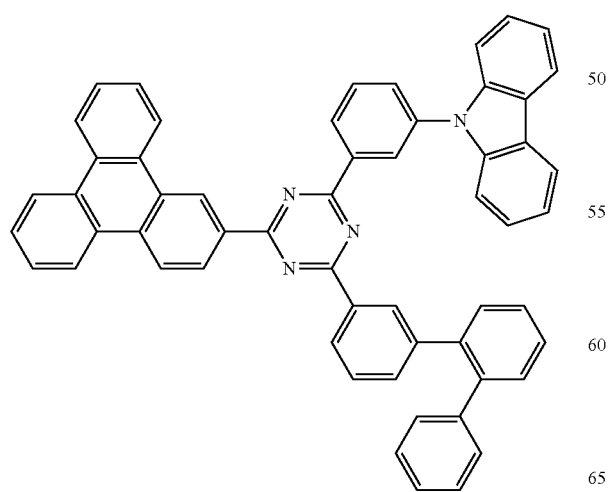
19
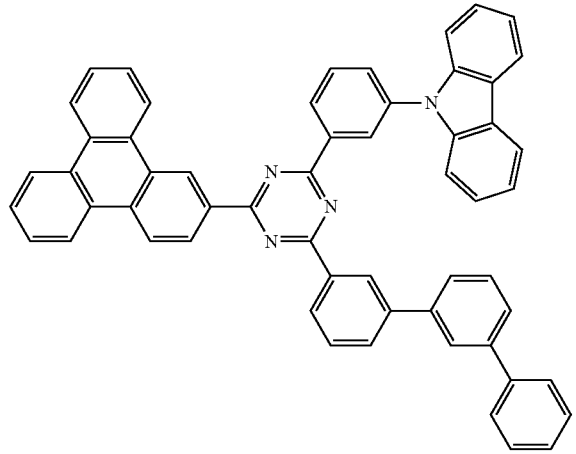
20
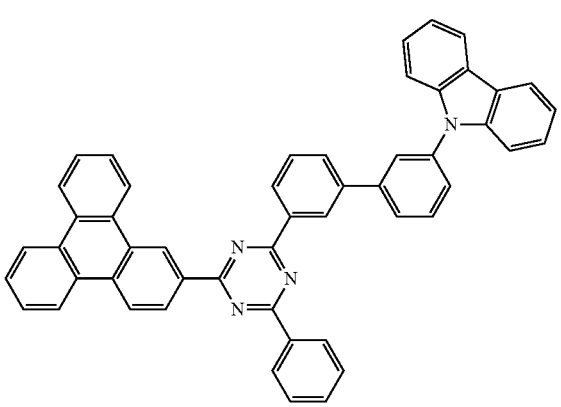
21
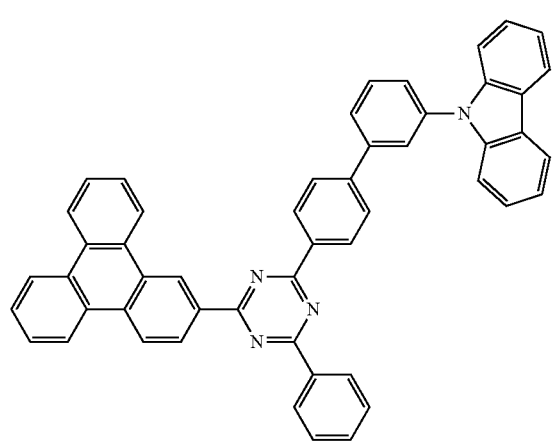

22
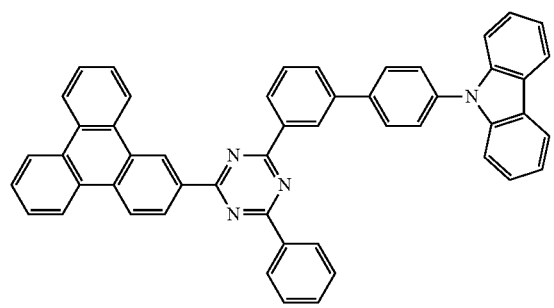
23
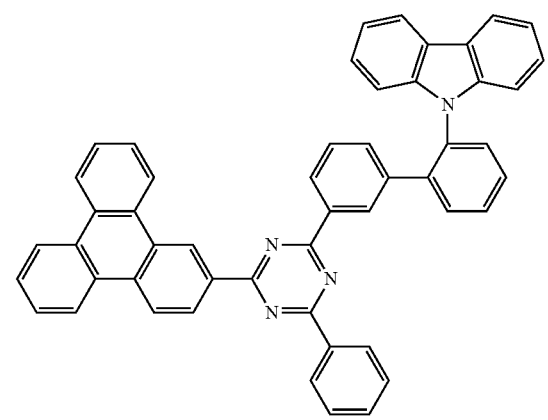
24
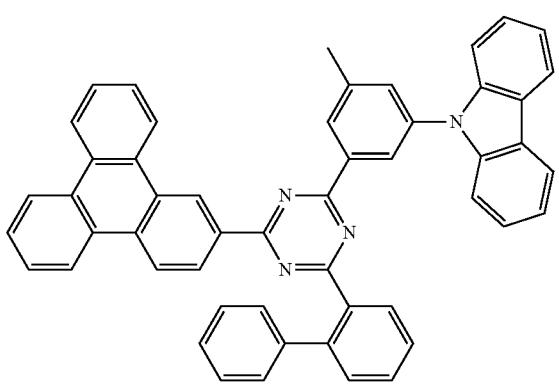
25
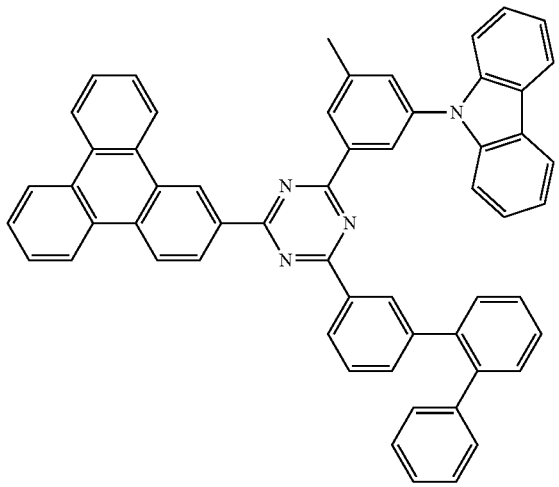
26
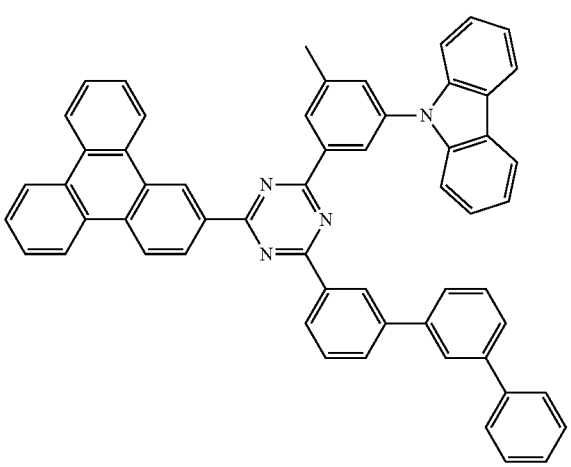
27
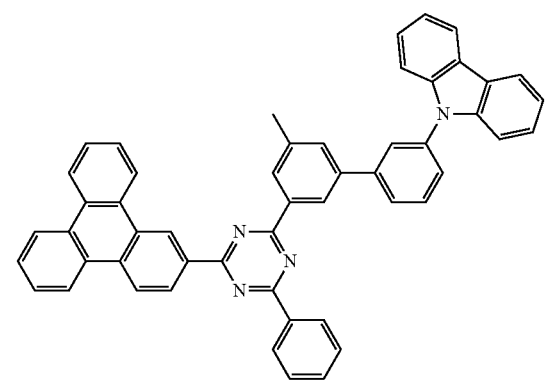

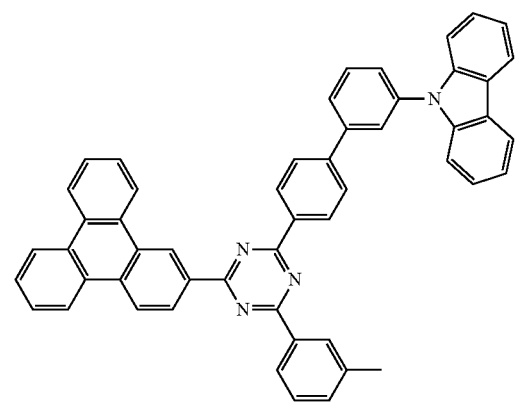
28
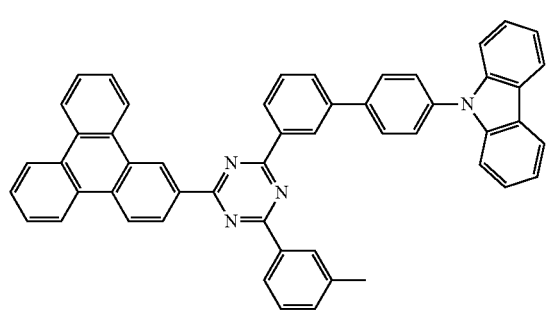
29
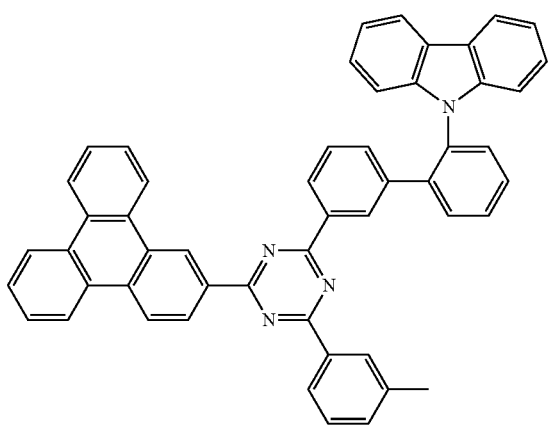
30
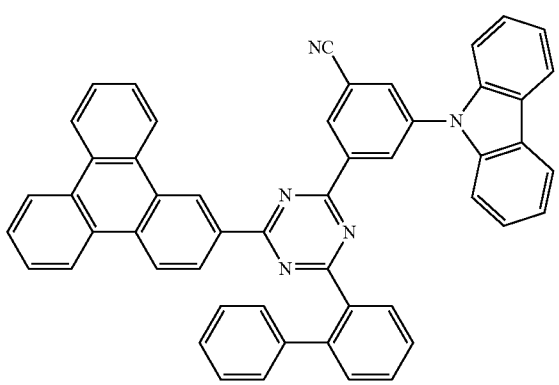
31
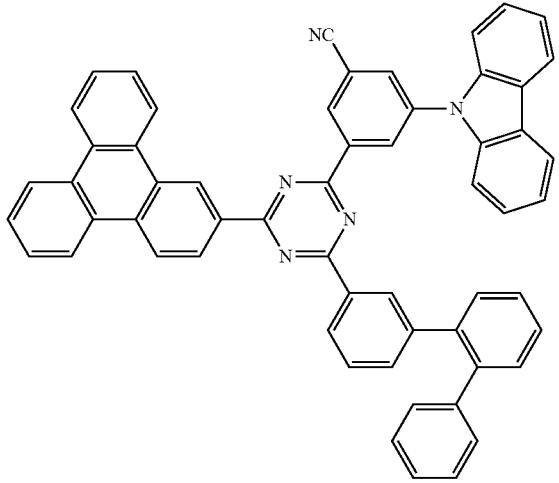
32
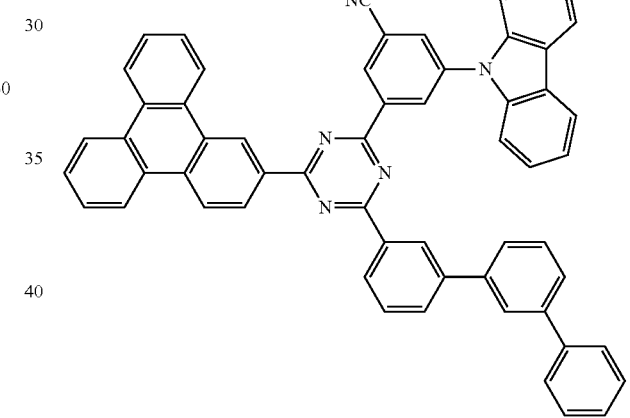
33
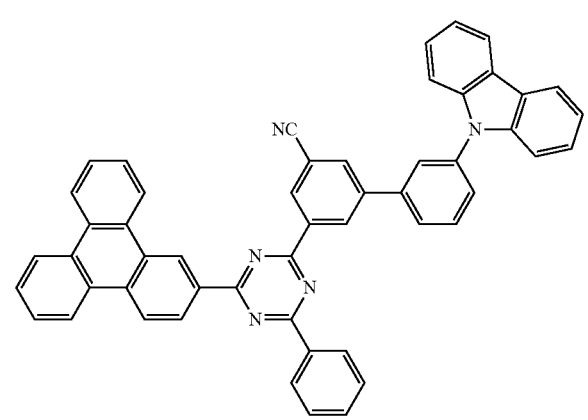
34

35

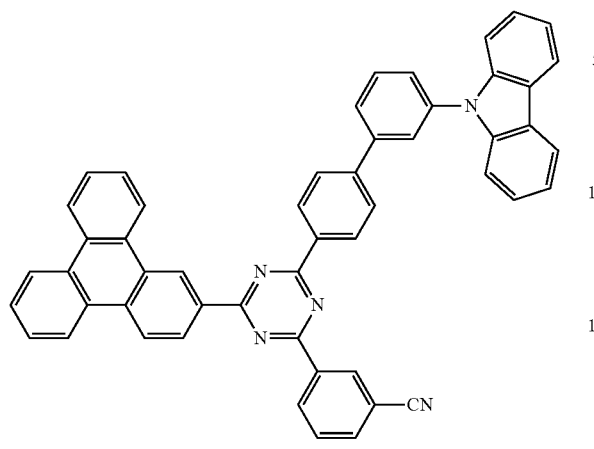

36

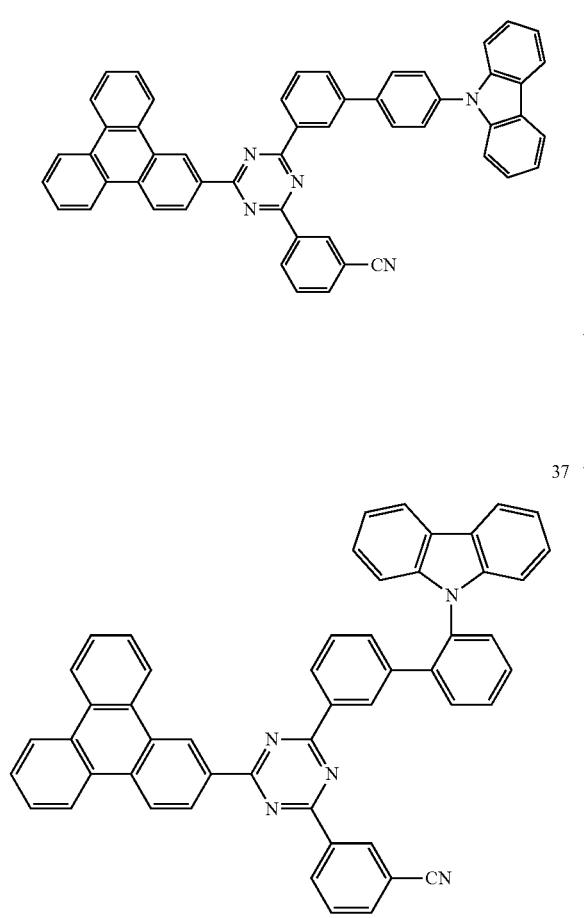

37

[Chemical Formula 2]

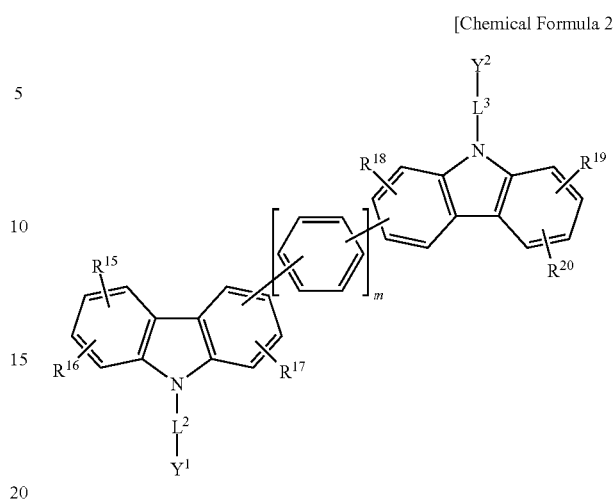

In Chemical Formula 2, $L^2$ and $L^3$ are independently a single bond, a substituted or unsubstituted C6 to C30 arylene group, or a substituted or unsubstituted C2 to C30 heteroarylene group, $Y^1$ and $Y^2$ are independently a substituted or unsubstituted C6 to C30 aryl group or a substituted or unsubstituted C2 to C30 heterocyclic group, $R^{15}$ to $R^{20}$ are independently hydrogen, deuterium, a substituted or unsubstituted C1 to C10 alkyl group, a substituted or unsubstituted C6 to C30 aryl group, a substituted or unsubstituted C2 to C30 heterocyclic group, a cyano group, or a combination thereof, and m is one of integers of 0 to 2.

The second compound may be used in the light emitting layer together with the first compound to improve mobility and charge stability of charges, thereby improving luminous efficiency and life-span characteristics.

For example, Chemical Formula 2 may include one of the structures of Group II.

[Group II]

C-1

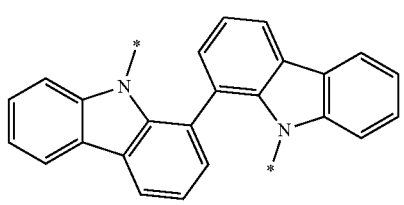

C-2

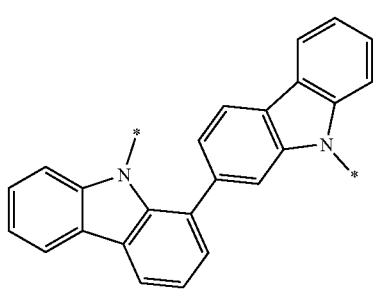

A composition for an organic optoelectronic diode according to another embodiment includes the aforementioned compound (hereinafter, "a first compound"), and a second compound represented by Chemical Formula 2.

-continued
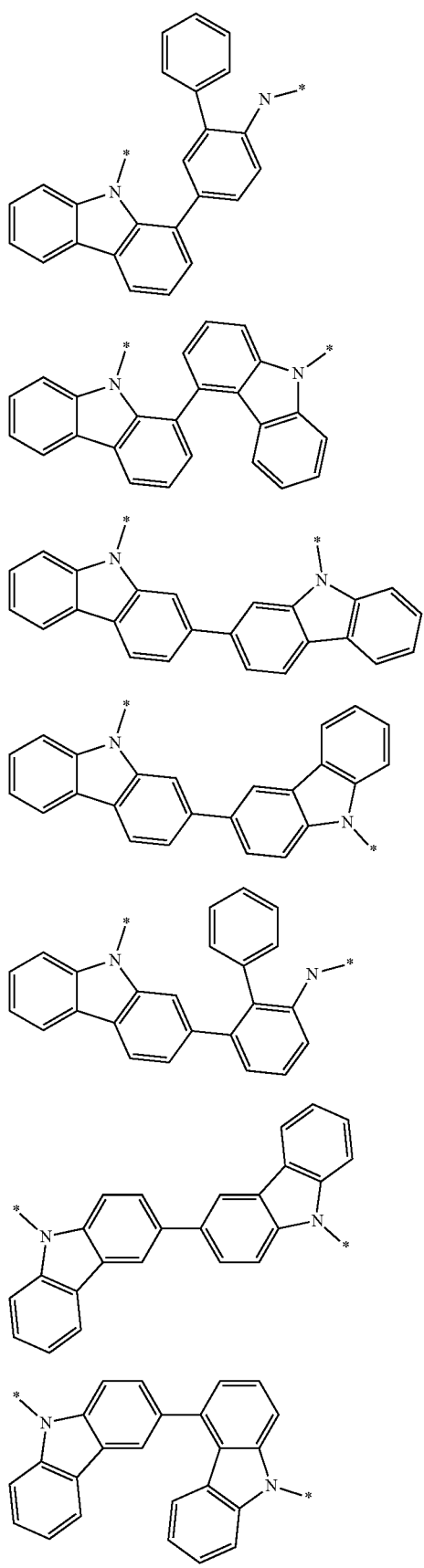
C-3
C-4
C-5
C-6
C-7
C-8
C-9
-continued
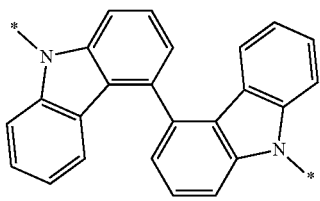
C-10
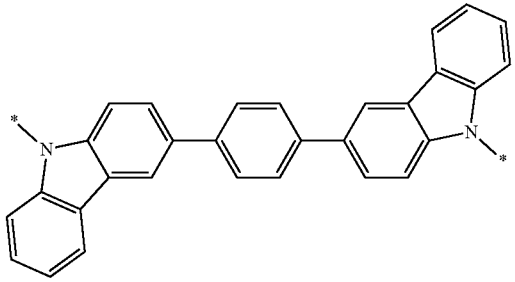
C-11
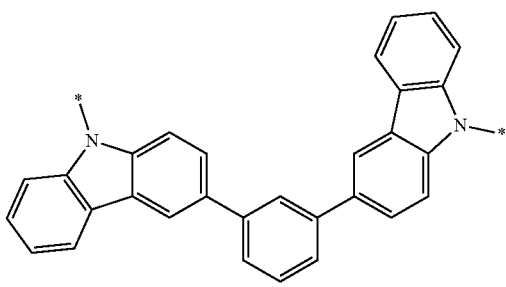
C-12
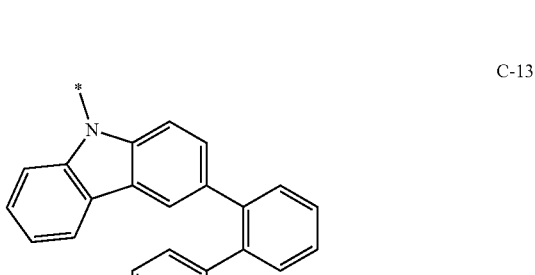
C-13
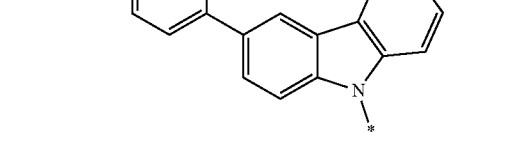
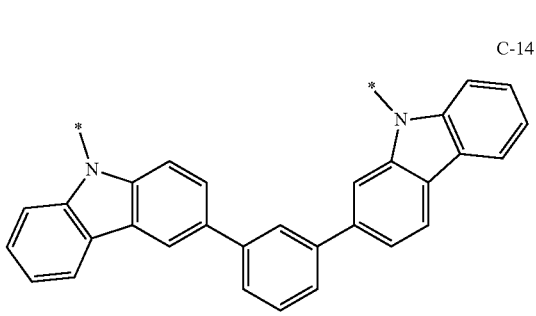
C-14

-continued

C-15
C-16
C-17
C-18

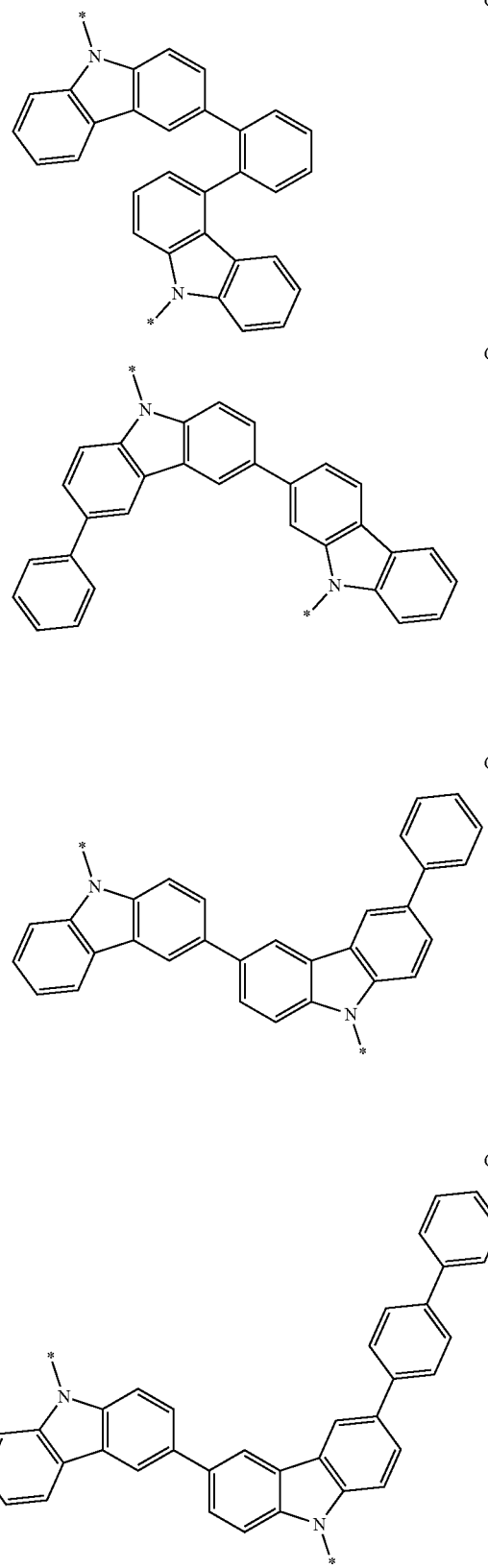

For example, Chemical Formula 2 may be represented by Chemical Formula 2-1 or Chemical Formula 2-2.

[Chemical Formula 2-1]

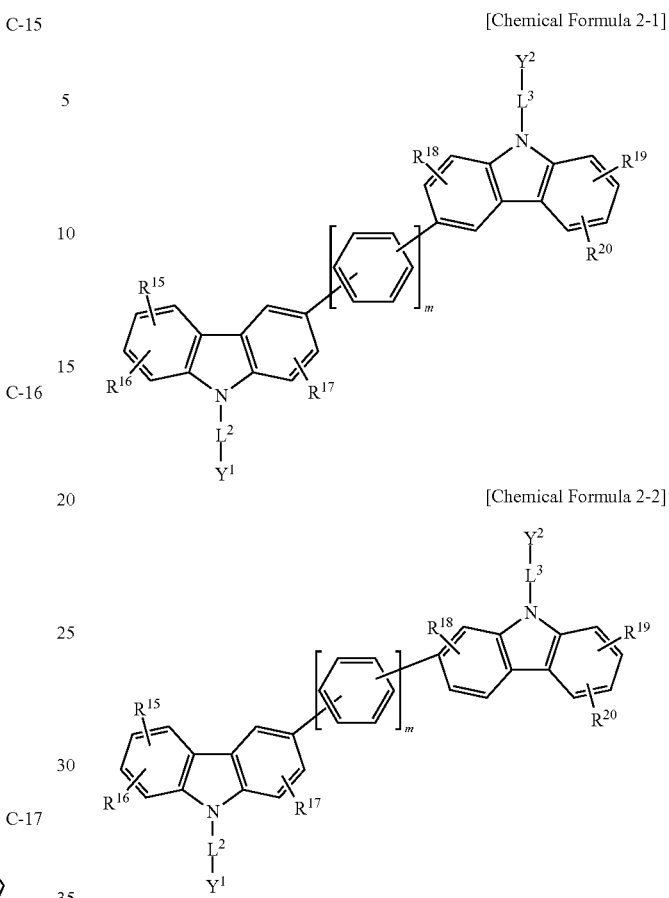

[Chemical Formula 2-2]

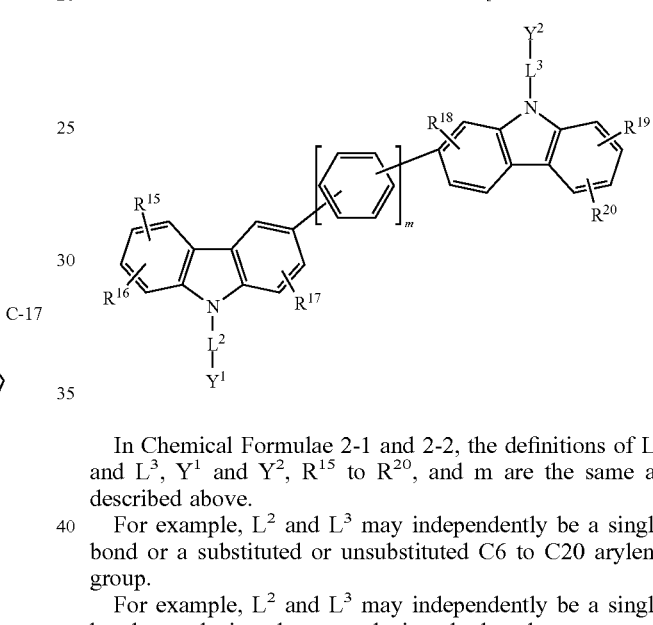

In Chemical Formulae 2-1 and 2-2, the definitions of $L^2$ and $L^3$, $Y^1$ and $Y^2$, $R^{15}$ to $R^{20}$, and m are the same as described above.

For example, $L^2$ and $L^3$ may independently be a single bond or a substituted or unsubstituted C6 to C20 arylene group.

For example, $L^2$ and $L^3$ may independently be a single bond, a substituted or unsubstituted phenylene group, a substituted or unsubstituted biphenylene group, a substituted or unsubstituted terphenylene group, or a substituted or unsubstituted naphthylene group.

For example, $L^2$ and $L^3$ may independently be a single bond, a substituted or unsubstituted m-phenylene group, a substituted or unsubstituted p-phenylene group, a substituted or unsubstituted o-phenylene group, a substituted or unsubstituted m-biphenylene group, a substituted or unsubstituted p-biphenylene group, a substituted or unsubstituted o-biphenylene group, a substituted or unsubstituted m-terphenylene group, a substituted or unsubstituted p-terphenylene group, or a substituted or unsubstituted o-terphenylene group. Herein, "substituted" may for example refer to replacement of at least one hydrogen by deuterium, a C1 to C20 alkyl group, a C6 to C20 aryl group, a halogen, a cyano group, or a combination thereof, but is not limited thereto.

For example, $Y^1$ and $Y^2$ may independently be a substituted or unsubstituted C6 to C30 aryl group.

For example, $Y^1$ and $Y^2$ may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, or a combination thereof.

For example, $Y^1$ and $Y^2$ may independently be a substituted or unsubstituted phenyl group, a substituted or unsubstituted m-biphenyl group, a substituted or unsubstituted p-biphenyl group, a substituted or unsubstituted o-biphenyl group, a substituted or unsubstituted naphthyl group, or a combination thereof.

For example, $*-L^2-Y^1$ and $*-L^3-Y^2$ may independently be one of substituents of Group III, but are not limited thereto.

[Group III]

B-1

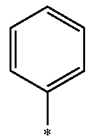

B-2

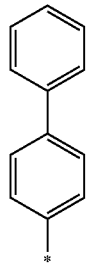

B-3

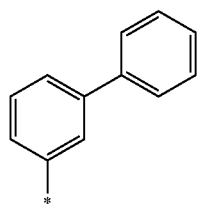

B-4

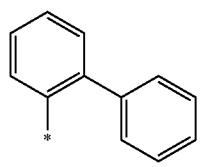

B-5

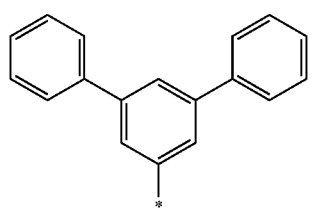

B-6

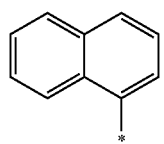

B-7

B-8

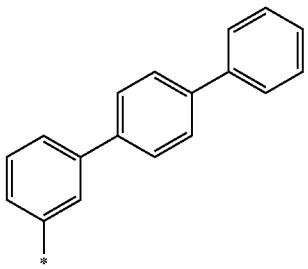

B-9

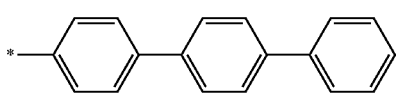

B-10

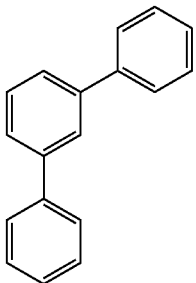

For example, the compound represented by Chemical Formula 2 may be one selected from compounds of Group 2 below, but is not limited thereto.

[Group 2]

[C-1]

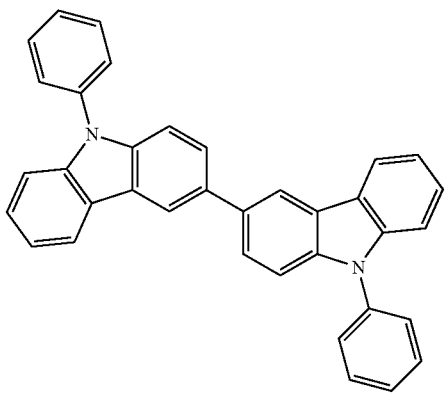

[C-2]
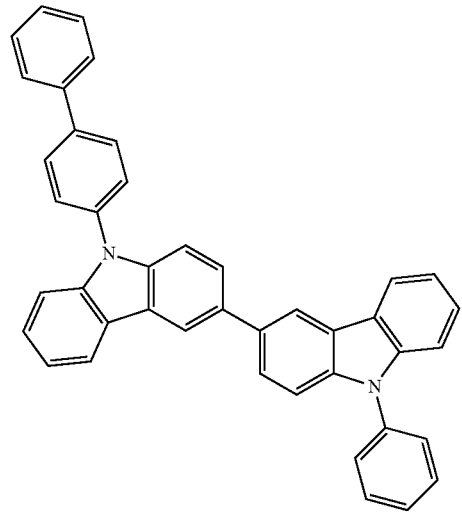
[C-3]
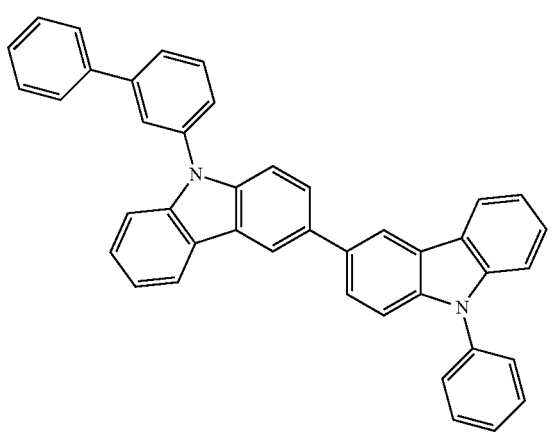
[C-4]
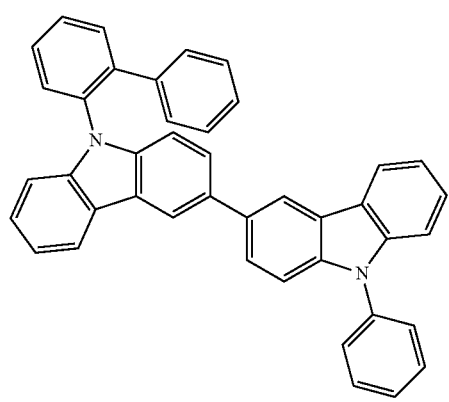
[C-5]
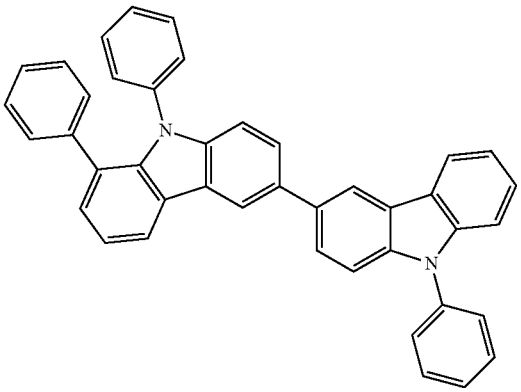
[C-6]
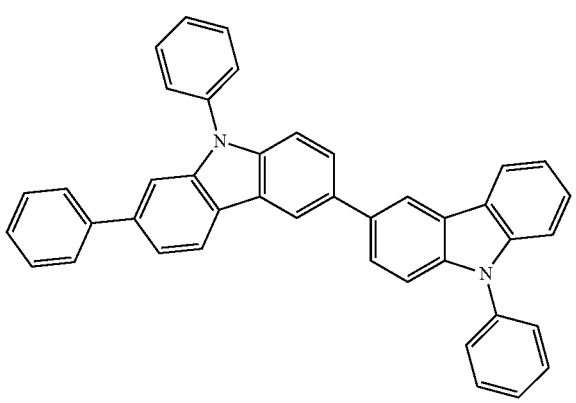
[C-7]
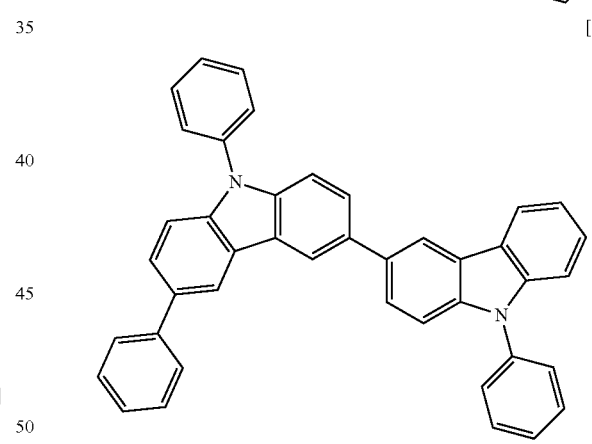
[C-8]
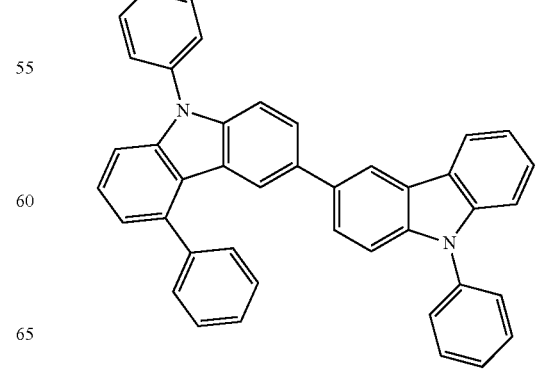

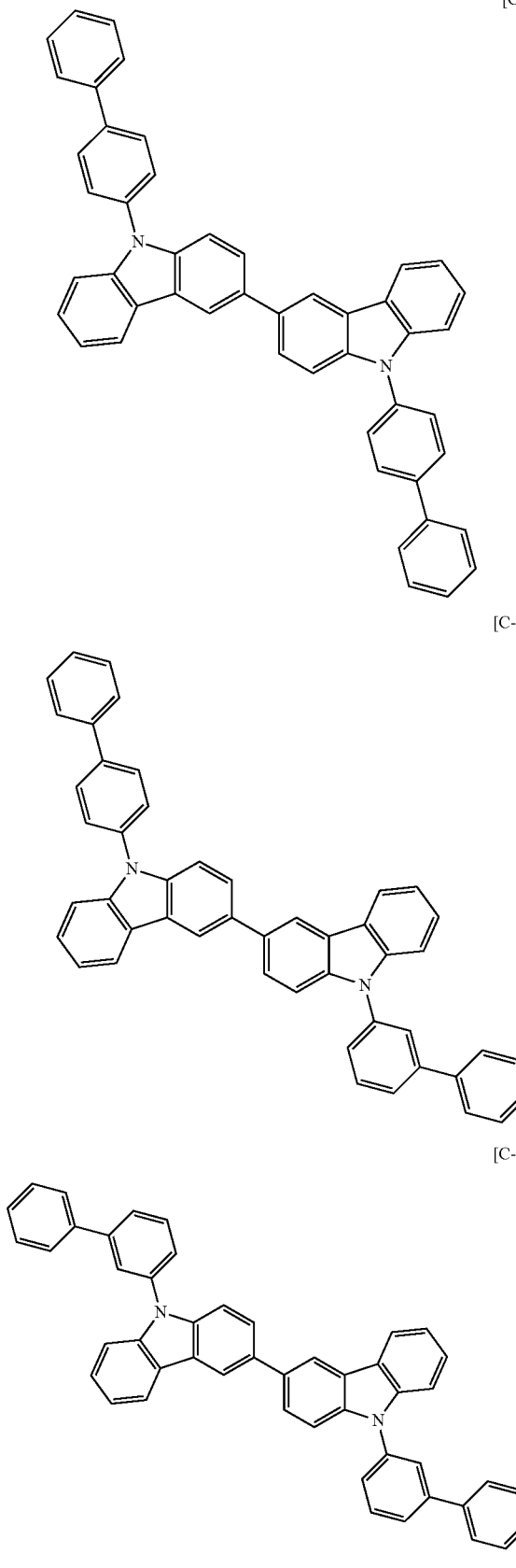
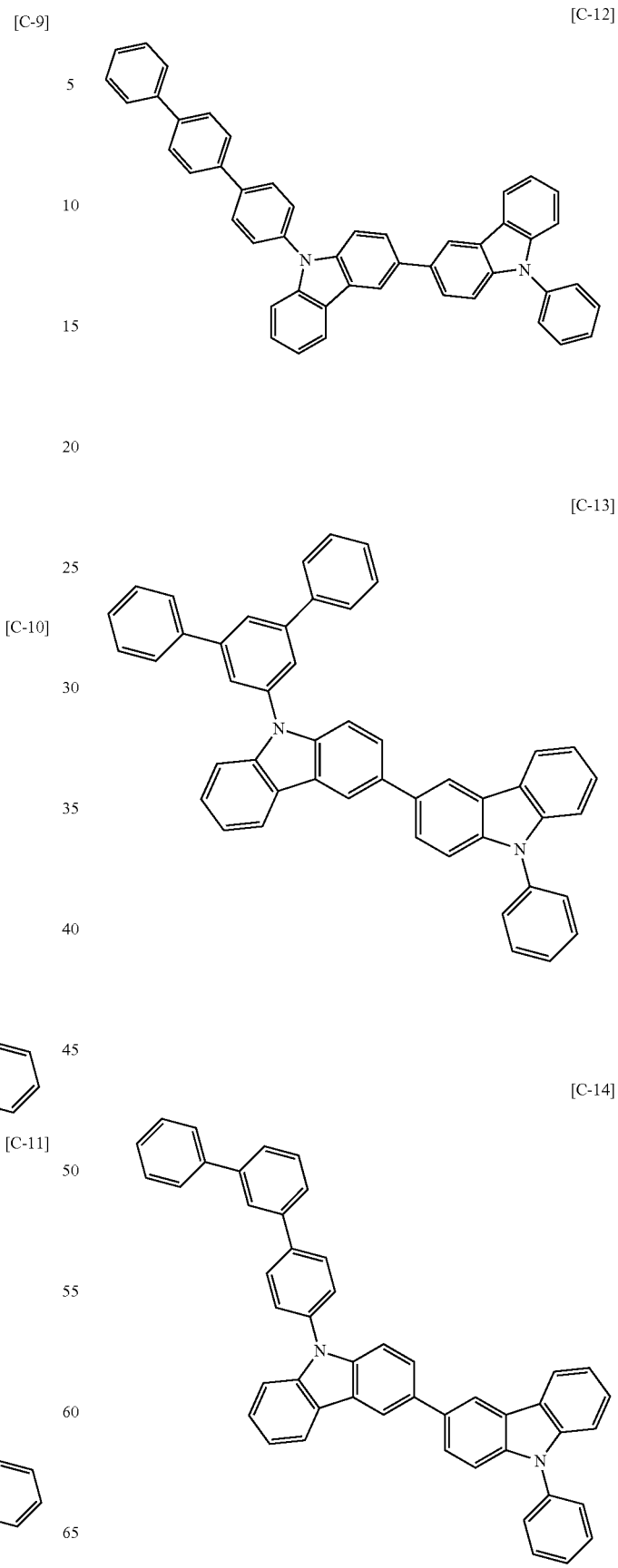

[C-15]
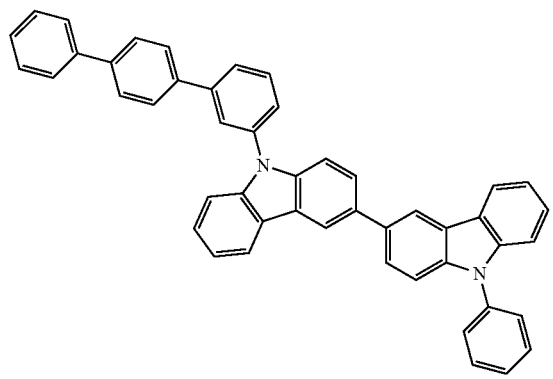
[C-18]
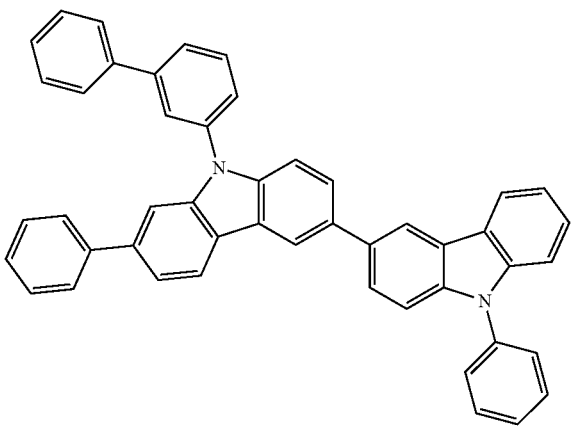
[C-16]
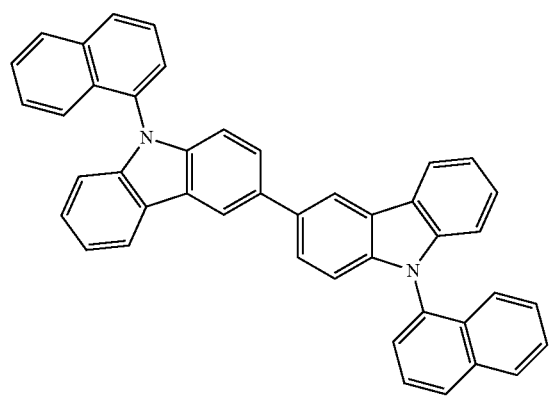
[C-19]
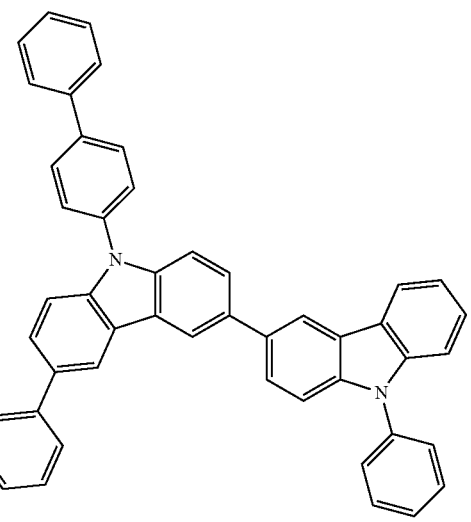
[C-17]
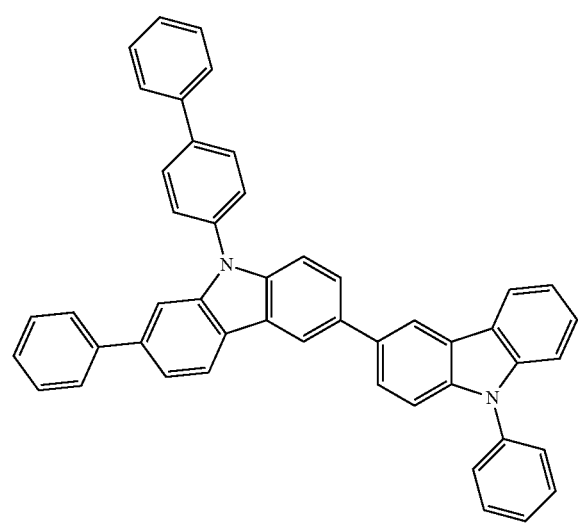
[C-20]
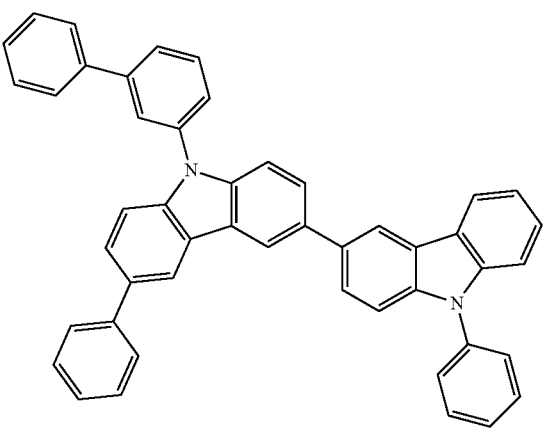

[C-21]
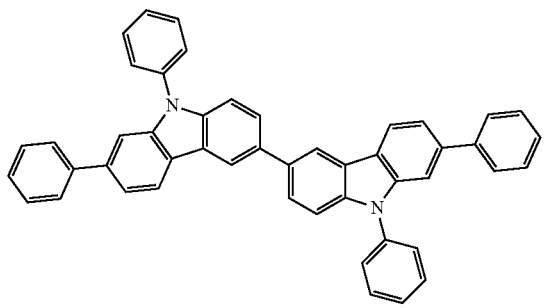
[C-22]
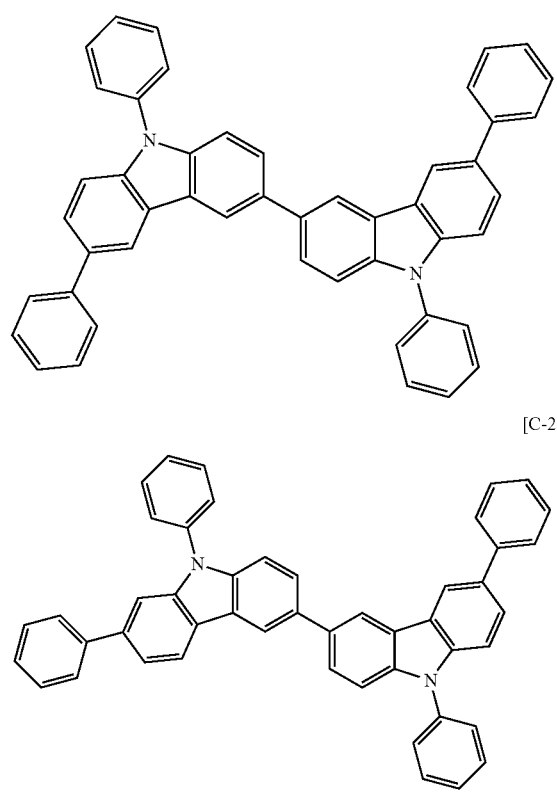
[C-23]
[C24]
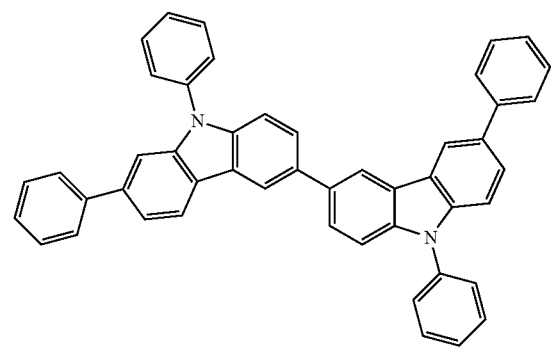
[C-25]
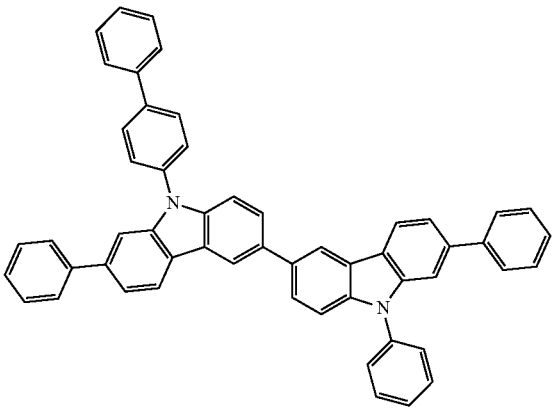
[C-26]
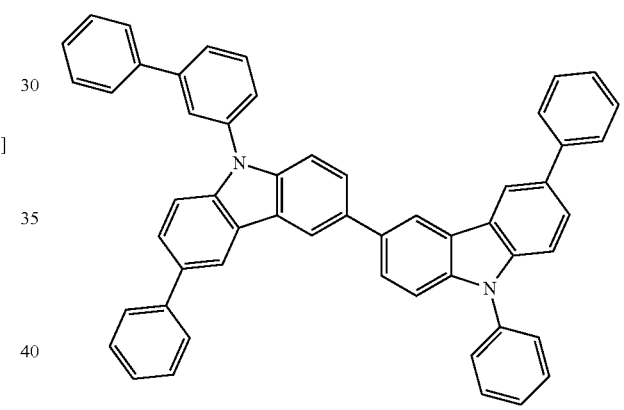
[C-27]
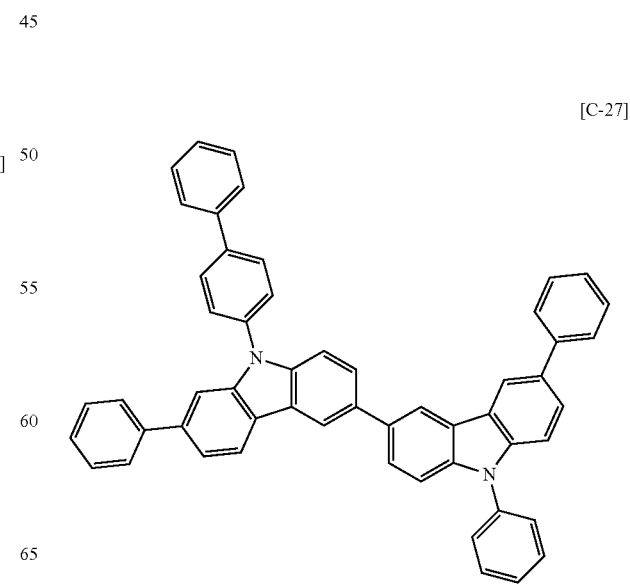

[C-28]
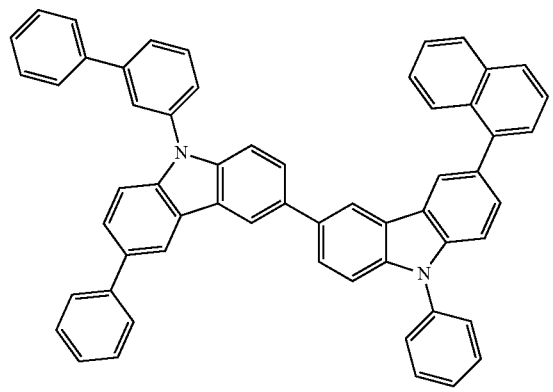
[C-31]
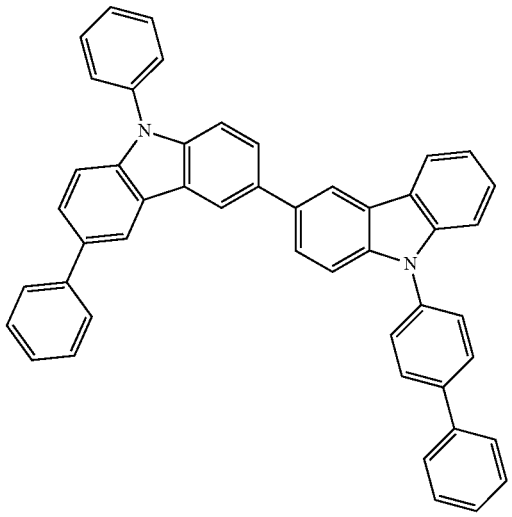
[C-29]
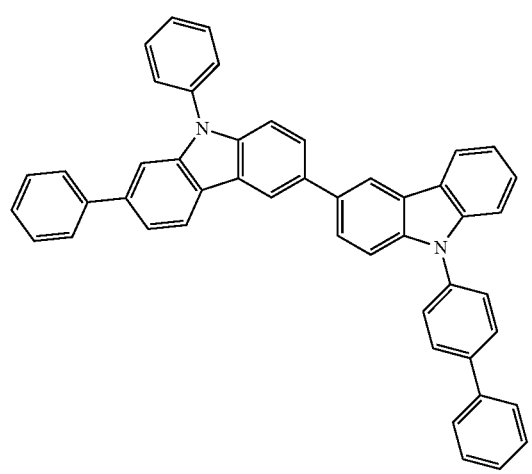
[C-32]
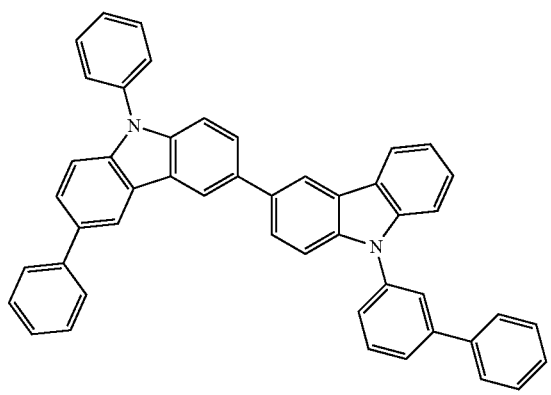
[C-30]
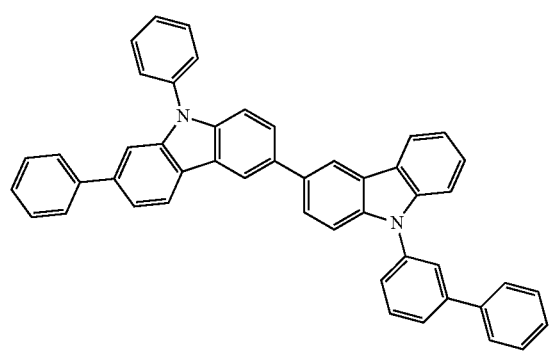
[C-33]
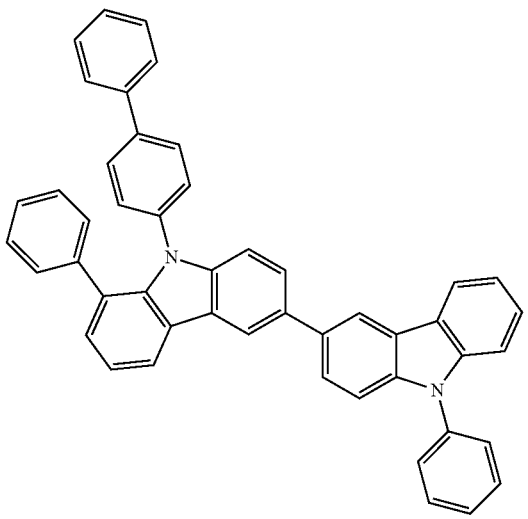

[C-34]
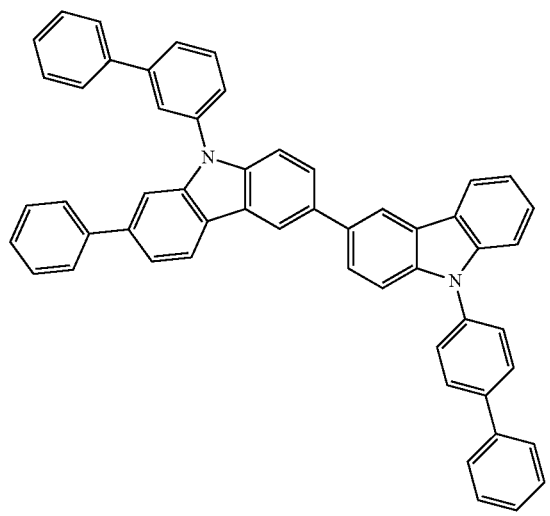
[C-35]
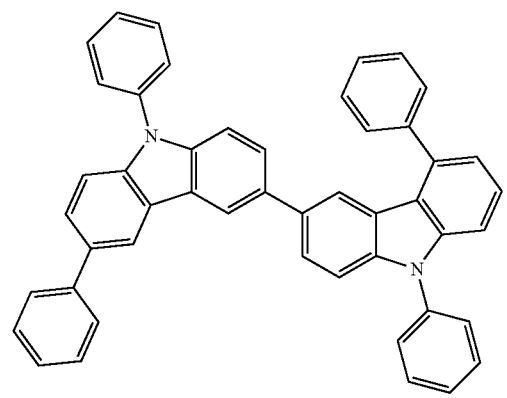
[C-36]
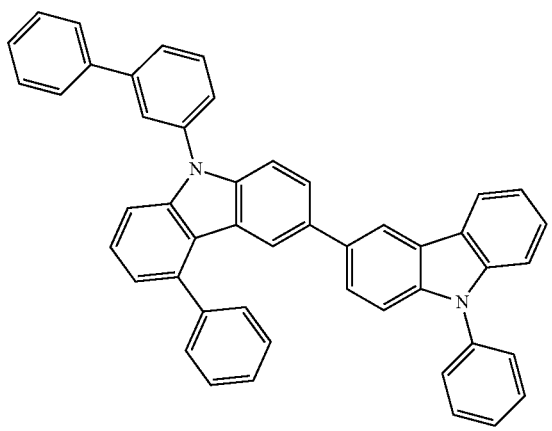
[C-37]
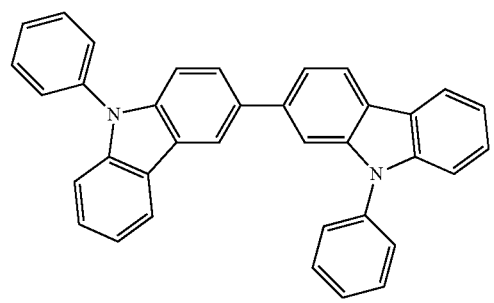
[C-38]
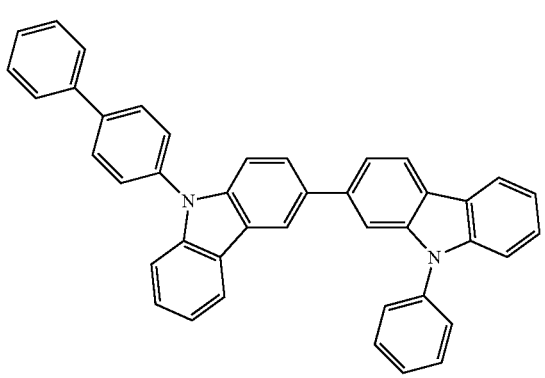
[C-39]
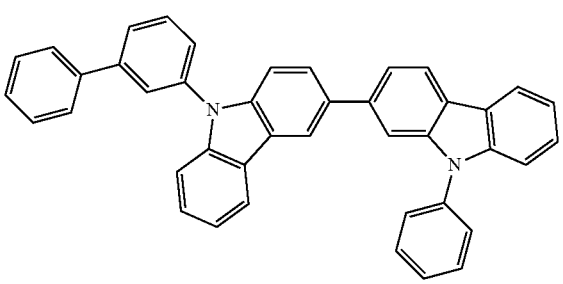
[C-40]
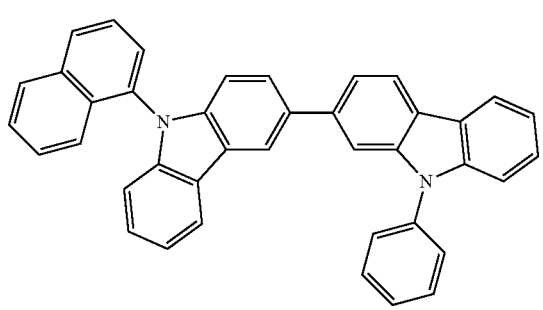

-continued
[C-41]
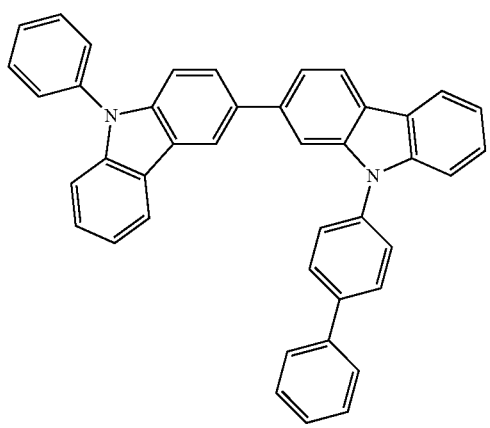
[C-42]
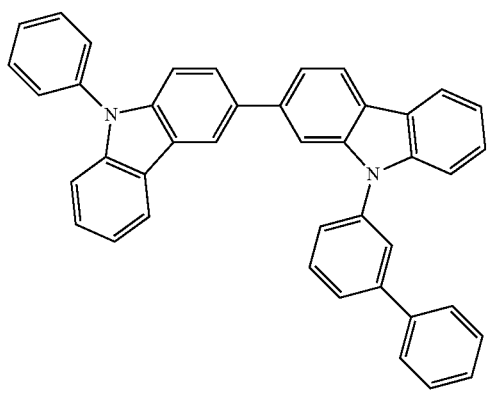
[C-43]
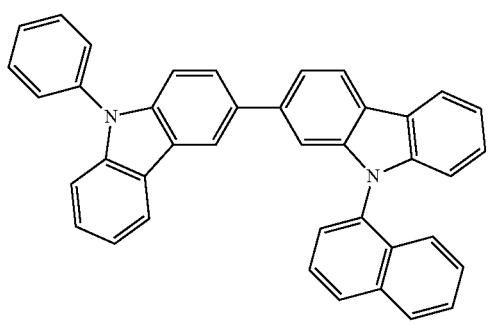
[C-44]
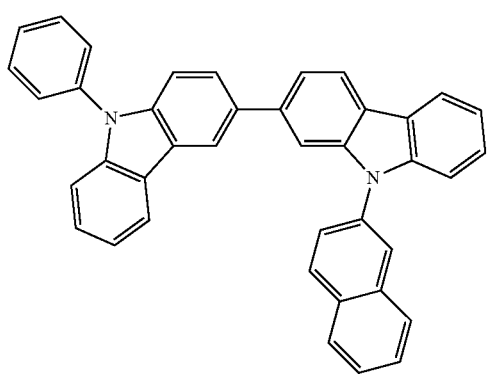
[C-45]
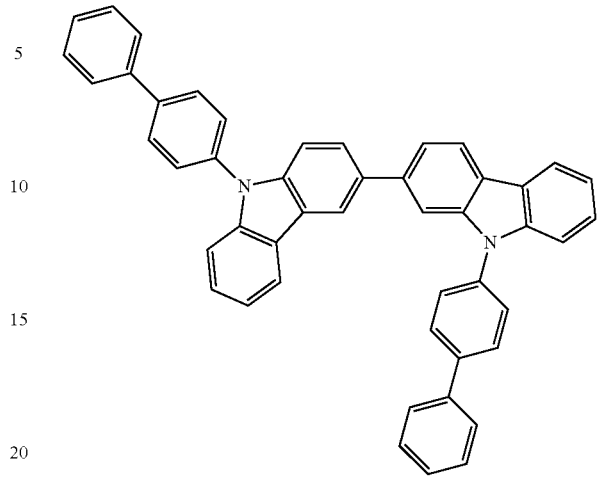
[C-46]
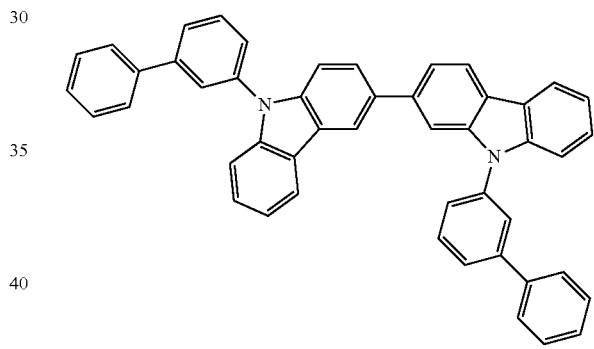
[C-47]
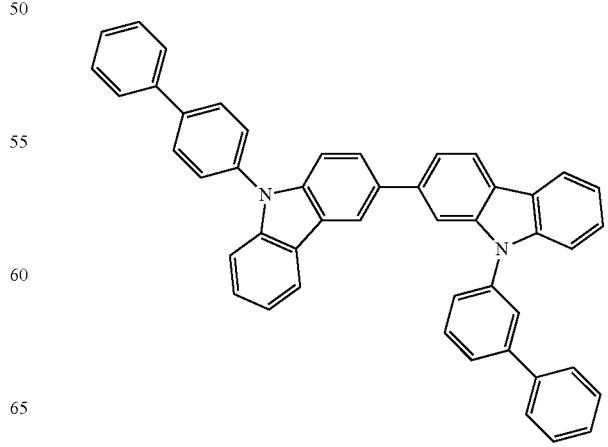

[C-48]
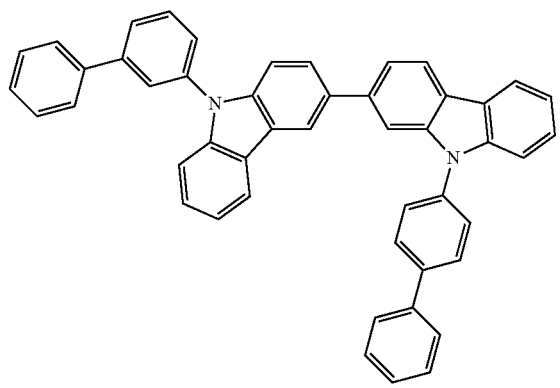
[C-49]
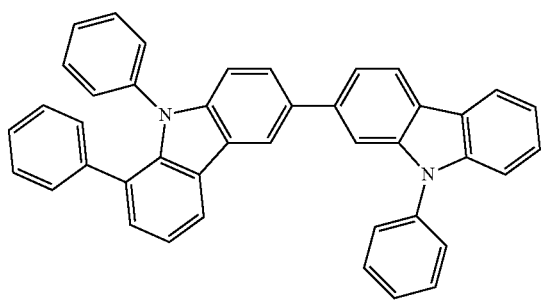
[C-50]
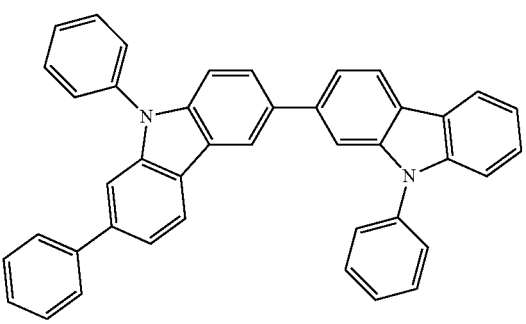
[C-51]
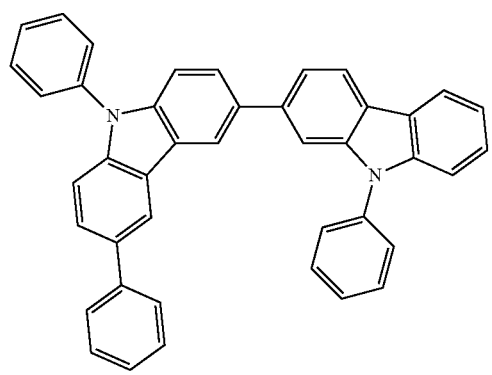
[C-52]
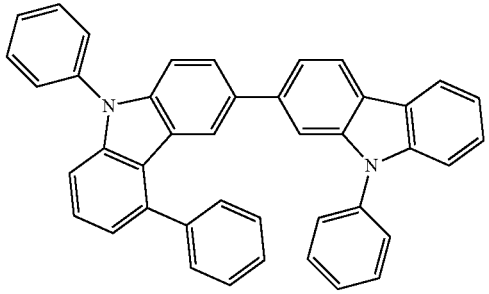
[C-53]
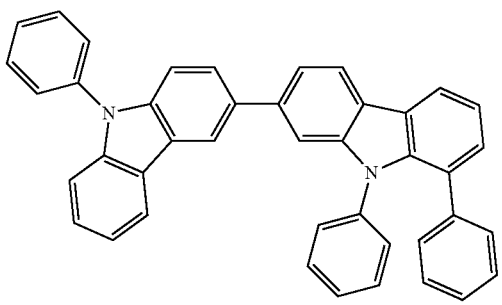
[C-54]
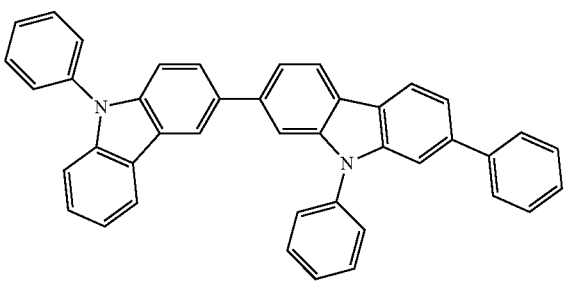
[C-55]
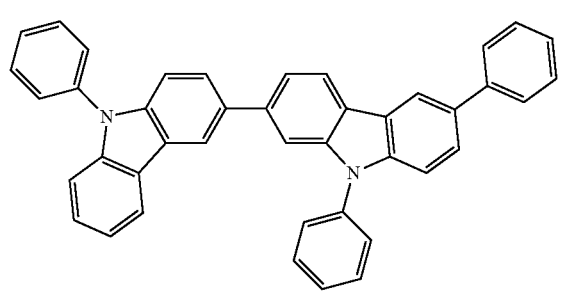
[C-56]

For example, the composition may include a first compound represented by one of Chemical Formula 1-1 to Chemical Formula 1-3 and a second compound represented by Chemical Formula 2-1.

The first compound and the second compound may be, for example, included in a weight ratio of 1:99 to 99:1. Within the above range, bipolar properties may be implemented by matching an appropriate weight ratio using electron transport capability of the first compound and the hole transport capability of the second compound, to improve efficiency and life-span. Within this range, for example, they may be included in a weight ratio of about 10:90 to 90:10, about 20:80 to 80:20, for example, about 20:80 to about 70:30, about 20:80 to about 60:40, and about 20:80 to about 50:50. For example, they may be included in a weight ratio of 20:80 to 40:60, and as a specific example, they may be included in a weight ratio of 20:80, 30:70, or 40:60.

For example, the aforementioned compound or composition may be a host.

The aforementioned compounds may further include one or more compounds.

The aforementioned composition may further include at least one compound in addition to the aforementioned first compound and second compound.

The aforementioned compound or composition may further include a dopant. The dopant may be, for example, a phosphorescent dopant, for example, a red, green or blue phosphorescent dopant, for example, a red or green phosphorescent dopant.

The dopant is a material mixed with the aforementioned compound for the organic optoelectronic diode in a small amount to cause light emission and generally a material such as a metal complex that emits light by multiple excitation into a triplet or more. The dopant may be, for example an inorganic, organic, or organic/inorganic compound, and one or more types thereof may be used.

Examples of the dopant may be a phosphorescent dopant and examples of the phosphorescent dopant may be an organometal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$L^4MX$                      [Chemical Formula Z]

In Chemical Formula Z, M is a metal, $L^4$ and X are the same or different and are a ligand to form a complex compound with M.

The M may be for example Ir, Pt, Os, Ti, Zr, Hf, Eu, Tb, Tm, Fe, Co, Ni, Ru, Rh, Pd, or a combination thereof and $L^4$ and X may be for example a bidendate ligand.

The compound or composition may be formed by a dry film formation method such as chemical vapor deposition (CVD).

Hereinafter, an organic optoelectronic diode including the aforementioned compound or composition is described.

The organic optoelectronic diode may be any device to convert electrical energy into photoenergy and vice versa without particular limitation, and may be for example an organic photoelectric device, an organic light emitting diode, an organic solar cell, and an organic photo conductor drum.

Herein, an organic light emitting diode as one example of an organic optoelectronic diode is described referring to drawings.

FIGS. 1 and 2 are cross-sectional views showing organic light emitting diodes according to embodiments.

Referring to FIG. 1, an organic light emitting diode 100 according to an embodiment includes an anode 120 and a cathode 110 facing each other and an organic layer 105 disposed between the anode 120 and the cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal such as magnesium, calcium, sodium, potassium, titanium, indium, yttrium, lithium, gadolinium, aluminum silver, tin, lead, cesium, barium, and the like or an alloy thereof; a multi-layer structure material such as LiF/Al, $LiO_2$/Al, LiF/Ca, LiF/Al, and $BaF_2$/Ca, but is not limited thereto.

The organic layer 105 may include a light emitting layer 30 including the aforementioned compound or composition.

The light emitting layer 130 may include, for example, the aforementioned compound or composition.

For example, the aforementioned compound represented by Chemical Formula 1 or the composition including the compound represented by Chemical Formula 1 and the compound represented by Chemical Formula 2 may be included as a host in the light emitting layer.

Referring to FIG. 2, an organic light emitting diode 200 further includes a hole auxiliary layer 140 in addition to the light emitting layer 130. The hole auxiliary layer 140 further increases hole injection and/or hole mobility and blocks electrons between the anode 120 and the light emitting layer 130. The hole auxiliary layer 140 may be, for example, a hole transport layer, a hole injection layer, and/or an electron blocking layer and may include at least one layer.

In addition, in an embodiment of the present invention, the organic light emitting diode may further include an electron transport layer, an electron injection layer, and a hole injection layer as the organic layer 105 in FIG. 1 or 2.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

Hereinafter, the embodiments are illustrated in more detail with reference to examples. However, these examples are exemplary, and the present scope is not limited thereto.

Hereinafter, starting materials and reactants used in Examples and Synthesis Examples were purchased from Sigma-Aldrich Co. Ltd., TCI Inc., Tokyo Chemical Industry, or P&H Tech as far as there in no particular comment or were synthesized by known methods.

(Preparation of Compound for Organic Optoelectronic Diode)

The compound as one specific examples of the present invention was synthesized through the following steps.

(Preparation of First Compound)

Synthesis Example 1: Synthesis of Intermediate I-1

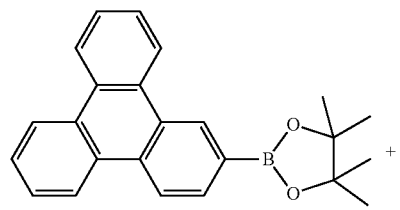

+

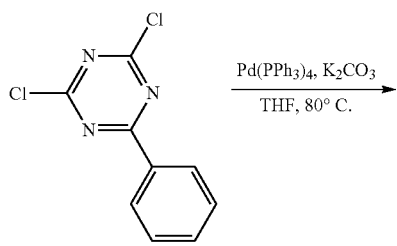

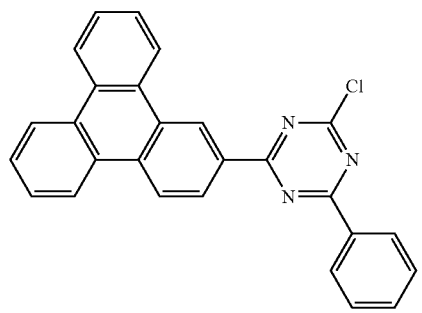

I-1

4,4,5,5-tetramethyl-2-(triphenylen-2-yl)-1,3,2-dioxaborolane (50 g, 141 mmol) was dissolved in 0.5 L of tetrahydrofuran (THF) under a nitrogen environment, and 2,4-dichloro-6-phenyl-1,3,5-triazine (47.9 g, 212 mmol) and tetrakis(triphenylphosphine)palladium (1.63 g, 1.41 mmol) were added thereto and then, stirred. Subsequently, potassium carbonate saturated in water (48.7 g, 353 mmol) was added thereto and then, heated and refluxed at 80° C. for 12 hours. When a reaction was complete, after adding water to the reaction solution, the mixture was extracted with dichloromethane (DCM), treated with anhydrous magnesium sulfate to remove moisture, filtered, and concentrated under a reduced pressure. This obtained residue was separated and purified through flash column chromatography to obtain Intermediate I-1 (40.1 g, 68%).

HRMS (70 eV, EI+): m/z calcd for C27H16ClN3: 417.1033, found: 417.

Elemental Analysis: C, 78%; H, 4%

Synthesis Example 2: Synthesis of Intermediate I-2

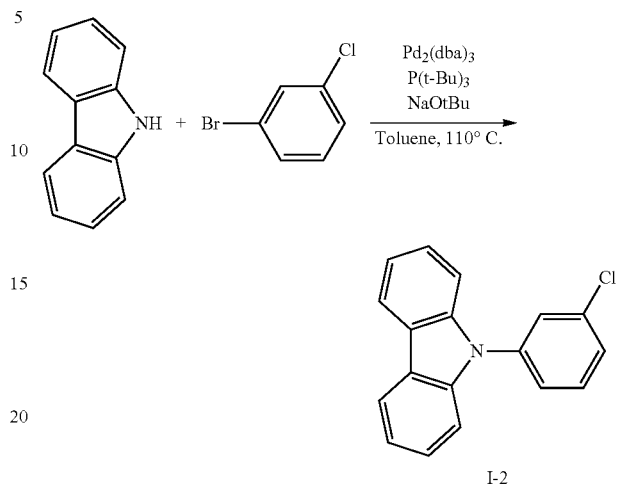

I-2

9H-carbazole (100 g, 598 mmol) was dissolved in 1.0 L of toluene under a nitrogen environment, and 1-bromo-3-chlorobenzene (137 g, 718 mmol), tris(dibenzylideneacetone)dipalladium (0) (5.48 g, 5.98 mmol), tris-tert butylphosphine (0.60 g, 0.30 mmol), and sodium tert-butoxide (69.0 g, 718 mmol) were sequentially added thereto and then, heated and refluxed at 110° C. for 18 hours. When a reaction was complete, after adding water to the reaction solution, the mixture was extracted with dichloromethane (DCM), treated with anhydrous magnesium sulfate to remove moisture, filtered, and concentrated under a reduced pressure. This obtained residue was separated and purified through flash column chromatography to obtain Intermediate I-2 (118 g, 71%).

HRMS (70 eV, EI+): m/z calcd for C18H12ClN: 277.0658, found: 277.

Elemental Analysis: C, 78%; H, 4%

Synthesis Example 3: Synthesis of Intermediate I-3

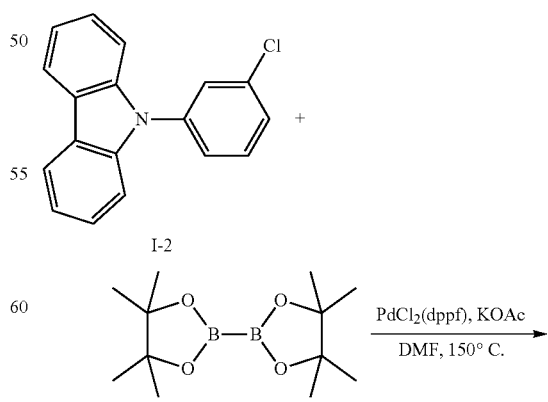

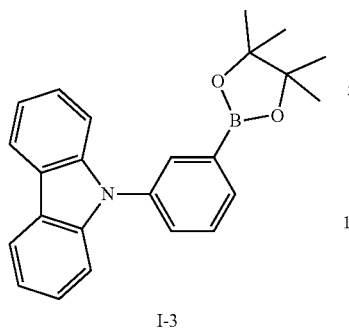

I-3

Intermediate I-2 (100 g, 360 mmol) was dissolved in 1.0 L of dimethylformamide (DMF) under a nitrogen environment, and bis(pinacolato)diboron (110 g, 432 mmol), (1,1'-bis(diphenylphosphine)ferrocene)dichloropalladium (II) (2.94 g, 3.60 mmol), and potassium acetate (106 g, 1,080 mmol) were added thereto and then, heated and refluxed at 150° C. for 20 hours. When a reaction was complete, after adding water to the reaction solution, the mixture was filtered and dried in a vacuum oven. This obtained residue was separated and purified through flash column chromatography to obtain Intermediate I-3 (113 g, 85%).

HRMS (70 eV, EI+): m/z calcd for C24H24BNO2: 369.1900, found: 369.

Elemental Analysis: C, 78%; H, 7%

Synthesis Example 4: Synthesis of Compound 1

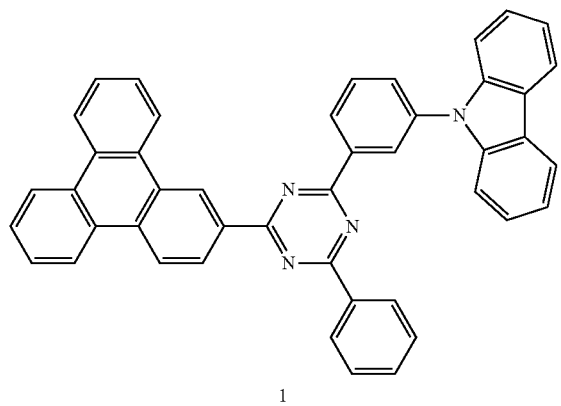

1

Compound 1 (14.6 g, 98%) was obtained according to the same method as Synthesis Example 1 except that Intermediate I-1 (10 g, 23.9 mmol) and Intermediate I-3 (8.83 g, 23.9 mmol) were used.

HRMS (70 eV, EI+): m/z calcd for C45H28N4: 624.2314, found: 624.

Elemental Analysis: C, 87%; H, 5%

Synthesis Example 5: Synthesis of Intermediate I-4

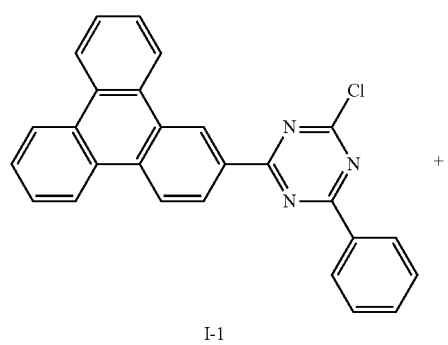

I-1

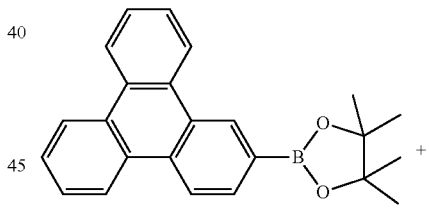

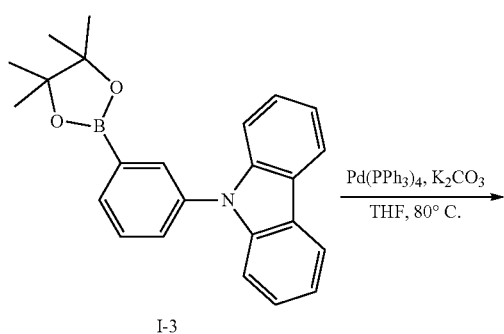

I-3

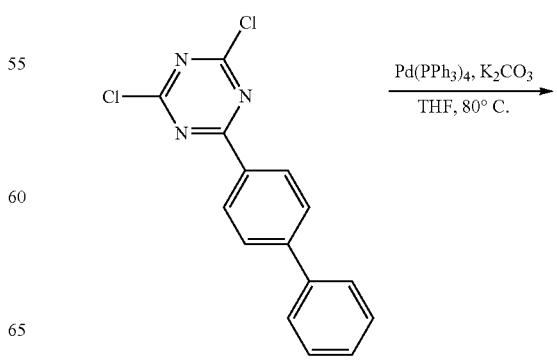

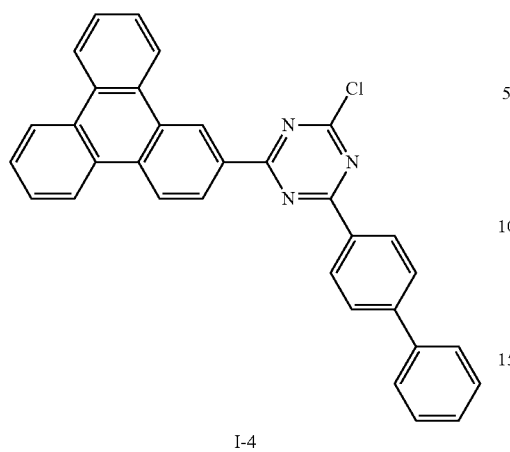

I-4

Intermediate I-4 (46.0 g, 66%) was obtained according to the same method as Synthesis Example 1 except that 4,4,5,5-tetramethyl-2-(triphenylen-2-yl)-1,3,2-dioxaborolane (50 g, 141 mmol) and 2-(biphenyl-4-yl)-4,6-dichloro-1,3,5-triazine (64.0 g, 212 mmol) were used.

HRMS (70 eV, EI+): m/z calcd for C33H20ClN3: 493.1346, found: 493.

Elemental Analysis: C, 80%; H, 4%

Synthesis Example 6: Synthesis of Compound 2

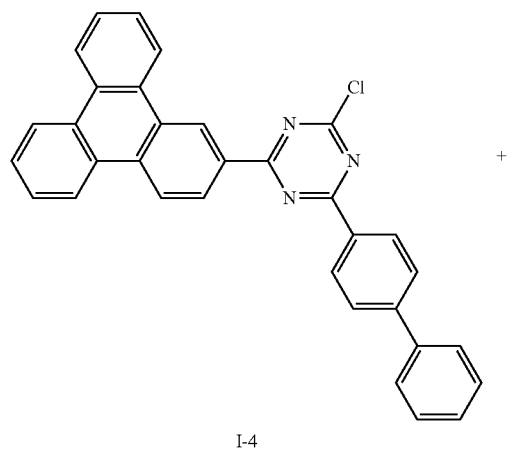

I-4

+

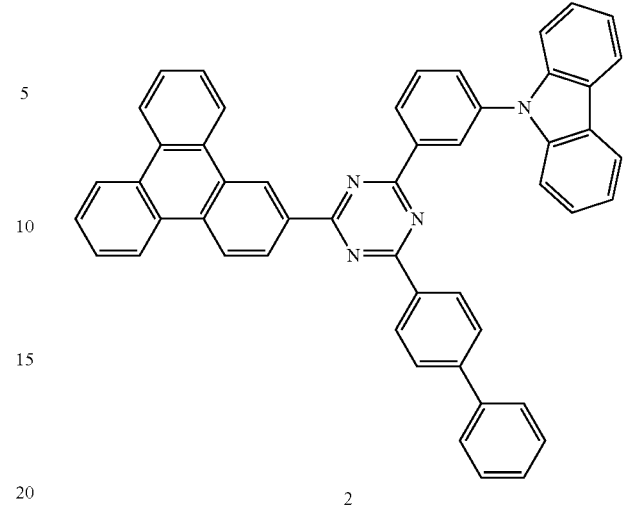

2

Compound 2 (13.4 g, 95%) was obtained according to the same method as Synthesis Example 1 except that Intermediate I-4 (10 g, 20.2 mmol) and Intermediate I-3 (7.48 g, 20.2 mmol) were used.

HRMS (70 eV, EI+): m/z calcd for C51H32N4: 700.2627, found: 700.

Elemental Analysis: C, 87%; H, 5%

Synthesis Example 7: Synthesis of Intermediate I-5

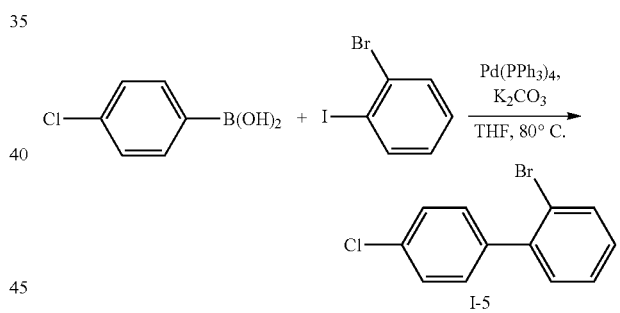

I-5

Intermediate I-5 (152 g, 89%) was obtained according to the same method as Synthesis Example 1 except that 4-chlorophenylboronic acid (100 g, 640 mmol) and 1-bromo-2-iodobenzene (199 g, 703 mmol) were used.

HRMS (70 eV, EI+): m/z calcd for C12H8BrCl: 265.9498, found: 266.

Elemental Analysis: C, 54%; H, 3%

Synthesis Example 8: Synthesis of Intermediate I-6

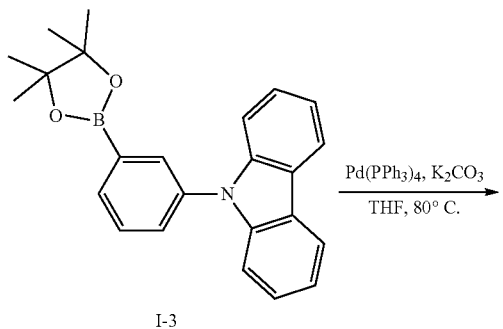

I-5

+

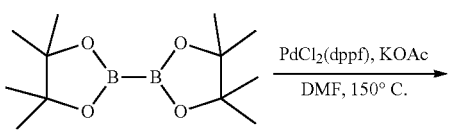

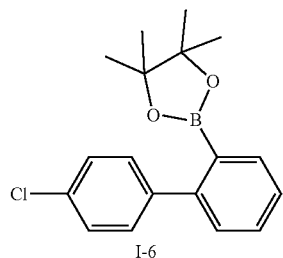

Intermediate I-6 (135 g, 90%) was obtained according to the same method as Synthesis Example 3 except that Intermediate I-5 (150 g, 477 mmol) was used.

HRMS (70 eV, EI+): m/z calcd for $C_{18}H_{20}BClO_2$: 314.1245, found: 314.

Elemental Analysis: C, 69%; H, 6%

Synthesis Example 9: Synthesis of Intermediate I-7

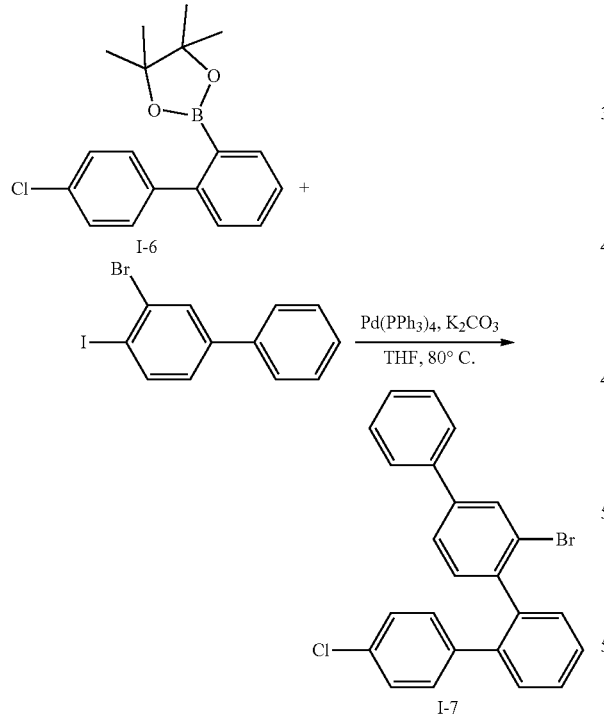

Intermediate I-7 (161 g, 93%) was obtained according to the same method as Synthesis Example 1 except that Intermediate I-6 (130 g, 413 mmol) and 3-bromo-4-iodobiphenyl (163 g, 455 mmol) were used.

HRMS (70 eV, EI+): m/z calcd for $C_{24}H_{16}BrCl$: 418.0124, found: 418.

Elemental Analysis: C, 69%; H, 4%

Synthesis Example 10: Synthesis of Intermediate I-8

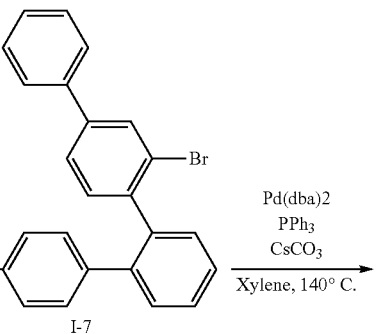

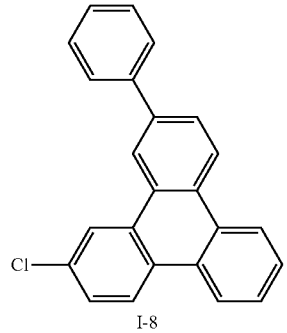

Intermediate I-7 (155 g, 369 mmol) was dissolved in 0.5 L of xylene under a nitrogen environment, and bis(dibenzylideneacetone)palladium (0) (6.37 g, 11.1 mmol), triphenylphosphine (9.67 g, 36.9 mmol), and cesium carbonate (120 g, 369 mmol) were added thereto and then, heated and refluxed at 140° C. for 27 hours. When a reaction was complete, after adding water to the reaction solution, the mixture was extracted with dichloromethane (DCM), treated with anhydrous magnesium sulfate to remove moisture, filtered, and concentrated under a reduced pressure. This obtained residue was separated and purified through flash column chromatography to obtain Intermediate I-8 (87.5 g, 70%).

HRMS (70 eV, EI+): m/z calcd for $C_{24}H_{15}Cl$: 338.0862, found: 338.

Elemental Analysis: C, 85%; H, 5%

Synthesis Example 11: Synthesis of Intermediate I-9

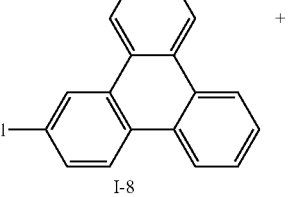

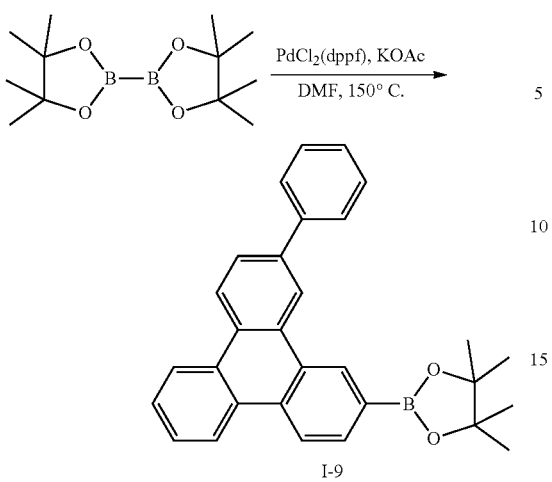

Intermediate I-9 (67.0 g, 66%) was obtained according to the same method as Synthesis Example 3 except that Intermediate I-8 (80 g, 236 mmol) was used.

HRMS (70 eV, EI+): m/z calcd for C30H27BO2: 430.2104, found: 430.

Elemental Analysis: C, 84%; H, 6%

Synthesis Example 12: Synthesis of Intermediate I-10

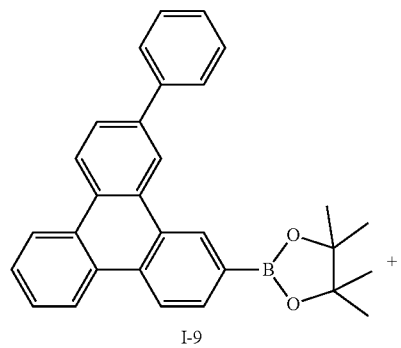

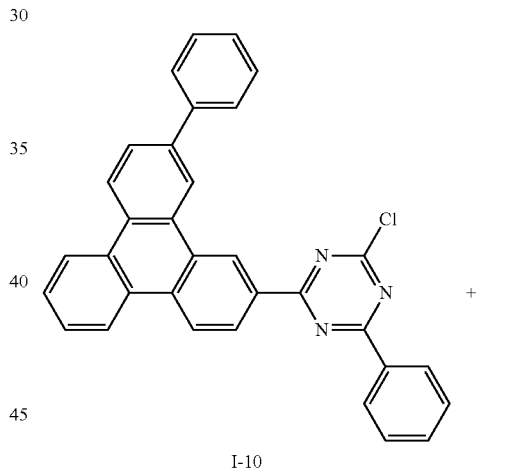

Intermediate I-10 (40.1 g, 70%) was obtained according to the same method as Synthesis Example 1 except that Intermediate I-9 (50 g, 116 mmol) and 2,4-dichloro-6-phenyl-1,3,5-triazine (39.4 g, 174 mmol) were used HRMS (70 eV, EI+): m/z calcd for C33H20ClN3: 493.1346, found: 493.

Elemental Analysis: C, 80%; H, 4%

Synthesis Example 13: Synthesis of Compound 4

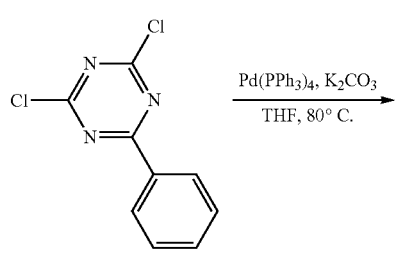

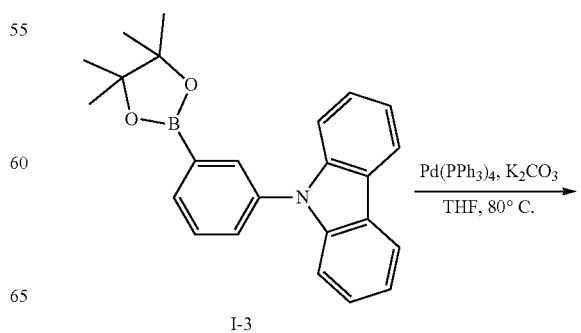

-continued

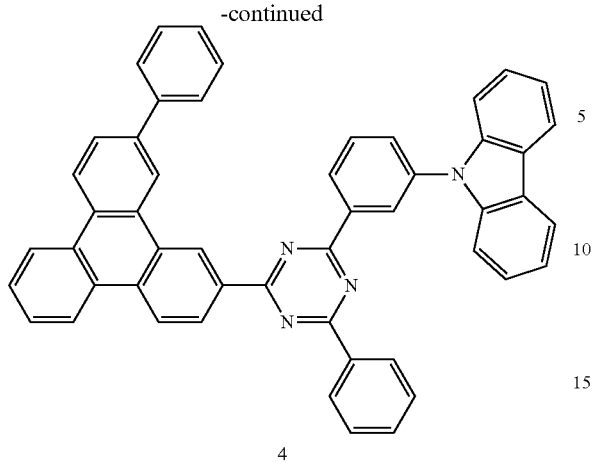

4

Compound 4 (13.6 g, 96%) was obtained according to the same method as Synthesis Example 1 except that Intermediate I-10 (10 g, 20.2 mmol) and Intermediate I-3 (7.48 g, 20.2 mmol) was used.

HRMS (70 eV, EI+): m/z calcd for C51H32N4: 700.2627, found: 700.

Elemental Analysis: C, 87%; H, 5%

Synthesis Example 14: Synthesis of Intermediate I-11

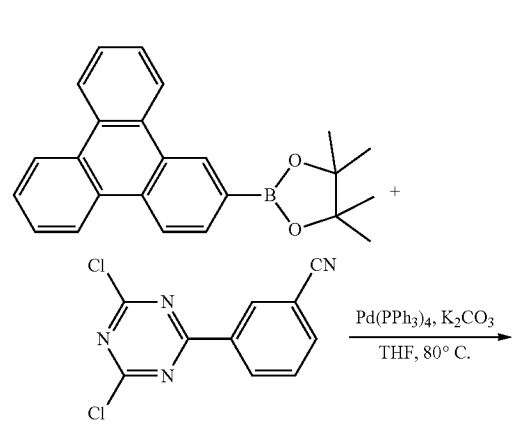

Magnesium (13.3 g, 549 mmol) and iodine (2.79 g, 11.0 mmol) were dissolved in 0.1 L of tetrahydrofuran (THF) under a nitrogen environment and then, stirred for 30 minutes. Subsequently, 3-bromobenzonitrile (100 g, 549 mmol) dissolved in 0.1 L of THF was slowly added thereto for 30 minutes. This obtained Grignard reagent was slowly added to cyanuric chloride (12 g, 659 mmol) dissolved in 1 L of THF for 30 minutes and then, stirred for 3 hours. When a reaction was complete, after adding water to the reaction solution, the mixture was extracted with dichloromethane (DCM), treated with anhydrous magnesium sulfate to remove moisture, filtered, and concentrated under a reduced pressure. This obtained residue was separated and purified through flash column chromatography to obtain Intermediate I-11 (56.5 g, 41%).

HRMS (70 eV, EI+): m/z calcd for C10H4Cl2N4: 249.8913, found: 250.

Elemental Analysis: C, 48%; H, 2%

Synthesis Example 15: Synthesis of Intermediate I-12

Intermediate I-12 (30.0 g, 48%) was obtained according to the same method as Synthesis Example 1 except that 4,4,5,5-tetramethyl-2-(triphenylen-2-yl)-1,3,2-dioxaborolane (50 g, 141 mmol) and Intermediate I-11 (53.1 g, 212 mmol) were used.

HRMS (70 eV, EI+): m/z calcd for C28H15ClN4: 442.0985, found: 442.

Elemental Analysis: C, 76%; H, 3%

Synthesis Example 16: Synthesis of Compound 11

-continued

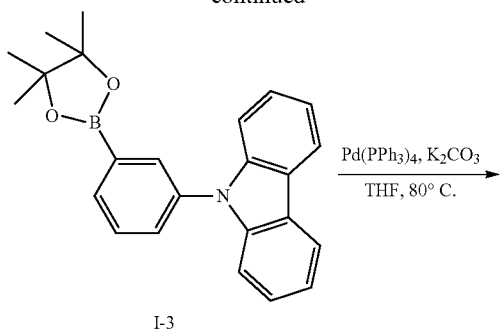

Compound 11 (11.16 g, 76%) was obtained according to the same method as Synthesis Example 1 except that Intermediate I-12 (10 g, 22.6 mmol) and Intermediate I-3 (8.34 g, 22.6 mmol) were used.

HRMS (70 eV, EI+): m/z calcd for C46H27N5: 649.2266, found: 649.

Elemental Analysis: C, 85%; H, 4%

Synthesis Example 17: Synthesis of Intermediate I-13

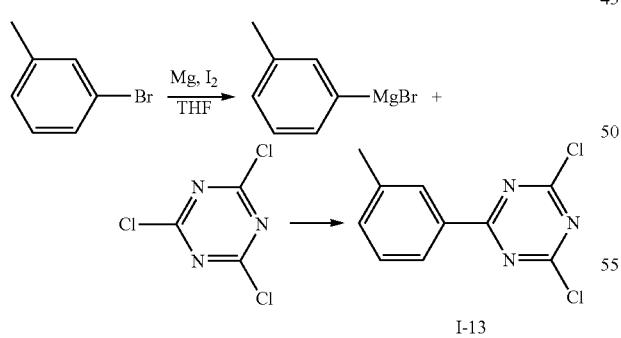

Intermediate I-13 (92.7 g, 66%) was obtained according to the same method as Synthesis Example 14 except that 3-bromotoluene (100 g, 585 mmol) and cyanuric chloride (129 g, 702 mmol) were used.

HRMS (70 eV, EI+): m/z calcd for C10H7Cl2N3: 239.0017, found: 239.

Elemental Analysis: C, 50%; H, 3%

Synthesis Example 18: Synthesis of Intermediate I-14

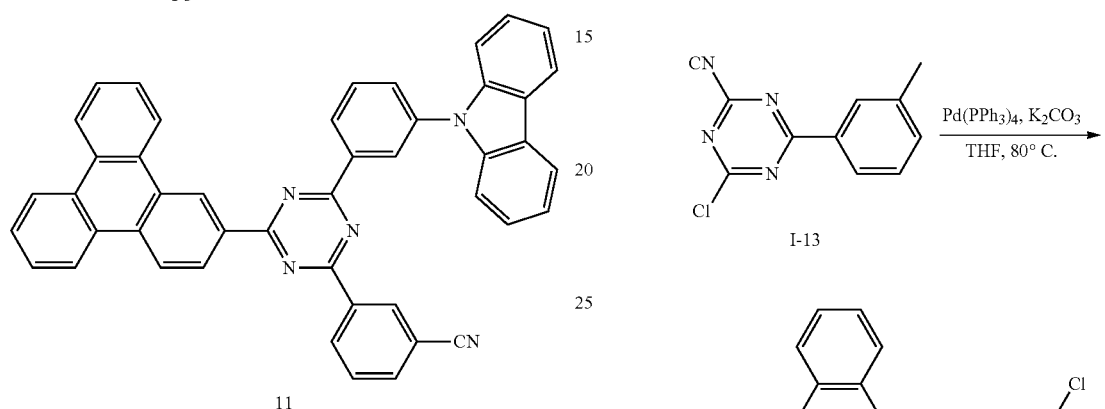

Intermediate I-14 (42.6 g, 70%) was obtained according to the same method as Synthesis Example 1 except that 4,4,5,5-tetramethyl-2-(triphenylen-2-yl)-1,3,2-dioxaborolane (50 g, 141 mmol) and Intermediate I-13 (33.9 g, 212 mmol) were used.

HRMS (70 eV, EI+): m/z calcd for C28H18ClN3: 431.1189, found: 431.

Elemental Analysis: C, 78%; H, 4%

Synthesis Example 19: Synthesis of Compound 15

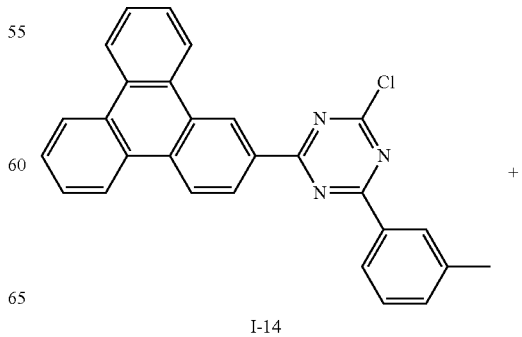

-continued

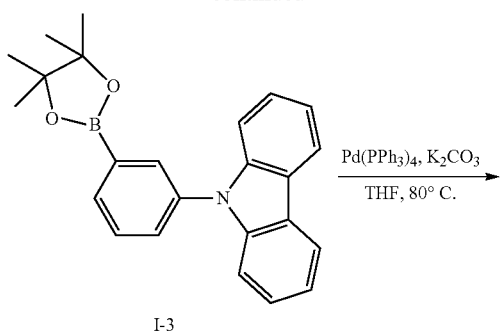
I-3

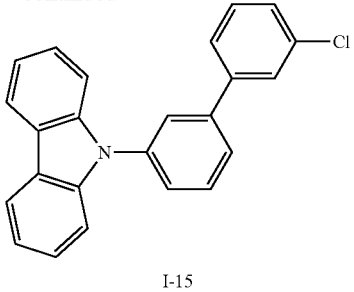
I-15

Intermediate I-15 (42.5 g, 89%) was obtained according to the same method as Synthesis Example 1 except that Intermediate I-3 (50 g, 135 mmol) and 1-bromo-3-chlorobenzene (28.5 g, 149 mmol) were used.

HRMS (70 eV, EI+): m/z calcd for $C_{24}H_{16}ClN$: 353.0971, found: 353.

Elemental Analysis: C, 81%; H, 5%

Synthesis Example 21: Synthesis of Intermediate I-16

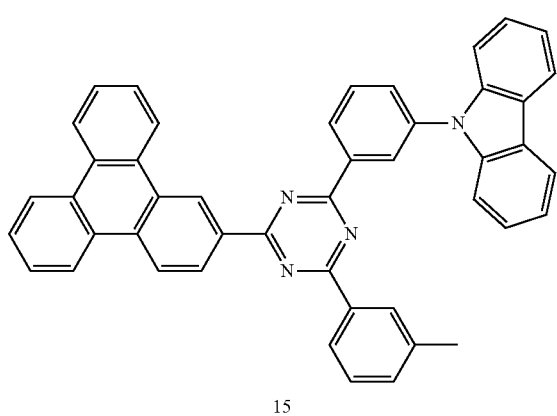
15

Compound 15 (13.3 g, 90%) was obtained according to the same method as Synthesis Example 1 except that Intermediate I-14 (10 g, 23.2 mmol) and Intermediate I-3 (8.55 g, 23.2 mmol) were used.

HRMS (70 eV, EI+): m/z calcd for $C_{46}H_{30}N_4$: 638.2470, found: 638.

Elemental Analysis: C, 86%; H, 5%

Synthesis Example 20: Synthesis of Intermediate I-15

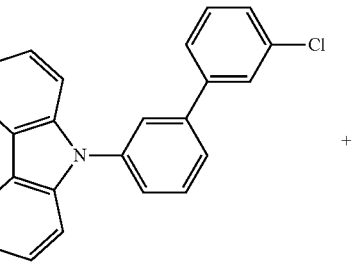
I-15

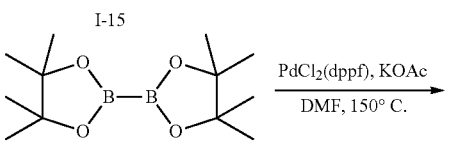

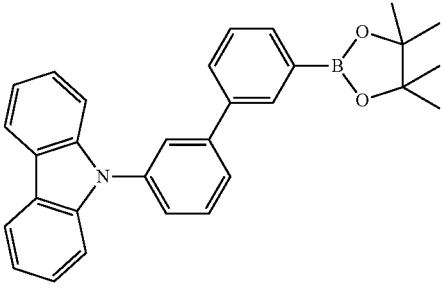
I-16

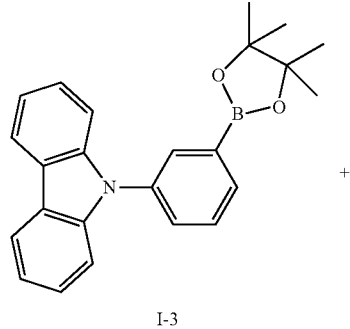
I-3

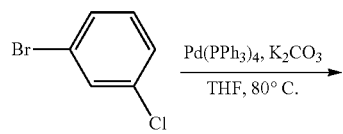

Intermediate I-16 (31.2 g, 62%) was obtained according to the same method as Synthesis Example 3 except that Intermediate I-15 (40 g, 113 mmol) was used.

HRMS (70 eV, EI+): m/z calcd for $C_{30}H_{28}BNO_2$: 445.2213, found: 445.

Elemental Analysis: C, 81%; H, 6%

Synthesis Example 22: Synthesis of Compound 20

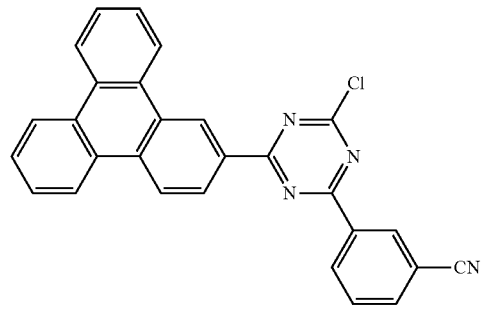
I-1

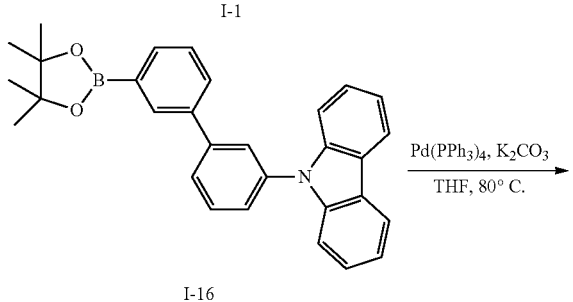
I-16

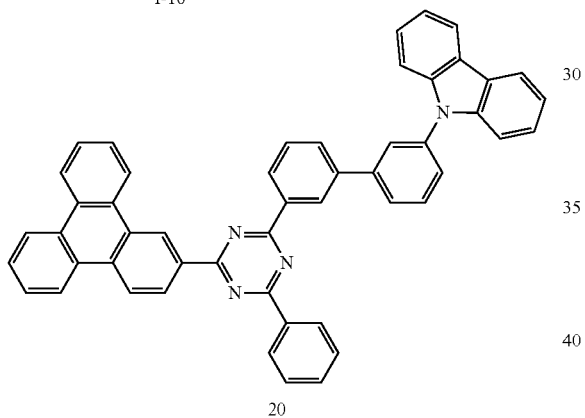
20

Compound 20 (15.9 g, 95%) was obtained according to the same method as Synthesis Example 1 except that Intermediate I-1 (10 g, 23.9 mmol) and Intermediate I-16 (10.6 g, 23.9 mmol) were used.

HRMS (70 eV, EI+): m/z calcd for C51H32N4: 700.2627, found: 700.

Elemental Analysis: C, 87%; H, 5%

Synthesis Example 23: Synthesis of Intermediate I-17

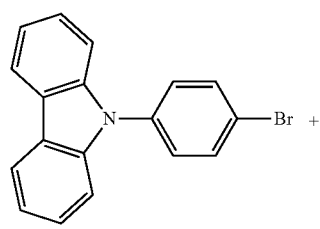

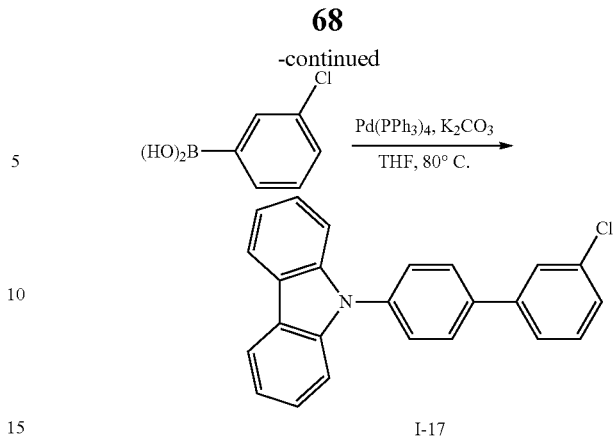
I-17

Intermediate I-17 (50.5 g, 92%) was obtained according to the same method as Synthesis Example 1 except that 9-(4-bromophenyl)carbazole (50 g, 155 mmol) purchased from Tokyo Chemical Industry Co., Ltd. and chlorophenyl boronic acid (26.7 g, 171 mmol) were used.

HRMS (70 eV, EI+): m/z calcd for C24H16ClN: 353.0971, found: 353.

Elemental Analysis: C, 81%; H, 5%

Synthesis Example 24: Synthesis of Intermediate I-18

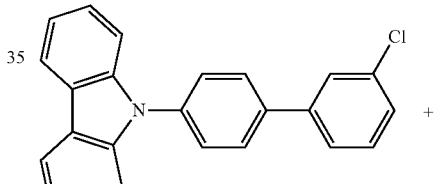
I-17

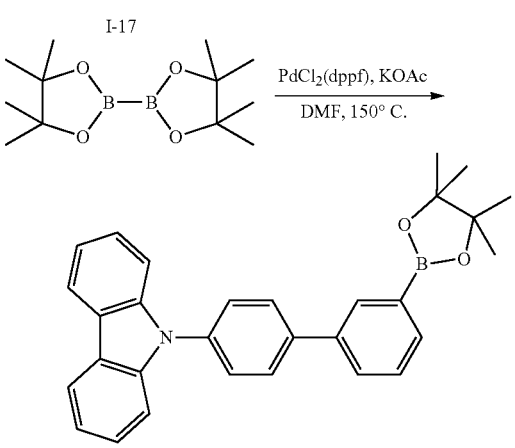
I-18

Intermediate I-18 (41.9 g, 74%) was obtained according to the same method as Synthesis Example 3 except that Intermediate I-17 (45 g, 127 mmol) was used.

HRMS (70 eV, EI+): m/z calcd for C30H28BNO2: 445.2213, found: 445.

Elemental Analysis: C, 81%; H, 6%

Synthesis Example 25: Synthesis of Compound 22

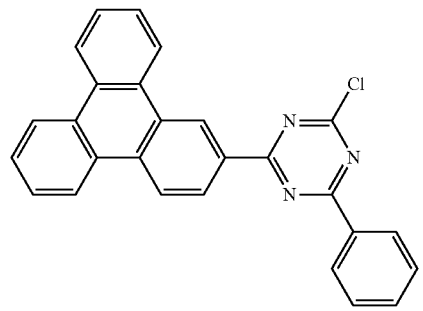

I-1

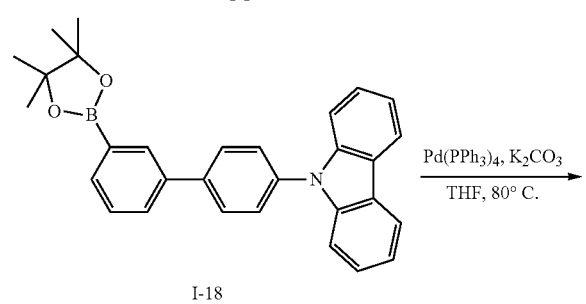

I-18

Pd(PPh₃)₄, K₂CO₃
THF, 80° C.

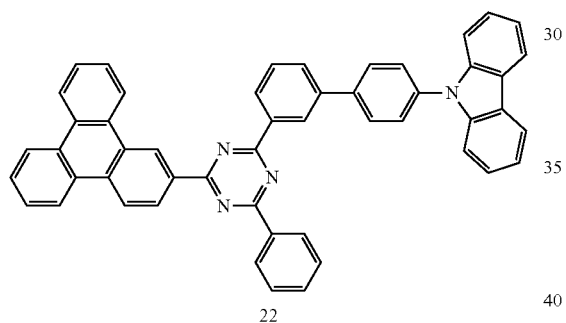

22

Compound 22 (15.4 g, 92%) was obtained according to the same method as Synthesis Example 1 except that Intermediate I-1 (10 g, 23.9 mmol) and Intermediate I-18 (10.6 g, 23.9 mmol) were used.

HRMS (70 eV, EI+): m/z calcd for $C_{51}H_{32}N_4$: 700.2627, found: 700.

Elemental Analysis: C, 87%; H, 5%

Synthesis Example 26: Synthesis of Intermediate I-19

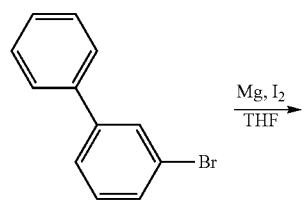

Mg, I₂
THF

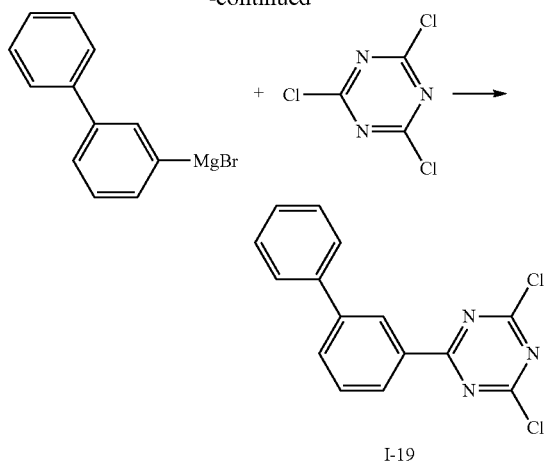

I-19

Intermediate I-19 (92.0 g, 71%) was obtained according to the same method as Synthesis Example 14 except that 3-bromobiphenyl (100 g, 429 mmol) and cyanuric chloride (94.9 g, 515 mmol) were used.

HRMS (70 eV, EI+): m/z calcd for $C_{15}H_9Cl_2N_3$: 301.0174, found: 301.

Elemental Analysis: C, 60%; H, 3%

Synthesis Example 27: Synthesis of Intermediate I-20

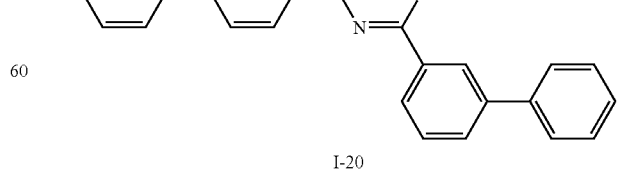

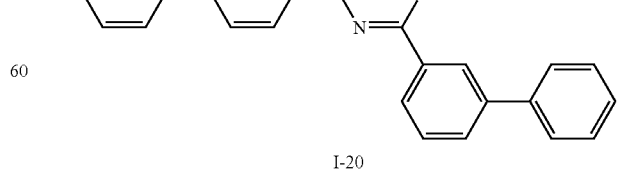

I-20

Intermediate I-20 (43.9 g, 63%) was obtained according to the same method as Synthesis Example 1 except that 4,4,5,5-tetramethyl-2-(triphenylen-2-yl)-1,3,2-dioxaborolane (50 g, 141 mmol) and Intermediate I-19 (64.1 g, 212 mmol) were used.

HRMS (70 eV, EI+): m/z calcd for C33H20ClN3: 493.1346, found: 493.

Elemental Analysis: C, 80%; H, 4%

Comparative Synthesis Example 1: Synthesis of Compound Host1

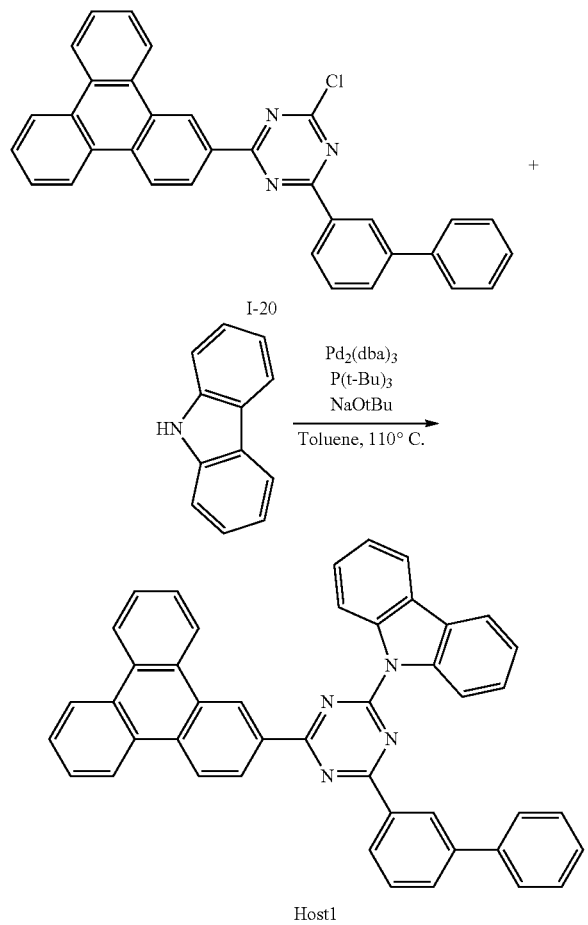

Host1

Compound Host 1 (12.4 g, 98%) was obtained according to the same method as Synthesis Example 2 except that Intermediate I-20 (10 g, 20.2 mmol) and carbazole (3.72 g, 22.3 mmol) were used.

HRMS (70 eV, EI+): m/z calcd for C45H28N4: 624.2314, found: 624.

Elemental Analysis: C, 87%; H, 5%

Comparative Synthesis Example 2: Synthesis of Intermediate I-21

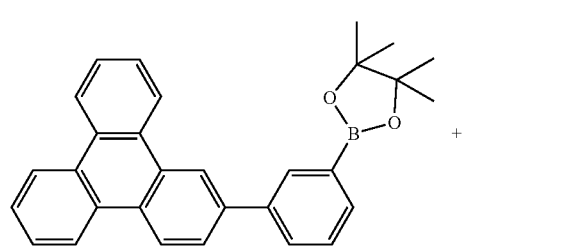

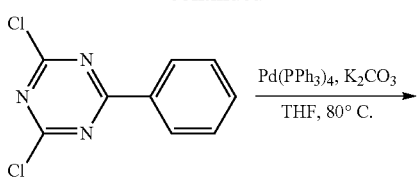

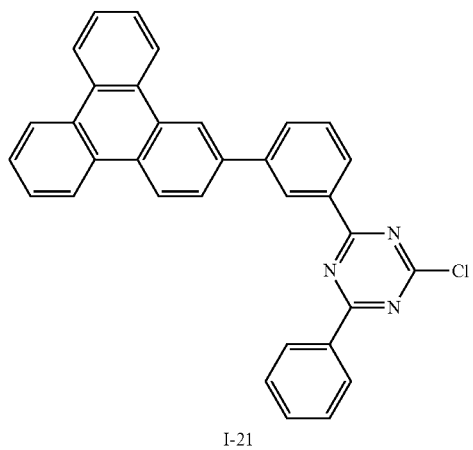

I-21

Intermediate I-21 (37.2 g, 65%) was obtained according to the same method as Synthesis Example 1 except that 4,4,5,5-tetramethyl-2-(3-(triphenylen-2-yl)phenyl)-1,3,2-dioxaborolane (50 g, 116 mmol) and 2,4-dichloro-6-phenyl-1,3,5-triazine (39.4 g, 174 mmol) were used.

HRMS (70 eV, EI+): m/z calcd for C33H20ClN3: 493.1346, found: 493.

Elemental Analysis: C, 80%; H, 4%

Comparative Synthesis Example 3: Synthesis of Compound Host2

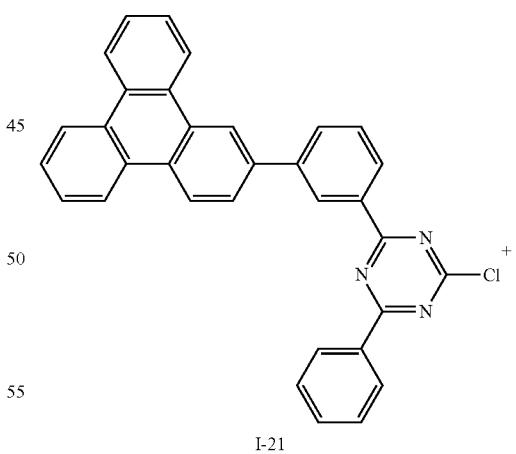

I-21

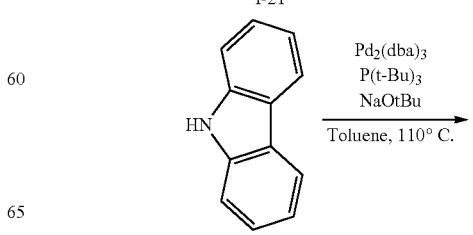

-continued

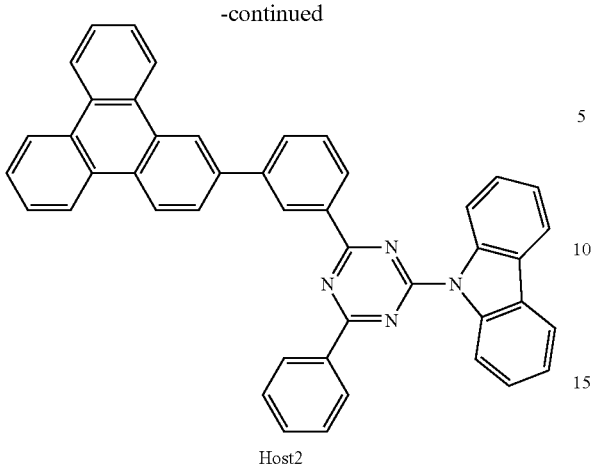

Host2

Compound Host 2 (12.0 g, 95%) was obtained according to the same method as Synthesis Example 2 except that intermediate I-21 (10 g, 20.2 mmol) and carbazole (3.72 g, 22.3 mmol) were used.

HRMS (70 eV, EI+): m/z calcd for $C_{45}H_{28}N_4$: 624.2314, found: 624.

Elemental Analysis: C, 87%; H, 5%

Comparative Synthesis Example 4: Synthesis of Compound Host 3

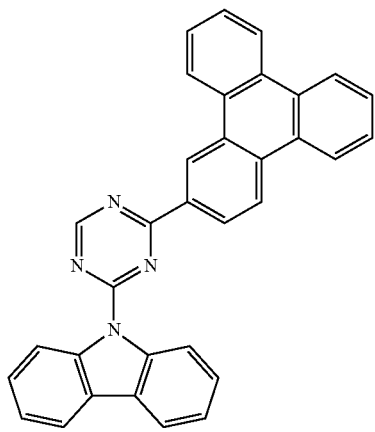

Host3

Compound Host 3 was synthesized referring to the synthesis method of patent KR 10-2012-0116282.

HRMS (70 eV, EI+): m/z calcd for $C_{33}H_2ON_4$: 472.1688, found: 472.

Elemental Analysis: C, 84%; H, 4%

Comparative Synthesis Example 5: Synthesis of Compound Host 4

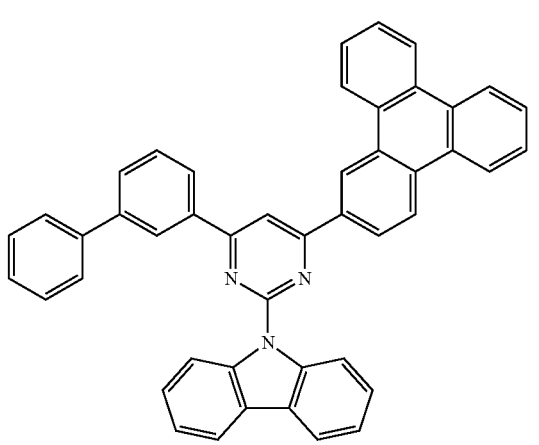

Host4

Compound Host 4 was synthesized referring to the synthesis method of patent KR 10-2012-0116282.

HRMS (70 eV, EI+): m/z calcd for $C_{46}H_{29}N_3$: 623.2361, found: 623.

Elemental Analysis: C, 89%; H, 5%

Comparative Synthesis Example 6: Synthesis of Compound Host 5

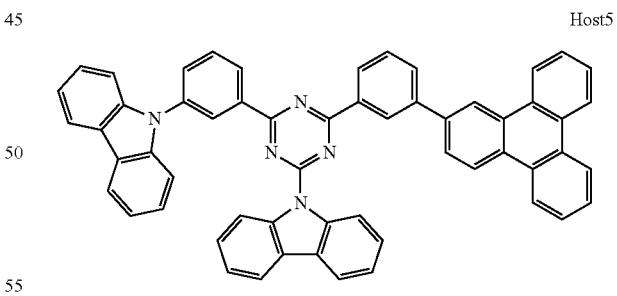

Host5

Compound Host 5 was synthesized referring to the synthesis method of patent KR 10-2012-0116282.

HRMS (70 eV, EI+): m/z calcd for $C_{57}H_{35}N_5$: 789.2892, found: 789.

Elemental Analysis: C, 87%; H, 4%

Comparative Synthesis Example 7: Synthesis of Compound Host 6

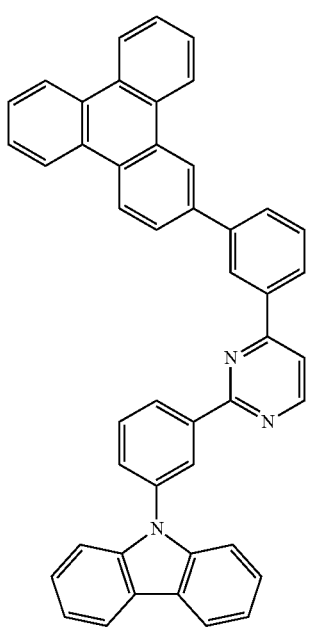

Host6

Compound Host 6 was synthesized referring to the synthesis method of patent KR 10-2012-0116282.

HRMS (70 eV, EI+): m/z calcd for $C_{46}H_{29}N_3$: 623.2361, found: 623.

Elemental Analysis: C, 89%; H, 5%

Comparative Synthesis Example 8: Synthesis of Compound Host 7

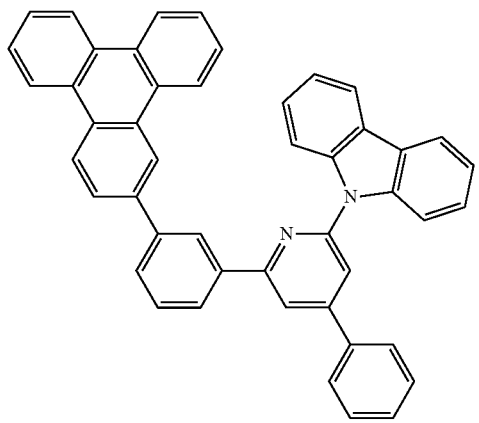

Host7

Compound Host 7 was synthesized referring to the synthesis method of patent KR 10-2014-0113483.

HRMS (70 eV, EI+): m/z calcd for $C_{47}H_{30}N_2$: 622.2409, found: 623.

Elemental Analysis: C, 91%; H, 5%

Comparative Synthesis Example 9: Synthesis of Compound Host 8

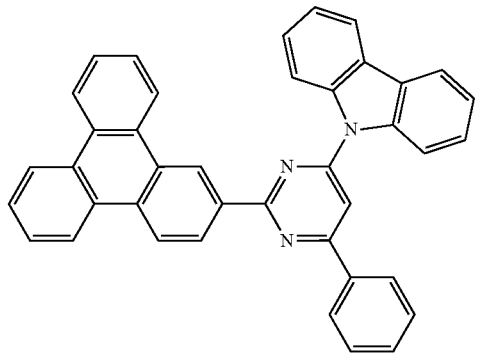

Host8 compound Host 8 was synthesized referring to the synthesis method of patent WO2017-069258.

HRMS (70 eV, EI+): m/z calcd for $C_{40}H_{25}N_3$: 547.2048, found: 547.

Elemental Analysis: C, 88%; H, 5%

Comparative Synthesis Example 10: Synthesis of Compound Host 9

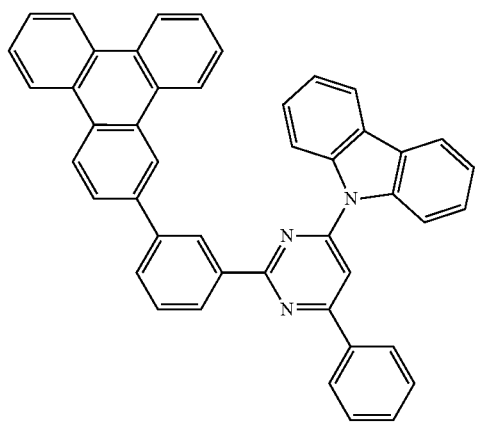

Host9

Compound Host 9 was synthesized referring to the synthesis method of patent WO2017-069258.

HRMS (70 eV, EI+): m/z calcd for $C_{46}H_{29}N_3$: 623.2361, found: 623.

Elemental Analysis: C, 89%; H, 5%

Comparative Synthesis Example 11: Synthesis of Compound Host 10

Host10

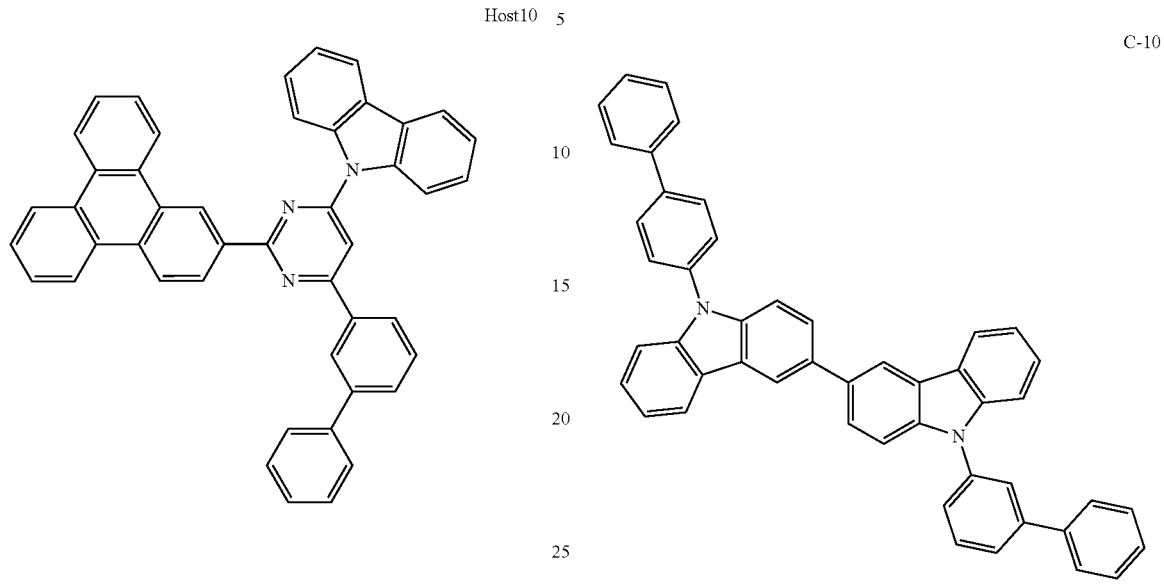

Compound Host 10 was synthesized, referring to the synthesis method of patent WO2017-069258.

HRMS (70 eV, EI+): m/z calcd for C46H29N3: 623.2361, found: 623.

Elemental Analysis: C, 89%; H, 5%

Synthesis Example 28: Synthesis of Compound C-1

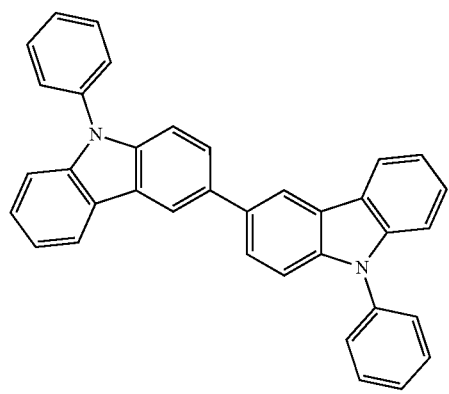

C-1

Compound C-1 was synthesized referring to the synthesis method of patent KR 10-2014-0042630.

HRMS (70 eV, EI+): m/z calcd for C36H24N2: 484.1939, found: 484.

Elemental Analysis: C, 89%; H, 5%

Synthesis Example 29: Synthesis of Compound C-10

C-10

Compound C-10 was synthesized referring to the synthesis method of patent KR 10-2014-0042630.

HRMS (70 eV, EI+): m/z calcd for C48H32N2: 636.2565, found: 636.

Elemental Analysis: C, 91%; H, 5%

(Measurement of Energy Level Using Cyclic Voltammetry (CV))

HOMO and LUMO of each compound were measured by using EC-Epsilon made by BAS (Bioanalytical Systems Inc. USA) and Cyclic Voltammetry consisting of a c-3 cell stand in the following method.

First, after setting a Ferrocene potential at −4.8 eV relative to a vacuum energy level, a reference electrode of Ag/Ag+ and an electrolyte prepared by dissolving tetrabutyl ammonium tetrafluoroborate in a dichloromethane solvent at a concentration of 0.1 M were used. Ferrocene and each compound were measured at 100 mV/sec, and HOMO and LUMO energy levels were calculated according to Calculation Equation.

HOMO(or LUMO)(eV)=−4.8−($E_{onset}-E_{1/2(Ferrocene)}$) <Calculation Equation>

Herein, $E_{onset}$ is a potential at which redox starts and $E_{1/2}$(Ferrocene) is a half-wave potential of ferrocene. The results are shown in Table 1.

TABLE 1

| Compound | HOMO (eV) | LUMO (eV) |
|---|---|---|
| 1 | −5.75 | −2.48 |
| 2 | −5.74 | −2.47 |
| 4 | −5.75 | −2.49 |
| 11 | −5.80 | −2.74 |
| 15 | −5.74 | −2.46 |
| 20 | −5.79 | −2.40 |
| 22 | −5.72 | −2.45 |
| Host 1 | −6.17 | −2.45 |
| Host 2 | −6.15 | −2.38 |
| Host 3 | −6.27 | −2.43 |
| Host 4 | −5.93 | −2.33 |
| Host 5 | −5.81 | −2.51 |
| Host 6 | −5.66 | −2.19 |

TABLE 1-continued

| Compound | HOMO (eV) | LUMO (eV) |
|---|---|---|
| Host 7 | −5.78 | −1.96 |
| Host 8 | −6.03 | −2.17 |
| Host 9 | −6.05 | −2.14 |
| Host 10 | −6.03 | −2.18 |

Referring to Table 1, Compounds 1, 2, 4, 11, 15, 20, and 22 exhibited a HOMO energy of greater than or equal to −5.80 eV and a LUMO energy of less than or equal to −2.40 eV and thus may be expected to easily inject and transport holes/electrons compared with Hosts 1 to 10.

(Manufacture of Organic Light Emitting Diode)

Example 1

ITO (indium tin oxide) was coated to be 1500 Å thick on a glass substrate, and the coated glass was ultrasonic wave-washed with a distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å-thick on the injection layer, and Compound C was deposited to be 1020 Å-thick to form a hole transport layer. On the hole transport layer, Compound 1 obtained in Synthesis Example 4 and Compound C-10 obtained in Synthesis Example 29 were used as a host and was doped with 10 wt % of tris(2-phenylpyridine)iridium(III) [Ir(ppy)$_3$] as a dopant to form a 400 Å-thick light emitting layer by vacuum deposition. Herein, Compound 1 and Compound C-1 were used in a ratio of 3:7. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer structure as follows:

A structure of ITO/Compound A (700 Å)/Compound B (50 Å)/Compound C (1020 Å)/EML[Compound 1:Compound C-10:Ir(ppy)$_3$=X:X:10%] (400 Å)/Compound D:Liq (300 Å)/Liq (15 Å)/Al (1200 Å). (X=weight ratio)

Compound A: N4,N4'-diphenyl-N4,N4'-bis(9-phenyl-9H-carbazol-3-yl)biphenyl-4,4'-diamine
Compound B: 1,4,5,8,9,11-hexaazatriphenylene-hexacarbonitrile (HAT-CN),
Compound C: N-(biphenyl-4-yl)-9,9-dimethyl-N-(4-(9-phenyl-9H-carbazol-3-yl)phenyl)-9H-fluoren-2-amine
Compound D: 8-(4-(4,6-di(naphthalen-2-yl)-1,3,5-triazin-2-yl)phenyl)quinoline Examples 2 to 18

Organic light emitting diodes were respectively manufactured according to the same method as Example 1 except for using the compositions in Table 2.

Comparative Examples 1 to 21

Organic light emitting diodes were respectively manufactured according to the same method as Example 1 except for using the compositions in Table 2.

Evaluation

Driving voltages, luminous efficiency, and life-span characteristics of the organic light emitting diodes according to Examples 1 to 18 and Comparative Examples 1 to 21 were evaluated.

Specific measurement methods are as follows, and the results are shown in Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

Life-span was obtained by measuring time taken until current efficiency (cd/A) decreased down to 97% while luminance (cd/m$^2$) was maintained at 6000 cd/m2.

(5) Measurement of Driving Voltage

A driving voltage of each diode was measured using a current-voltage meter (Keithley 2400) at 15 mA/cm$^2$ to obtain the results.

TABLE 2

| Nos. | Host First compound | Host Second compound | Weight ratio (first compound:second compound) | Driving voltage (V) | Color | Efficiency (cd/A) | Life-span T97 (h) |
|---|---|---|---|---|---|---|---|
| Ex. 1 | Compound 1 | Compound C-10 | 3:7 | 3.92 | green | 62.6 | 1,080 |
| Ex. 2 | Compound 2 | Compound C-10 | 3:7 | 3.85 | green | 65.4 | 1,150 |
| Ex. 3 | Compound 4 | Compound C-10 | 3:7 | 4.01 | green | 60.8 | 1,300 |
| Ex. 4 | Compound 11 | Compound C-10 | 3:7 | 4.17 | green | 60.1 | 1,420 |
| Ex. 5 | Compound 15 | Compound C-10 | 3:7 | 3.76 | green | 69.5 | 980 |
| Ex. 6 | Compound 20 | Compound C-10 | 3:7 | 4.02 | green | 63.4 | 1,200 |

TABLE 2-continued

| Nos. | Host First compound | Host Second compound | Weight ratio (first compound:second compound) | Driving voltage (V) | Color | Efficiency (cd/A) | Life-span T97 (h) |
|---|---|---|---|---|---|---|---|
| Ex. 7 | Compound 22 | Compound C-10 | 3:7 | 3.98 | green | 62.5 | 1,060 |
| Ex. 8 | Compound 1 | Compound C-1 | 3:7 | 3.86 | green | 64.1 | 950 |
| Ex. 9 | Compound 2 | Compound C-1 | 3:7 | 3.78 | green | 65.0 | 990 |
| Ex. 10 | Compound 1 | | — | 4.32 | green | 60.2 | 780 |
| Ex. 11 | Compound 2 | | — | 4.21 | green | 61.7 | 800 |
| Ex. 12 | Compound 4 | | — | 4.35 | green | 60.5 | 820 |
| Ex. 13 | Compound 11 | | — | 4.42 | green | 59.5 | 920 |
| Ex. 14 | Compound 15 | | — | 3.98 | green | 64.5 | 700 |
| Ex. 15 | Compound 20 | | — | 4.40 | green | 59.8 | 810 |
| Ex. 16 | Compound 22 | | — | 4.29 | green | 61.0 | 800 |
| Ex. 17 | Compound 1 | Compound C-10 | 4:6 | 3.77 | green | 62.8 | 1,000 |
| Ex. 18 | Compound 1 | Compound C-10 | 2:8 | 4.11 | green | 62.2 | 1,050 |
| Comp. Ex. 1 | CBP | | — | 5.5 | green | 19.3 | 0.5 |
| Comp. Ex. 2 | Host 1 | Compound C-10 | 3:7 | 4.29 | green | 65.8 | 540 |
| Comp. Ex. 3 | Host 2 | Compound C-10 | 3:7 | 4.6 | green | 58.0 | 460 |
| Comp. Ex. 4 | Host 3 | Compound C-10 | 3:7 | 4.95 | green | 43.5 | 10 |
| Comp. Ex. 5 | Host 4 | Compound C-10 | 3:7 | 4.81 | green | 60.0 | 210 |
| Comp. Ex. 6 | Host 5 | Compound C-10 | 3:7 | 4.75 | green | 55.1 | 450 |
| Comp. Ex. 7 | Host 6 | Compound C-10 | 3:7 | 4.70 | green | 45.5 | 50 |
| Comp. Ex. 8 | Host 7 | Compound C-10 | 3:7 | 5.10 | green | 35.8 | 10 |
| Comp. Ex. 9 | Host 8 | Compound C-10 | 3:7 | 4.95 | green | 61.5 | 150 |
| Comp. Ex. 10 | Host 9 | Compound C-10 | 3:7 | 4.92 | green | 58.0 | 200 |
| Comp. Ex. 11 | Host 10 | Compound C-10 | 3:7 | 5.3 | green | 2.8 | 10 |
| Comp. Ex. 12 | Host 1 | | — | 4.41 | green | 50.2 | 220 |
| Comp. Ex. 13 | Host 2 | | — | 4.50 | green | 52.1 | 180 |
| Comp. Ex. 14 | Host 3 | | — | 5.10 | green | 25.0 | 0 |
| Comp. Ex. 15 | Host 4 | | — | 4.38 | green | 52.5 | 110 |
| Comp. Ex. 16 | Host 5 | | — | 4.80 | green | 49.0 | 300 |
| Comp. Ex. 17 | Host 6 | | — | 4.82 | green | 35.0 | 10 |
| Comp. Ex. 18 | Host 7 | | — | 5.00 | green | 20.1 | 0 |
| Comp. Ex. 19 | Host 8 | | — | 4.40 | green | 52.1 | 55 |
| Comp. Ex. 20 | Host 9 | | — | 4.61 | green | 53.0 | 90 |
| Comp. Ex. 21 | Host 10 | | — | 4.45 | green | 48.3 | 100 |

Referring to Table 2, the organic light emitting diodes according to Examples 1 to 18 exhibited significantly improved driving voltages, luminous efficiency, and life-span characteristics compared with the organic light emitting diodes according to Comparative Examples 1 to 21. The reason is that the compounds of comparative examples had a deep HOMO energy level and a shallow LUMO compared with the compounds of examples and thus did not well inject and transport holes/electrons compared with the compounds of examples and resultantly, had a critical influence on a life-span of the organic light emitting diodes, as shown in Table 1. In addition, when a HT core of carbazole was directly linked to an ET core of triazine, there was an negative influence on a life-span. The reason is that since electron clouds of HOMO and LUMO were not separated, oxidization and reduction simultaneously occurred in the same parts and strained molecules.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

The invention claimed is:

1. A compound represented by Chemical Formula 1:

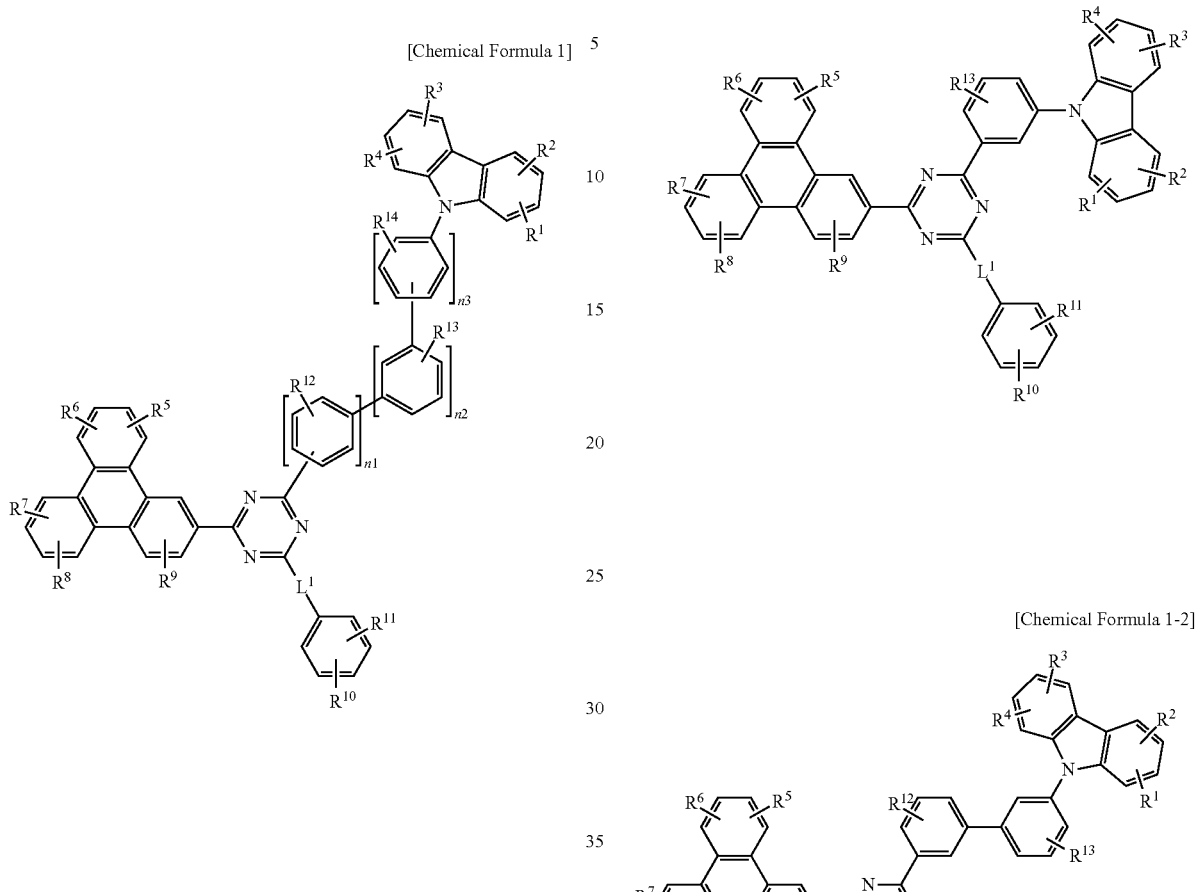

wherein, in Chemical Formula 1, $R^1$ to $R^{14}$ are independently hydrogen, deuterium, a substituted or unsubstituted C1 to C20 alkyl group, a substituted or unsubstituted C6 to C12 aryl group, a cyano group, or a combination thereof, $R^1$ and $R^2$ are independently present, $R^3$ and $R^4$ are independently present, $L^1$ is a single bond, a substituted or unsubstituted C6 to C30 arylene group, or a substituted or unsubstituted C2 to C30 heteroarylene group, n1 and n3 are independently 0 or 1, and n2 is 1.

2. The compound of claim 1, wherein a HOMO energy level calculated by the calculation equation is −6.0 eV to −5.0 eV and a LUMO energy level calculated by the calculation equation is −2.2 eV to −2.9 eV:

HOMO/LUMO energy level (eV)=−4.8−($E_{onset}$−$E_{1/2}$ (Ferrocene))     <Calculation Equation> wherein, $E_{onset}$ is a potential at which redox starts and $E_{1/2}$(Ferrocene) is a half-wave potential of ferrocene.

3. The compound of claim 1, wherein 0≤n1+n3≤1.

4. The compound of claim 1, wherein Chemical Formula 1 is represented by one of Chemical Formula 1-1 to Chemical Formula 1-6:

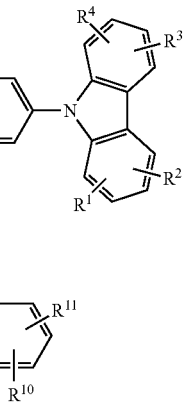

[Chemical Formula 1-1]

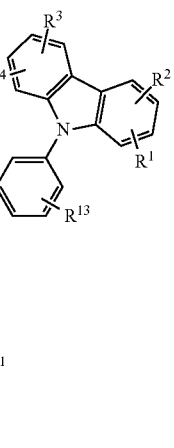

[Chemical Formula 1-2]

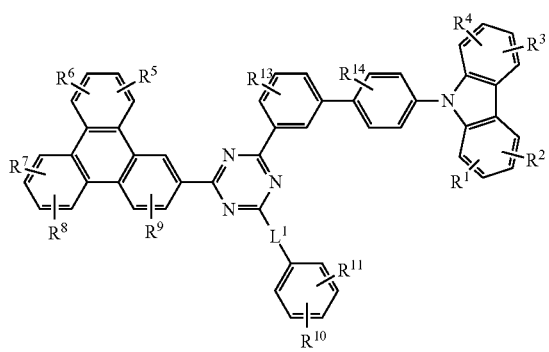

[Chemical Formula 1-3]

-continued

[Chemical Formula 1-4]

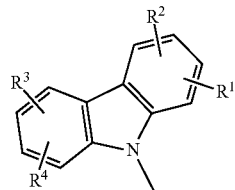

[Chemical Formula 1-5]

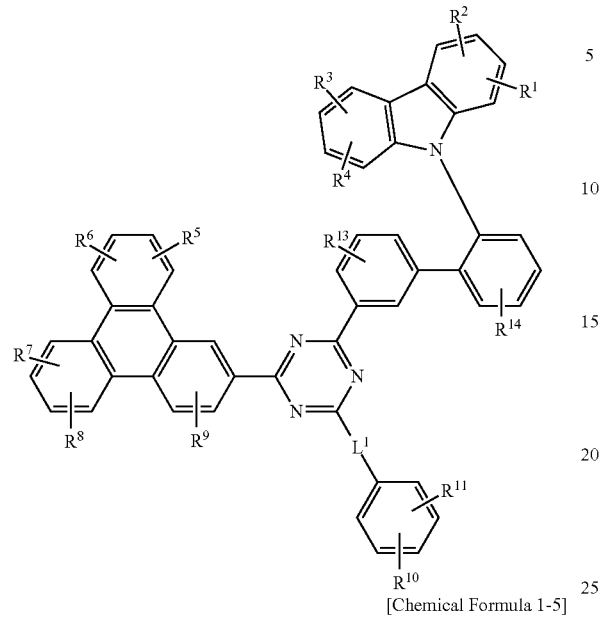

[Chemical Formula 1-6]

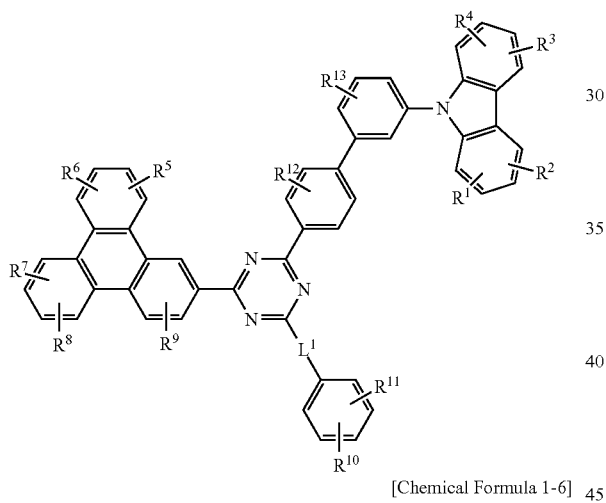

wherein, in Chemical Formula 1-1 to Chemical Formula 1-6,
$R^1$ to $R^{14}$ are independently hydrogen, deuterium, a substituted or unsubstituted C1 to C20 alkyl group, a substituted or unsubstituted C6 to C12 aryl group, a cyano group, or a combination thereof,
$R^1$ and $R^2$ are independently present,
$R^3$ and $R^4$ are independently present, and $L^1$ is a single bond, a substituted or unsubstituted C6 to C30 arylene group, or a substituted or unsubstituted C2 to C30 heteroarylene group.

5. The compound of claim 1, wherein the compound is a compound of Group 1:

[Group 1]

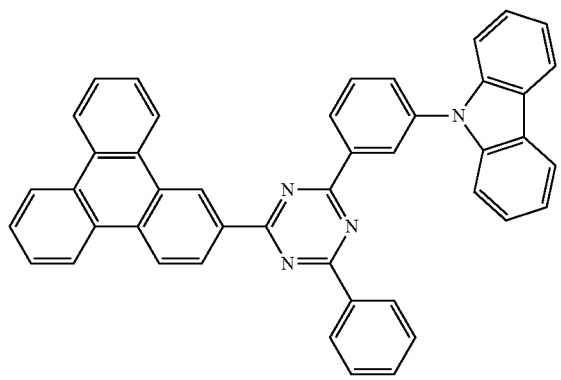

1

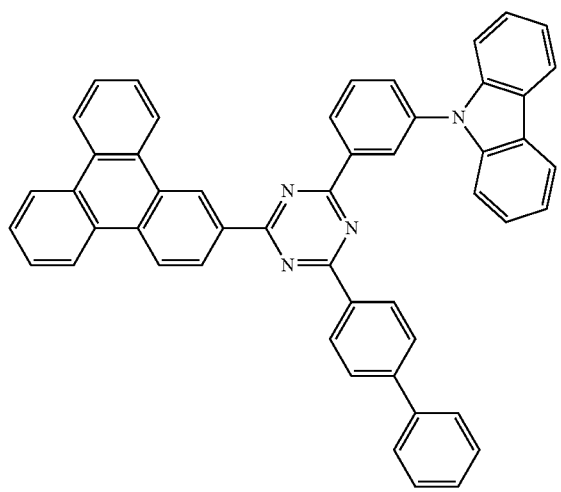

2

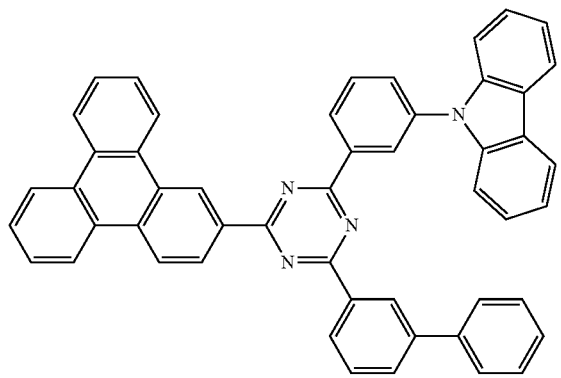

3

-continued
4
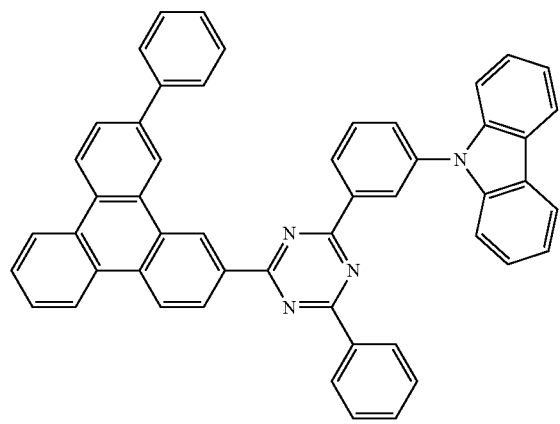
5
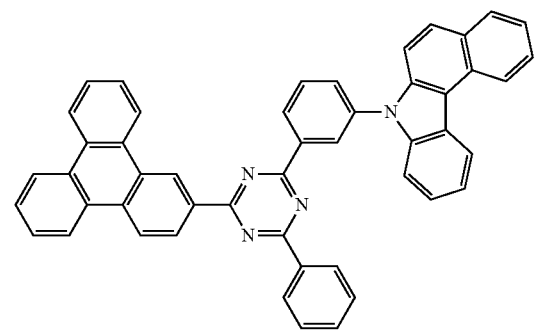
6
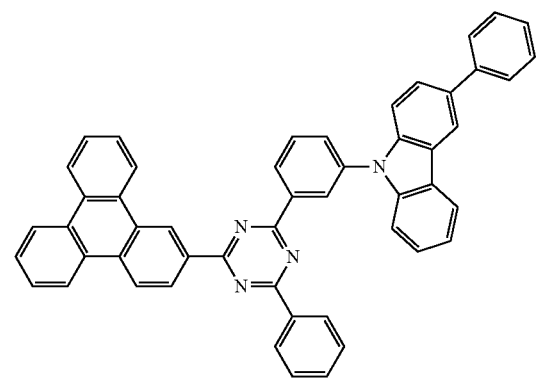
7
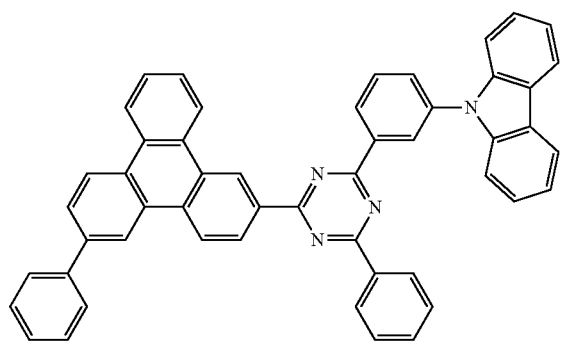
-continued
8
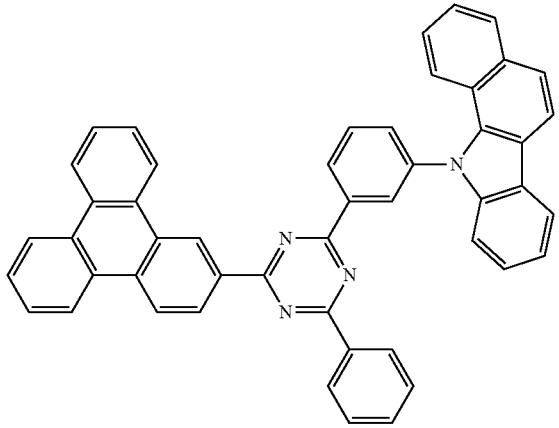
9
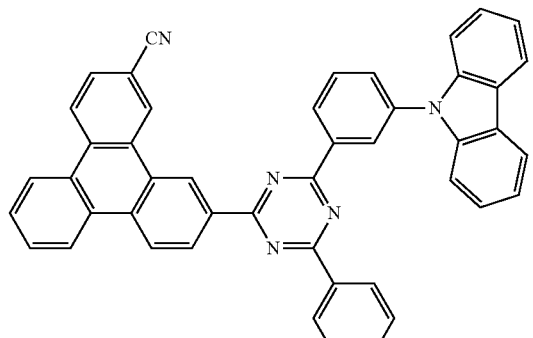
10
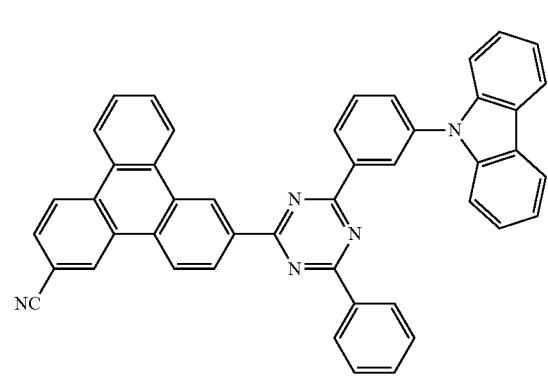
11
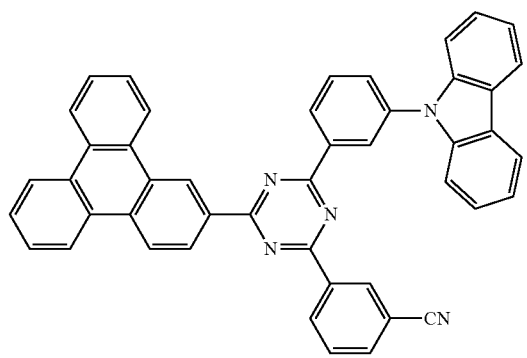

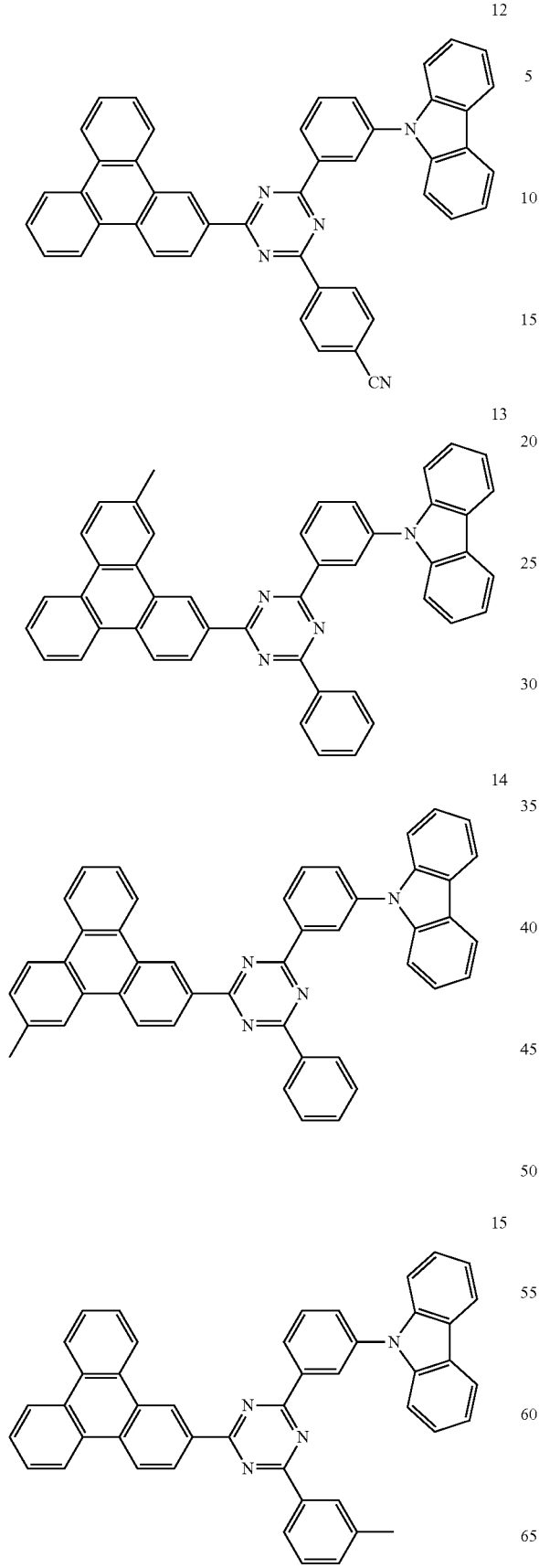
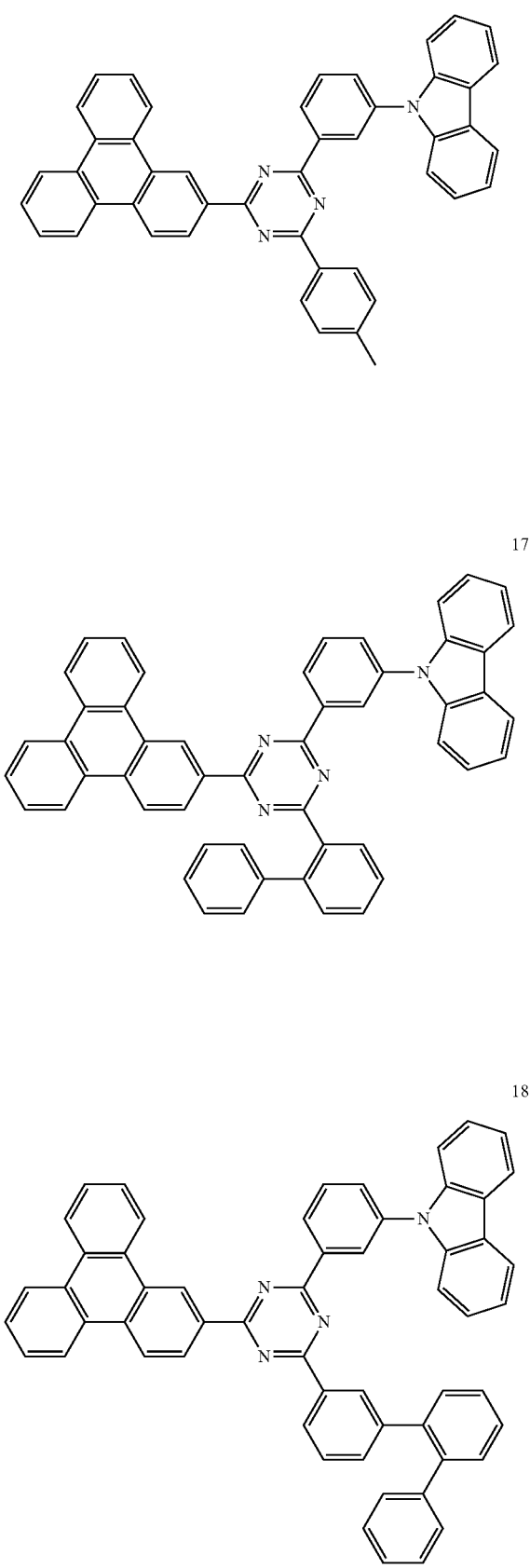

-continued

25
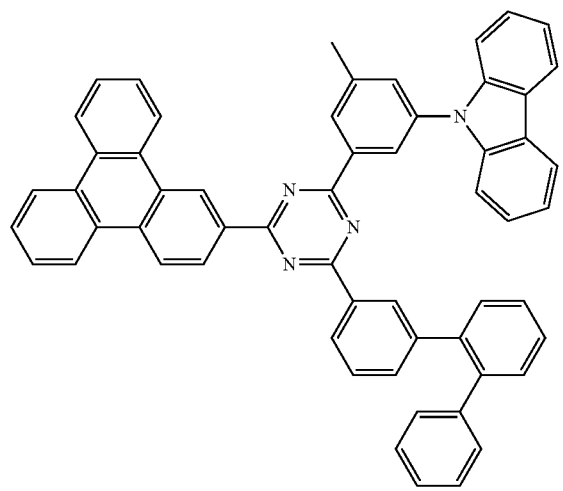
26
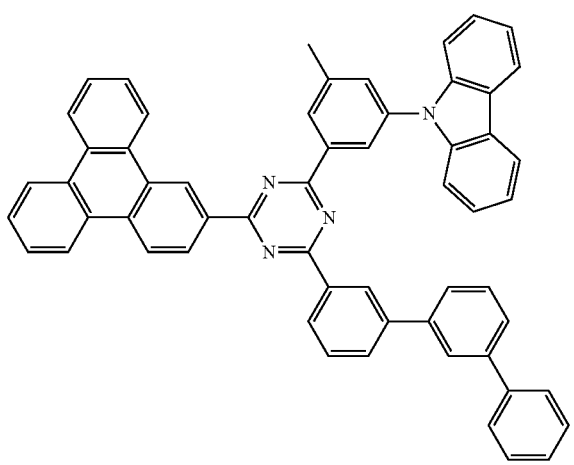
27
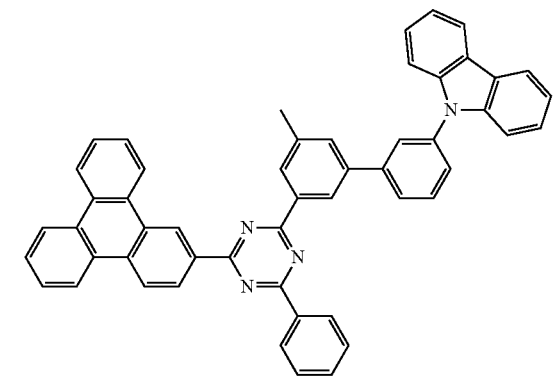
28
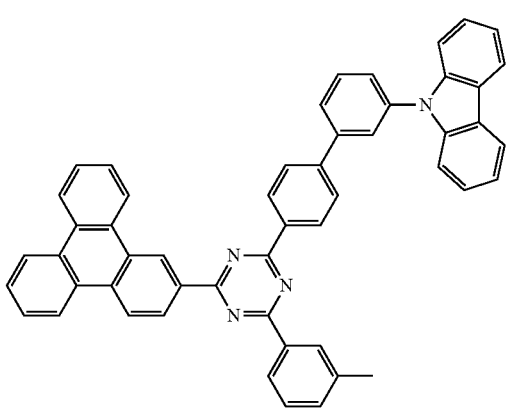
29
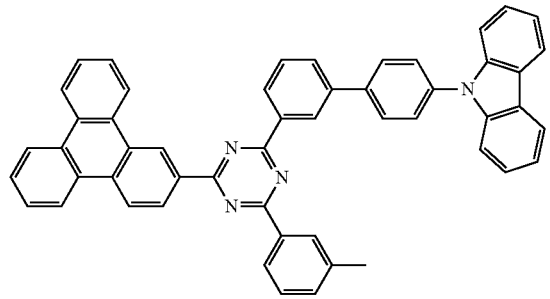
30
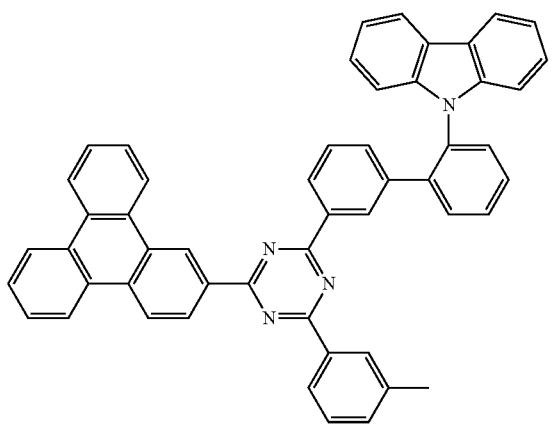
31
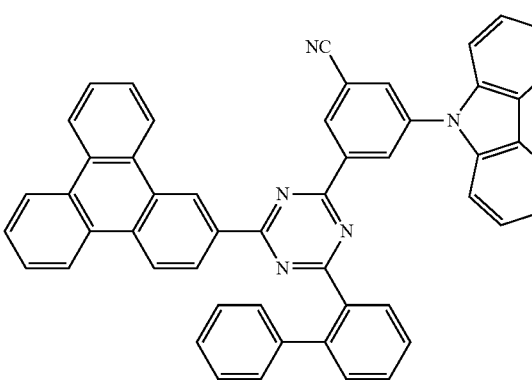

95

-continued

32

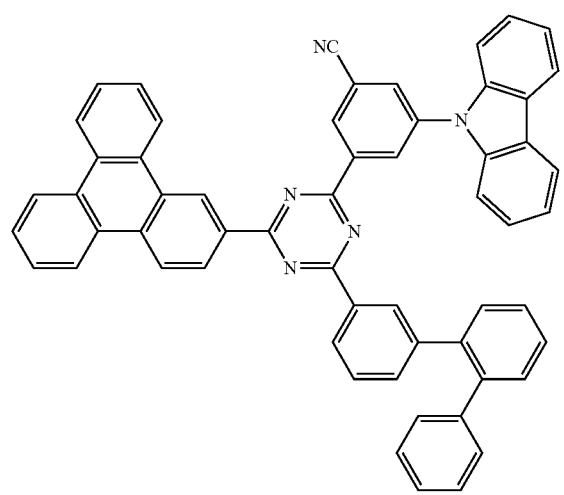

33

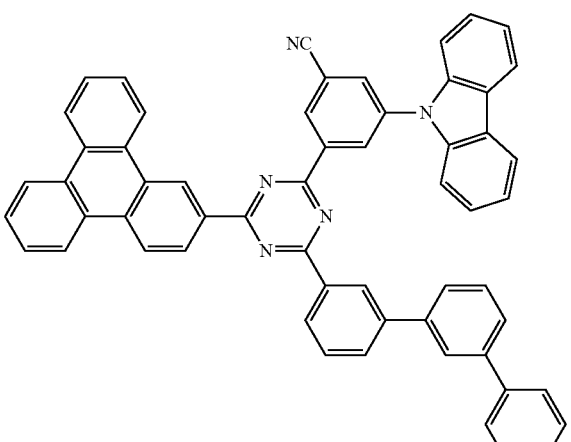

34

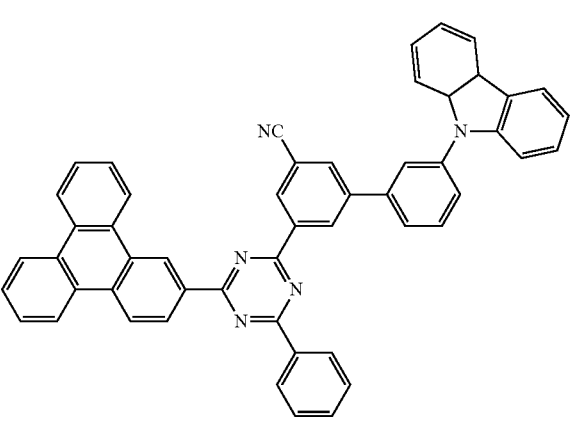

96

-continued

35

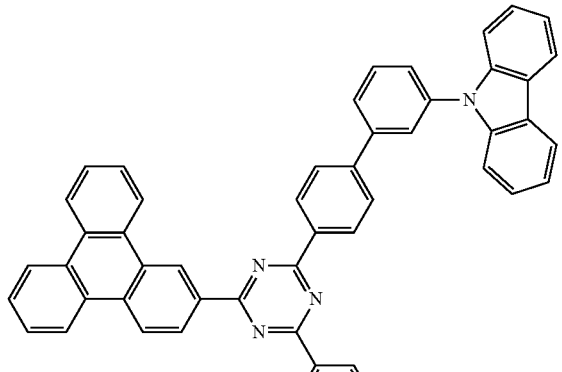

36

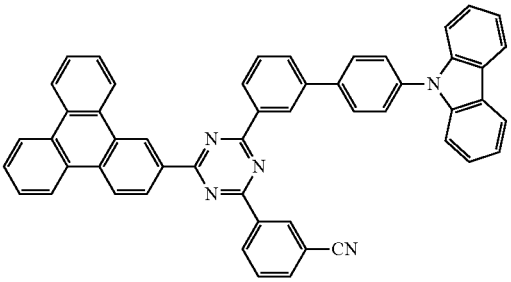

37

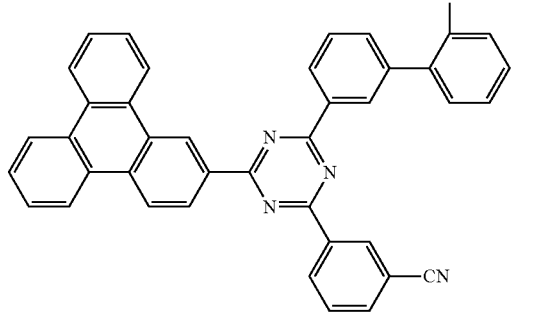

6. A composition comprising:
a host including the compound of claim 1, and
a dopant.

7. The composition of claim 6, wherein at least one of a difference between HOMO energy levels of the host and the dopant, and a difference between LUMO energy levels of the host and the dopant is 0 eV to 0.2 eV.

8. A composition, comprising:
a first compound, and
a second compound,
wherein:
the first compound is the compound of claim 1, and
the second compound is represented by Chemical Formula 2:

[Chemical Formula 2]

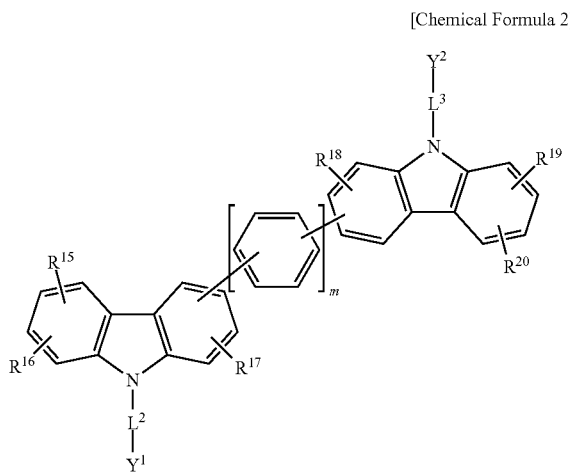

wherein, in Chemical Formula 2, $L^2$ and $L^3$ are independently a single bond, a substituted or unsubstituted C6 to C30 arylene group, or a substituted or unsubstituted C2 to C30 heteroarylene group, $Y^1$ and $Y^2$ are independently a substituted or unsubstituted C6 to C30 aryl group or a substituted or unsubstituted C2 to C30 heterocyclic group, $R^{15}$ to $R^{20}$ are independently hydrogen, deuterium, a substituted or unsubstituted C1 to C10 alkyl group, a substituted or unsubstituted C6 to C30 aryl group, a substituted or unsubstituted C2 to C30 heterocyclic group, a cyano group, or a combination thereof, and m is an integer of 0 to 2.

9. The composition of claim 8, wherein Chemical Formula 2 is represented by Chemical Formula 2-1 or Chemical Formula 2-2:

[Chemical Formula 2-1]

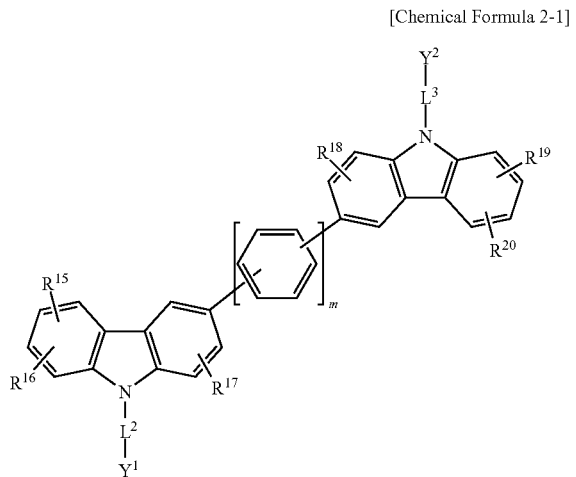

[Chemical Formula 2-2]

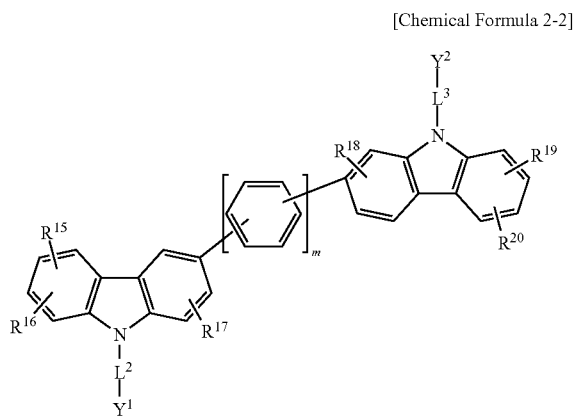

wherein, in Chemical Formulae 2-1 and 2-2, $L^2$ and $L^3$ are independently a single bond, a substituted or unsubstituted C6 to C30 arylene group, or a substituted or unsubstituted C2 to C30 heteroarylene group, $Y^1$ and $Y^2$ are independently a substituted or unsubstituted C6 to C30 aryl group or a substituted or unsubstituted C2 to C30 heterocyclic group, $R^{15}$ to $R^{20}$ are independently hydrogen, deuterium, a substituted or unsubstituted C1 to C10 alkyl group, a substituted or unsubstituted C6 to C30 aryl group, a substituted or unsubstituted C2 to C30 heterocyclic group, a cyano group, or a combination thereof, and m is an integer of 0 to 2.

10. The composition of claim 8, wherein the moieties *-$L^2$-$Y^1$ and *-$L^3$-$Y^2$ are independently a moiety of Group III:

[Group III]

B-1

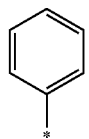

B-2

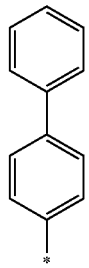

B-3

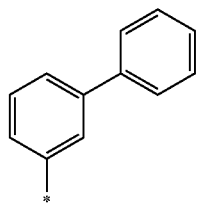

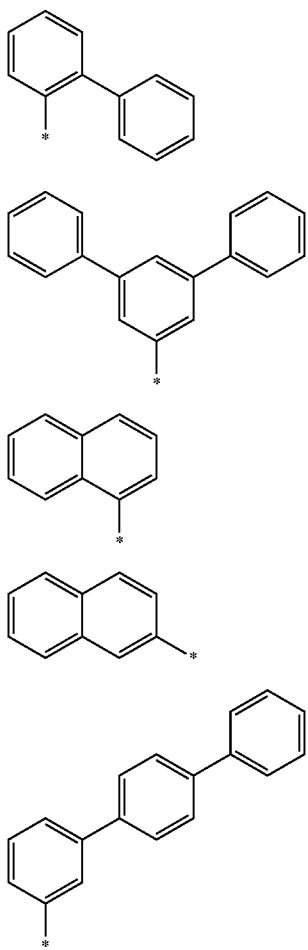
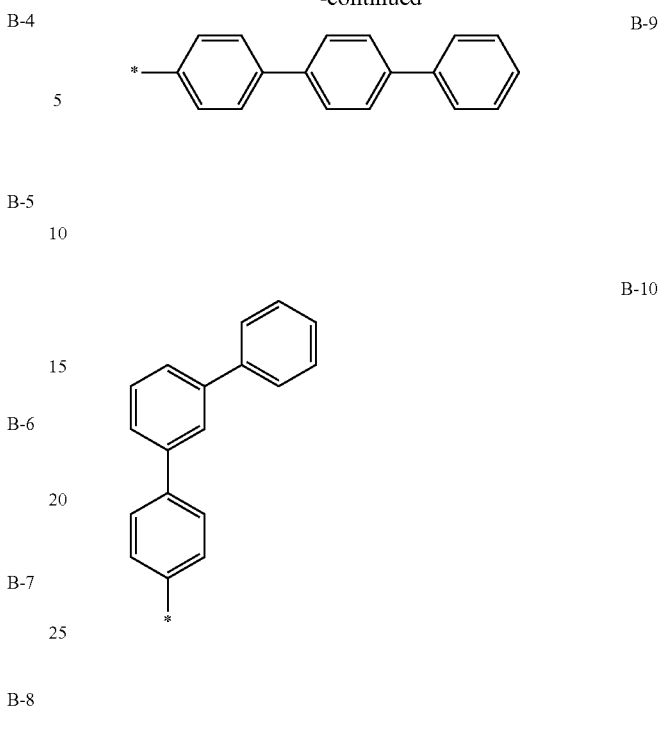
wherein, in Group III, * is a linking point.
11. The composition of claim 8, wherein:
the first compound is represented by one of Chemical Formula 1-1 to Chemical Formula 1-3, and
the second compound is represented by Chemical Formula 2-1:
[Chemical Formula 1-1]
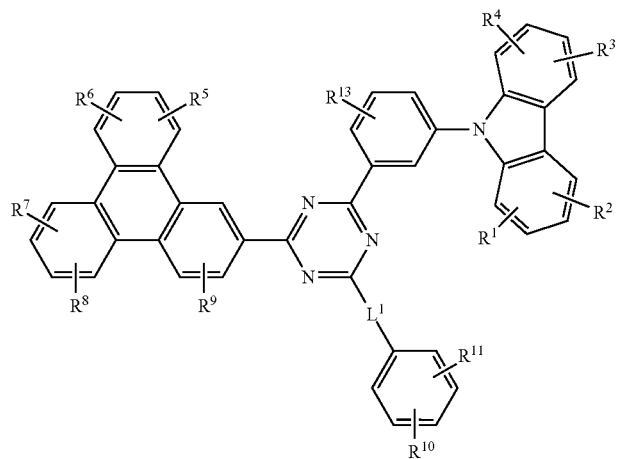

-continued

[Chemical Formula 1-2]

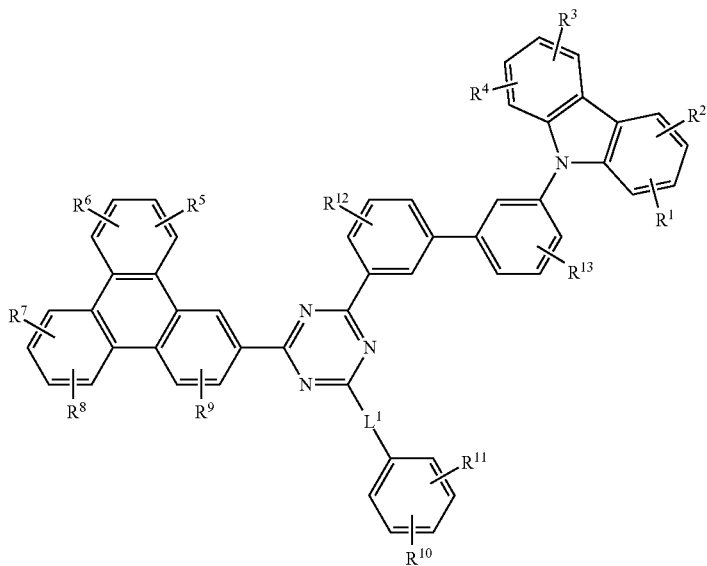

[Chemical Formula 1-3]

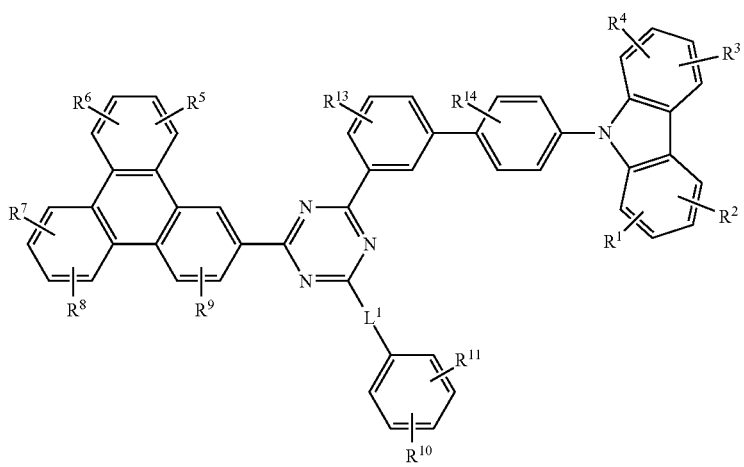

wherein, in Chemical Formula 1-1 to Chemical Formula 1-3, $R^1$ to $R^{14}$ are independently hydrogen, deuterium, a substituted or unsubstituted C1 to C20 alkyl group, a substituted or unsubstituted C6 to C12 aryl group, a cyano group, or a combination thereof, $R^1$ and $R^2$ are independently present, $R^3$ and $R^4$ are independently present, and $L^1$ is a single bond, a substituted or unsubstituted C6 to C30 arylene group, or a substituted or unsubstituted C2 to C30 heteroarylene group;

[Chemical Formula 2-1]

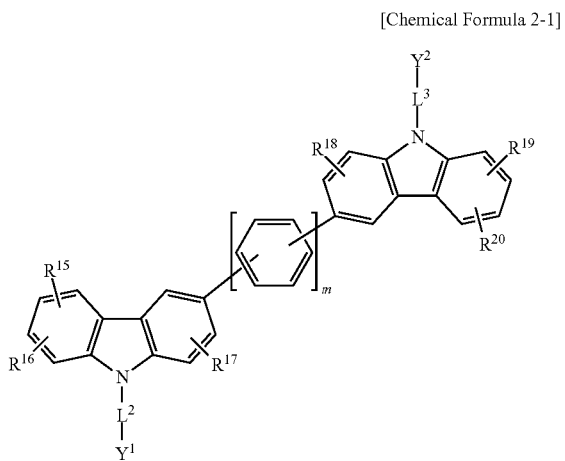

wherein, in Chemical Formula 2-1, $L^2$ and $L^3$ are independently a single bond, a substituted or unsubstituted C6 to C30 arylene group, or a substituted or unsubstituted C2 to C30 heteroarylene group, $Y^1$ and $Y^2$ are independently a substituted or unsubstituted C6 to C30 aryl group or a substituted or unsubstituted C2 to C30 heterocyclic group, $R^{15}$ to $R^{20}$ are independently hydrogen, deuterium, a substituted or unsubstituted C1 to C10 alkyl group, a substituted or unsubstituted C6 to C30 aryl group, a substituted or unsubstituted C2 to C30 heterocyclic group, a cyano group, or a combination thereof, and m is an integer of 0 to 2.

12. The composition of claim 8, further comprising a dopant.

13. The composition of claim 12, wherein at least one of a difference between HOMO energy levels between a host including the first compound and the second compound and the dopant; and a difference between LUMO energy levels between the host including the first compound and the second compound and the dopant is 0 eV to 0.2 eV.

14. An organic optoelectronic diode, comprising
an anode and a cathode facing each other, and
at least one organic layer disposed between the anode and the cathode,
wherein the organic layer comprises the compound of claim 1.

15. The organic optoelectronic diode of claim 14, wherein the organic layer comprises a light emitting layer, and the light emitting layer comprises the compound.

16. A display device comprising the organic optoelectronic diode of claim 14.

17. An organic optoelectronic diode, comprising:
an anode and a cathode facing each other; and
at least one organic layer disposed between the anode and the cathode,
wherein the organic layer comprises the composition of claim 6.

18. An organic optoelectronic diode, comprising:
an anode and a cathode facing each other; and
at least one organic layer disposed between the anode and the cathode,
wherein the organic layer comprises the composition of claim 8.

19. The organic optoelectronic diode of claim 18, wherein:
the organic layer comprises a light emitting layer, and the light emitting layer comprises the composition.

20. A display device comprising the organic optoelectronic diode of claim 18.

* * * * *